United States Patent
Ikeda et al.

(10) Patent No.: US 11,635,686 B2
(45) Date of Patent: Apr. 25, 2023

(54) RESIST COMPOSITION, METHOD OF FORMING RESIST PATTERN, AND COMPOUND

(71) Applicant: TOKYO OHKA KOGYO CO., LTD., Kawasaki (JP)

(72) Inventors: Takuya Ikeda, Kawasaki (JP); Junichi Miyakawa, Kawasaki (JP)

(73) Assignee: TOKYO OHKA KOGYO CO., LTD., Kawasaki (JP)

(*) Notice: Subject to any disclaimer, the term of this patent is extended or adjusted under 35 U.S.C. 154(b) by 416 days.

(21) Appl. No.: 16/700,846

(22) Filed: Dec. 2, 2019

(65) Prior Publication Data
US 2020/0174366 A1 Jun. 4, 2020

(30) Foreign Application Priority Data
Dec. 4, 2018 (JP) .............................. JP2018-227633

(51) Int. Cl.
| | |
|---|---|
| *G03F 7/004* | (2006.01) |
| *C07C 321/30* | (2006.01) |
| *G03F 7/20* | (2006.01) |
| *G03F 7/038* | (2006.01) |

(52) U.S. Cl.
CPC .......... *G03F 7/0046* (2013.01); *C07C 321/30* (2013.01); *G03F 7/0045* (2013.01); *G03F 7/0382* (2013.01); *G03F 7/2004* (2013.01); *G03F 7/2059* (2013.01)

(58) Field of Classification Search
CPC .... G03F 7/0046; G03F 7/0045; G03F 7/0382; G03F 7/2004; G03F 7/2059; G03F 7/0392; G03F 7/0395; G03F 7/0397; G03F 7/039; C07C 321/30; C07C 381/12; C09D 11/101; Y10S 430/106; Y10S 430/115; Y10S 430/12; Y10S 430/123; Y10S 430/122; C07D 333/54; C07D 333/34

See application file for complete search history.

(56) References Cited

U.S. PATENT DOCUMENTS

| | | | |
|---|---|---|---|
| 6,664,022 B1 | 12/2003 | Cameron et al. | |
| 2003/0013049 A1* | 1/2003 | Cameron | G03F 7/0045 430/311 |
| 2003/0039916 A1* | 2/2003 | Adegawa | G03F 7/0392 430/270.1 |
| 2010/0113818 A1 | 5/2010 | Oh et al. | |

FOREIGN PATENT DOCUMENTS

| | | |
|---|---|---|
| JP | 2004-521372 A | 7/2004 |
| JP | 2007-284405 A | 11/2007 |
| JP | B-5149236 | 2/2013 |

OTHER PUBLICATIONS

Office Action issued is corresponding Japanese Patent Application No. 2018-227633, dated Aug. 9, 2022.

* cited by examiner

*Primary Examiner* — Duane Smith
*Assistant Examiner* — Richard David Champion
(74) *Attorney, Agent, or Firm* — Knobbe, Martens, Olson & Bear, LLP

(57) ABSTRACT

A resist composition containing a base material component (A) of which solubility in a developing solution is changed due to an action of an acid and a compound represented by Formula (bd1); in the formula, $R^{bd1}$ to $R^{bd3}$ each independently represent an aryl group which may have a substituent, provided that at least two of $R^{bd1}$ to $R^{bd3}$ are aryl groups having one or more fluorine atoms as substituents, and at least one of the fluorine atoms of the aryl group is bonded to a carbon atom adjacent to a carbon atom that is bonded to the sulfur atom in the formula, and the total number of the fluorine atoms is 4 or more; $X^-$ represents a counter anion.

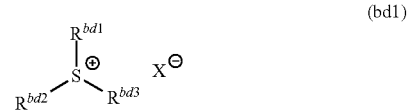

(bd1)

4 Claims, No Drawings

RESIST COMPOSITION, METHOD OF FORMING RESIST PATTERN, AND COMPOUND

BACKGROUND OF THE INVENTION

Field of the Invention

The present invention relates to a resist composition, a method of forming a resist pattern, and a compound.

Priority is claimed on Japanese Patent Application No. 2018-227633, filed on Dec. 4, 2018, the content of which is incorporated herein by reference.

Description of Related Art

In lithography techniques, for example, a resist film formed of a resist material is formed on a substrate, and the resist film is subjected to selective exposure, followed by developing treatment, thereby forming a resist pattern having a predetermined shape on the resist film. A resist material with which the exposed portions of the resist film become soluble in a developing solution is called a positive-tone, and a resist material with which the exposed portions of the resist film become insoluble in a developing solution is called a negative-tone.

In recent years, in the production of semiconductor elements and liquid crystal display elements, advances in lithography techniques have led to rapid progress in the field of pattern miniaturization. Typically, these miniaturization techniques involve shortening the wavelength (increasing the energy) of the exposure light source. In particular, ultraviolet radiation typified by g-line and i-line radiation has been used conventionally, but nowadays KrF excimer lasers and ArF excimer lasers are used in mass production of semiconductor elements. Furthermore, research is also being conducted into an exposure light source having a wavelength shorter (energy higher) than these excimer lasers, such as extreme ultraviolet radiation (EUV), electron beam (EB), and X-rays.

Resist materials require lithography characteristics such as high resolution capable of reproducing patterns of minute dimensions, and a high level of sensitivity to these types of exposure light sources.

As a resist material that satisfies these requirements, in the related art, a chemically amplified resist composition which contains a base material component of which solubility in a developing solution is changed due to an action of an acid and an acid generator component that generates an acid upon exposure has been used.

For example, as a positive chemically amplified resist composition when the developing solution is an alkali developing solution (alkali development process), a composition which contains a resin component (base resin) of which solubility in an alkali developing solution is increased due to an action of an acid and an acid generator component has been typically used. In a case where a resist film formed using such a resist composition is selectively exposed at the time of forming a resist pattern, in exposed portions, an acid is generated from the acid generator component so that the polarity of the base resin is increased due to the action of the acid, and thus the exposed portions of the resist film become soluble in the alkali developing solution. Accordingly, by conducting alkali development, a positive-tone pattern in which the unexposed portions of the resist film remain as a pattern is formed.

On the other hand, when such a chemically amplified resist composition is applied to a solvent developing process using a developing solution containing an organic solvent (organic developing solution), the solubility in an organic developing solution decreases as the polarity of the base resin increases, thus the unexposed portion of the resist film is dissolved and removed by the organic developing solution to form a negative-tone resist pattern in which the exposed portion of the resist film remains as a pattern. Such a solvent developing process for forming a negative-tone resist pattern is also referred to as "negative-tone developing process."

The base resin used in the chemically amplified resist composition generally has a plurality of constitutional units in order to improve the lithography characteristics and the like.

For example, in a case of the resin component of which solubility in an alkali developing solution is increased due to the action of an acid, a constitutional unit containing an acid decomposable group which is decomposed due to the action of an acid generated from an acid generator to increase polarity is used. Additionally, constitutional units containing a lactone-containing cyclic group and constitutional units containing a polar group such as a hydroxyl group are used in combination.

Furthermore, the behavior of the acid generated from the acid generator component upon exposure is considered to be a factor which greatly affects the lithography characteristics upon forming a resist pattern.

As the acid generator to be used in the chemically amplified resist composition, various acid generators have been suggested so far. For example, an onium salt-based acid generator such as iodonium salt or sulfonium salt, an oxime sulfonate-based acid generator, a diazomethane-based acid generator, a nitrobenzyl sulfonate-based acid generator, an iminosulfonate-based acid generator, and a disulfone-based acid generator have been known.

As the onium salt-based acid generator, an acid generator having an onium ion such as triphenylsulfonium in a cation moiety is mainly used. Generally, an alkyl sulfonate ion or a fluorinated alkyl sulfonate ion in which some or all of hydrogen atoms of the alkyl group are substituted with fluorine atoms is used in an anion moiety of the onium salt-based acid generator.

Moreover, the onium salt-based acid generator having an anion having a specific structure containing an aromatic ring as the anion moiety of the onium salt-based acid generator is also proposed in order to improve the lithography characteristics upon forming the resist pattern (for example, see Patent Literature 1).

DOCUMENTS OF RELATED ART

Patent Literature

[Patent Literature 1] Japanese Patent No. 5149236

SUMMARY OF THE INVENTION

As further advances in lithography technology and miniaturization of resist patterns continue to progress, for example, in lithography using electron beam or EUV, fine patterning of several tens of nm is a goal to be achieved. As stated above, as the resist pattern has a smaller size, the resist composition is required to have high sensitivity to the exposure light source and good lithography characteristics such as roughness reduction.

However, when an attempt to increase sensitivity to an exposure light source such as EUV is made to the resist composition containing the already-known onium salt-based acid generator as stated above, there is a problem in that it is difficult to obtain a desired resist pattern shape and the like, and thus it is difficult to satisfy all of these characteristics.

The present invention has been made in consideration of the above-described circumstances, and an object thereof is to provide a novel compound for a resist composition, a resist composition containing the compound, and a method of forming a resist pattern using the resist composition.

In order to achieve the objects, the present invention is made as follows.

That is, according to a first aspect of the present invention, there is provided a resist composition which generates an acid upon exposure and of which solubility in a developing solution is changed due to an action of an acid, the resist composition including: a base material component (A) of which solubility in a developing solution is changed due to an action of an acid; and a compound (BD1) including an anion moiety and a cation moiety and represented by Formula (bd1).

(bd1)

[In the formula, $R^{bd1}$ to $R^{bd3}$ each independently represent an aryl group which may have a substituent. Here, at least two of $R^{bd1}$ to $R^{bd3}$ are aryl groups having one or more fluorine atoms as substituents, and at least one of the fluorine atoms of the aryl group is bonded to a carbon atom adjacent to a carbon atom that is bonded to a sulfur atom in the formula. In $R^{bd1}$ to $R^{bd3}$, the total number of the fluorine atoms bonded as substituents to the carbon atom adjacent to the carbon atom that is bonded to the sulfur atom in the formula is 4 or more. Two of $R^{bd1}$ to $R^{bd3}$ may be bonded to each other to form a fused ring together with the sulfur atom in the formula. $X^-$ represents a counter anion.]

According to a second aspect of the present invention, there is provided a method of forming a resist pattern, including: a step of forming a resist film on a support using the resist composition according to the first aspect; a step of exposing the resist film; and a step of developing the exposed resist film to form a resist pattern.

According to a third aspect of the present invention, there is provided a compound including an anion moiety and a cation moiety and represented by Formula (bd1).

(bd1)

[In the formula, $R^{bd1}$ to $R^{bd3}$ each independently represent an aryl group which may have a substituent. Here, at least two of $R^{bd1}$ to $R^{bd3}$ are aryl groups having one or more fluorine atoms as substituents, and at least one of the fluorine atoms of the aryl group is bonded to a carbon atom adjacent to a carbon atom that is bonded to a sulfur atom in the formula. In $R^{bd1}$ to $R^{bd3}$, the total number of the fluorine atoms bonded as substituents to the carbon atom adjacent to the carbon atom that is bonded to the sulfur atom in the formula is 4 or more. Two of $R^{bd1}$ to $R^{bd3}$ may be bonded to each other to form a fused ring together with the sulfur atom in the formula. $X^-$ represents a counter anion.]

According to the present invention, it is possible to provide a novel compound for a resist composition, a resist composition containing the compound, and a method of forming a resist pattern using the resist composition.

According to the resist composition of the present invention, it is possible to form a resist pattern with improved lithography characteristics (roughness reduction and the like) and to achieve high sensitivity in forming a resist pattern.

DETAILED DESCRIPTION OF THE INVENTION

In the present specification and claims, the term "aliphatic" is a relative concept used in relation to the term "aromatic", and defines a group or compound that has no aromaticity.

The term "alkyl group" includes linear, branched or cyclic monovalent saturated hydrocarbon groups, unless otherwise specified. The same applies for the alkyl group in an alkoxy group.

The term "alkylene group" includes linear, branched or cyclic divalent saturated hydrocarbon groups, unless otherwise specified.

A "halogenated alkyl group" is a group in which some or all hydrogen atoms of an alkyl group are substituted with halogen atoms. Examples of the halogen atom include a fluorine atom, a chlorine atom, a bromine atom, and an iodine atom.

A "fluorinated alkyl group" or a "fluorinated alkylene group" is a group in which some or all hydrogen atoms of an alkyl group or an alkylene group have been substituted with fluorine atoms.

The term "constitutional unit" indicates a monomer unit that contributes to the formation of a polymer compound (a resin, a polymer, or a copolymer).

The expression "may have a substituent" means that a case where a hydrogen atom (—H) is substituted with a monovalent group, or a case where a methylene (—CH$_2$—) group is substituted with a divalent group.

The term "exposure" is used as a general concept that includes irradiation with any form of radiation.

A "constitutional unit derived from acrylic acid ester" indicates a constitutional unit that is formed by the cleavage of the ethylenic double bond of acrylic acid ester.

The "acrylic acid ester" indicates a compound in which the terminal hydrogen atom of the carboxy group of acrylic acid (CH$_2$=CH—COOH) has been substituted with an organic group.

The acrylic acid ester may have the hydrogen atom bonded to the carbon atom at the α-position substituted with a substituent. The substituent ($R^{\alpha 0}$) that substitutes the hydrogen atom bonded to the carbon atom at the α-position is an atom other than hydrogen atom or a group, and examples thereof include an alkyl group having 1 to 5 carbon atoms and a halogenated alkyl group having 1 to 5 carbon atoms. Further, itaconic acid diester in which a substituent ($R^{\alpha 0}$) has been substituted with a substituent containing an ester bond, or α-hydroxyalkyl acrylic acid ester in which a substituent ($R\alpha^0$) has been substituted with a hydroxyalkyl group or a group in which the hydroxyl group in a hydroxyalkyl group has been modified can be exemplified. A carbon atom at the α-position of acrylic acid ester indicates the carbon atom that is bonded to the carbonyl group, unless specified otherwise.

Hereinafter, acrylic acid ester in which the hydrogen atom bonded to the carbon atom at the α-position is substituted with a substituent is also referred to as "α-substituted acrylic acid ester." Further, acrylic acid ester and α-substituted acrylic acid ester are also collectively referred to as "(α-substituted) acrylic acid ester."

A "constitutional unit derived from acrylamide" indicates a constitutional unit that is formed by the cleavage of the ethylenic double bond of acrylamide.

The acrylamide may have the hydrogen atom bonded to the carbon atom at the α-position substituted with a substituent, and may have either or both hydrogen atoms on the amino group of acrylamide substituted with a substituent. A carbon atom at the α-position of acrylamide indicates the carbon atom that is bonded to the carbonyl group of acrylamide, unless specified otherwise.

As the substituent which substitutes the hydrogen atom bonded to the carbon atom at the α-position of acrylamide, the same substituents as those described above for the substituent ($R^{\alpha 0}$) at the α-position of the above-described α-position of the above-described α-substituted acrylic acid ester can be exemplified.

A "constitutional unit derived from hydroxystyrene" indicates a constitutional unit that is formed by the cleavage of an ethylenic double bond of hydroxystyrene. A "constitutional unit derived from a hydroxystyrene derivative" indicates a constitutional unit that is formed by the cleavage of an ethylenic double bond of a hydroxystyrene derivative.

The term "hydroxystyrene derivative" includes compounds in which the hydrogen atom at the α-position of hydroxystyrene has been substituted with another substituent such as an alkyl group or a halogenated alkyl group; and derivatives thereof. Examples of the derivatives thereof include hydroxystyrene in which the hydrogen atom of the hydroxyl group has been substituted with an organic group and may have the hydrogen atom at the α-position substituted with a substituent; and hydroxystyrene which has a substituent other than a hydroxyl group bonded to the benzene ring and may have the hydrogen atom at the α-position substituted with a substituent. Here, the α-position (carbon atom at the α-position) indicates the carbon atom having the benzene ring bonded thereto, unless specified otherwise.

As the substituent which substitutes the hydrogen atom at the α-position of hydroxystyrene, the same substituents as those described above for the substituent at the α-position of the above-described α-substituted acrylic acid ester can be exemplified.

A "constitutional unit derived from vinylbenzoic acid or a vinylbenzoic acid derivative" indicates a constitutional unit that is formed by the cleavage of the ethylenic double bond of vinylbenzoic acid or a vinylbenzoic acid derivative.

The term "vinylbenzoic acid derivative" includes compounds in which the hydrogen atom at the α-position of vinylbenzoic acid has been substituted with another substituent such as an alkyl group or a halogenated alkyl group; and derivatives thereof. Examples of the derivatives thereof include vinylbenzoic acid in which the hydrogen atom of the carboxy group has been substituted with an organic group and may have the hydrogen atom at the α-position substituted with a substituent; and vinylbenzoic acid which has a substituent other than a hydroxyl group and a carboxy group bonded to the benzene ring and may have the hydrogen atom at the α-position substituted with a substituent. Here, the α-position (carbon atom at the α-position) indicates the carbon atom having the benzene ring bonded thereto, unless specified otherwise.

The term "styrene derivative" is a concept including those obtained by substitution of a hydrogen atom at the α-position of styrene with other substituents such as an alkyl group and a halogenated alkyl group; and these derivatives. Examples of these derivatives include those obtained by bonding a substituent to a benzene ring of hydroxystyrene in which a hydrogen atom at the α-position may be substituted with a substituent. Here, the α-position (carbon atom at the α-position) indicates the carbon atom having the benzene ring bonded thereto, unless specified otherwise.

The term "constitutional unit derived from styrene" or "constitutional unit derived from a styrene derivative" indicates a constitutional unit formed by cleavage of an ethylenic double bond of styrene or a styrene derivative.

As the alkyl group as a substituent at the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group, a neopentyl group and the like.

Specific examples of the halogenated alkyl group as the substituent at the α-position include groups in which some or all hydrogen atoms of the above-described "alkyl group as the substituent at the α-position" are substituted with halogen atoms. Examples of the halogen atom include a fluorine atom, a chlorine atom, a bromine atom and an iodine atom, and a fluorine atom is particularly preferable.

Specific examples of the hydroxyalkyl group as the substituent at the α-position include groups in which some or all hydrogen atoms of the above-described "alkyl group as the substituent at the α-position" are substituted with a hydroxyl group. The number of hydroxyl groups in the hydroxyalkyl group is preferably 1 to 5, and most preferably 1.

In the present specification and claims, asymmetric carbons may be present or enantiomers or diastereomers may be present depending on the structures of the chemical formulae. In this case, these isomers are represented by one chemical formula. These isomers may be used alone or in the form of a mixture.

(Resist Composition)

The resist composition according to the first aspect of the present invention is a resist composition which generates an acid upon exposure and of which solubility in a developing solution is changed due to an action of an acid. The resist composition includes a base material component (A) (hereinafter, also referred to as a "component (A)") of which solubility in a developing solution is changed due to the action of an acid; and a compound (BD1) (hereinafter, also referred to as a "component (BD1)"), which is represented by Formula (bd1).

One embodiment of the resist composition contains the component (A) and an acid generator component (B) (hereinafter also referred to as a "component (B)") which generates an acid upon exposure. It is preferred that the resist composition further contains a base component (hereinafter also referred to as a "component (D)") that traps an acid generated from the component (B) upon exposure (i.e. controlling acid diffusion), in addition to the component (A) and the component (B).

In the resist composition of the present embodiment, the component (BD1) may be used as the component (B) or as the component (D) by selecting a counter anion (anion moiety).

In a case where a resist film is formed using the resist composition according to the present embodiment and the formed resist film is subjected to a selective exposure, acid is generated from the component (B) at exposed portions of the resist film, and the generated acid acts on the component (A) to change the solubility of the component (A) in a developing solution, whereas the solubility of the component (A) in a developing solution is not changed at unexposed portions of the resist film, thereby generating difference in solubility in a developing solution between exposed portions and unexposed portions. Therefore, by subjecting the resist film to development, the exposed portions of the resist film are dissolved and removed to form a positive-tone resist pattern in a case of a positive-tone resist composition, whereas the unexposed portions of the resist film are dissolved and removed to form a negative-tone resist pattern in a case of a negative-tone resist composition.

In the present specification, a resist composition which forms a positive-tone resist pattern by dissolving and removing the exposed portions of the resist film is called a positive-tone resist composition, and a resist composition which forms a negative-tone resist pattern by dissolving and removing the unexposed portions of the resist film is called a negative-tone resist composition.

The resist composition of the present embodiment may be a positive-tone resist composition or a negative-tone resist composition. Further, in the formation of a resist pattern, the resist composition of the present embodiment can be applied to an alkali developing process using an alkali developing solution in the developing treatment, or a solvent developing process using a developing solution containing an organic solvent (organic developing solution) in the developing treatment.

The resist composition of the present embodiment has an acid generating ability to generate an acid upon exposure, and the component (A) may generate an acid upon exposure in addition to the component (B).

In a case where the component (A) generates an acid upon exposure, the component (A) is defined as a "base material component which generates an acid upon exposure and of which solubility in a developing solution is changed due to the action of an acid."

In a case where the component (A) is a base material component which generates an acid upon exposure and of which solubility in a developing solution is changed due to the action of an acid, it is preferred that the component (A1) described later generates an acid upon exposure, and is a polymer compound of which solubility in a developing solution is changed due to the action of an acid. Such a polymer compound is exemplified by a resin which has a constitutional unit for generating an acid upon exposure. Well-known monomers may be used as a monomer that leads to a constitutional unit that generates an acid upon exposure.

<Component (A)>

In the resist composition of the present embodiment, the component (A) is a base material component of which solubility in a developing solution is changed due to the action of an acid.

In the present embodiment, the term "base material component" indicates an organic compound capable of forming a film, and is preferably an organic compound having a molecular weight of 500 or greater. In a case where the organic compound has a molecular weight of 500 or greater, the film-forming ability is improved, and a resist pattern at a nano level can be easily formed.

The organic compound used as the base material component is broadly classified into non-polymers and polymers.

In general, as a non-polymer, any of those which have a molecular weight in the range of 500 or greater and less than 4,000 is used. Hereinafter, a "low molecular weight compound" indicates a non-polymer having a molecular weight in the range of 500 or greater and less than 4,000.

As a polymer, any of those which have a molecular weight of 1,000 or greater is generally used. Hereinafter, a "resin", "polymer compound" or "polymer" indicates a polymer having a molecular weight of 1,000 or greater.

As the molecular weight of the polymer, the weight average molecular weight in terms of the polystyrene equivalent value determined by gel permeation chromatography (GPC) is used.

In a case where the resist composition of the present embodiment is a "negative-tone resist composition for an alkali developing process" which forms a negative-tone resist pattern in an alkali developing process, or alternatively, in a case where it is a "positive-tone resist composition for a solvent developing process" which forms a positive-tone resist pattern in a solvent developing process, the component (A) is preferably a base material component (A-2) (hereinafter referred to as a "component (A-2)"), which is soluble in an alkali developing solution. A crosslinking agent component is further blended thereto. In the resist composition, for example, when an acid is generated from the component (B) upon exposure, the acid acts to cause crosslinking between the component (A-2) and the crosslinking agent component. Consequently, the solubility in the alkali developing solution is decreased (the solubility in the organic developing solution is increased).

Therefore, in a case where a resist film obtained by coating the resist composition on a support is selectively exposed at the time of forming a resist pattern, the exposed portions of the resist film are poorly soluble in the alkali developing solution (but easily soluble in the organic developing solution). On the other hand, the unexposed portions of the resist film remain as being soluble in the alkali developing solution (poorly soluble in the organic developing solution). Accordingly, the negative-tone resist pattern is formed by developing with the alkali developing solution. Alternatively, the positive-tone resist pattern is formed by developing with the organic developing solution.

A preferred component (A-2) is a resin soluble in the alkali developing solution (hereinafter referred to as an "alkali-soluble resin").

Preferred examples of the alkali-soluble resin include a resin having a constitutional unit derived from at least one selected from alkyl ester of α-(hydroxyalkyl) acrylic acid or α-(hydroxyalkyl) acrylic acid (preferably alkylester having 1 to 5 carbon atoms), which is disclosed in Japanese Unexamined Patent Application, First Publication No. 2000-206694; an acrylic resin or a polycycloolefin resin disclosed in U.S. Pat. No. 6,949,325, in which a hydrogen atom bonded to a carbon atom at the α-position having a sulfonamide group may be optionally substituted with a substituent; an acrylic resin containing fluorinated alcohol, in which a hydrogen atom bonded to a carbon atom at the α-position may be optionally substituted with a substituent, which is disclosed in U.S. Pat. No. 6,949,325, Japanese Unexamined Patent Application, First Publication No. 2005-336452 and Japanese Unexamined Patent Application, First Publication No. 2006-317803; a polycycloolefin resin having fluorinated alcohol, which is disclosed in, for example, Japanese Unexamined Patent Application, First Publication No. 2006-259582, since these resins can form a resist pattern with minimal swelling.

The α-(hydroxyalkyl) acrylic acid refers to either or both of acrylic acid in which a hydrogen atom is bonded to a carbon atom at the α-position to which a carboxy group is bonded, and α-hydroxyalkyl acrylic acid in which a hydroxyalkyl group (preferably a hydroxyalkyl group having 1 to 5 carbon atoms) is bonded to the carbon atom at this α-position, among the acrylic acids in which the hydrogen atom bonded to the carbon atom at the α-position may be optionally substituted with a substituent.

As the crosslinking agent component, for example, it is preferable to use an amino-based crosslinking agent such as glycoluril having a methylol group or an alkoxymethyl group, or a melamine-based crosslinking agent, since a good resist pattern with little swelling is easily formed. The blending amount of the crosslinking agent component is preferably 1 to 50 parts by mass based on 100 parts by mass of the alkali-soluble resin.

In a case where the resist composition of the present embodiment is a "positive-tone resist composition for an alkali developing process" which forms a positive-tone resist pattern in an alkali developing process, or alternatively, in a case where it is a "negative-tone resist composition for a solvent developing process" which forms a negative-tone resist pattern in a solvent developing process, the component (A) is preferably a base material component (A-1) (hereinafter referred to as a "component (A-1)"), of which polarity is increased due to the action of an acid. By using the component (A-1), the polarity of the base material component changes before and after exposure, so that good development contrast can be obtained not only in the alkali developing process but also in the solvent developing process.

In a case where the alkali developing process is applied, the component (A-1) is poorly soluble in the alkali developing solution before exposure. For example, in a case where an acid is generated from the component (B) upon exposure, the acid acts to cause that the polarity is increased to increase the solubility in the alkali developing solution. Therefore, when the resist film obtained by coating the resist composition on a support is selectively exposed at the time of forming a resist pattern, the exposed portions of the resist film shift from being poorly soluble to soluble in the alkali developing solution. On the other hand, the unexposed portions of the resist film remain as being poorly soluble in alkali, thus the positive-tone resist pattern is formed by alkali development.

Meanwhile, in a case where the solvent developing process is applied, the component (A-1) has high solubility in an organic developing solution before exposure. In a case where when an acid is generated from the component (B) upon exposure, the polarity is increased due to the action of the acid, and the solubility in the organic developing solution is decreased. Therefore, in a case where a resist film obtained by coating the resist composition on a support is selectively exposed at the time of forming a resist pattern, the exposed portions of the resist film shift from being soluble to being poorly soluble in the organic developing solution. On the other hand, the unexposed portions of the resist film remain as being soluble, thus the development can be carried out with the organic developing solution to provide contrast between the exposed portions and the unexposed portions, thereby forming the negative-tone resist pattern.

In the resist composition of the present embodiment, the component (A) may be used alone or in combination of two or more.

In the resist composition of the present embodiment, the component (A) is preferably the component (A-1). That is, the resist composition of the present embodiment is preferably the "positive-tone resist composition for an alkali developing process", which forms the positive-tone resist pattern in the alkali developing process, or alternatively, the "negative-tone resist composition for a solvent developing process" which forms the negative-tone resist pattern in the solvent developing process. As the component (A), at least one of a polymer compound and a low molecular weight compound can be used.

In a case where the component (A) is the component (A-1), it is preferable that the component (A-1) contains a resin component (A1) (hereinafter also referred to as a "component (A1)").

Regarding Component (A1)

The component (A1) is a resin component, which preferably contains a polymer compound having a constitutional unit (a1) containing an acid decomposable group of which polarity is increased due to the action of an acid.

The component (A1) preferably further has a constitutional unit (a10) containing a hydroxystyrene skeleton, in addition to the constitutional unit (a1).

Furthermore, the component (A1) preferably further has a constitutional unit (a2) containing a lactone-containing cyclic group, a —SO$_2$-containing cyclic group or a carbonate-containing cyclic group, in addition to the constitutional unit (a1).

Furthermore, the component (A1) preferably further has a constitutional unit (a3) containing a polar group-containing aliphatic hydrocarbon group (here, a constitutional unit corresponding to the constitutional unit (a1) or the constitutional unit (a2) is excluded), in addition to the constitutional unit (a1).

The component (A1) may have a constitutional unit other than the constitutional unit (a1), the constitutional unit (a2), the constitutional unit (a3), and the constitutional unit (a10).

<<Constitutional Unit (a1)>>

The constitutional unit (a1) is a constitutional unit containing an acid decomposable group of which polarity is increased due to the action of an acid.

The term "acid decomposable group" indicates a group having acid decomposability in which at least a part of a bond in the structure of the acid decomposable group can be cleaved due to the action of an acid.

Examples of the acid decomposable group of which polarity is increased due to the action of an acid include groups which are decomposed due to the action of an acid to generate a polar group.

Examples of the polar group include a carboxy group, a hydroxyl group, an amino group, a sulfo group (—SO$_3$H) and the like. Among these, a polar group containing —OH in a structure thereof (hereinafter, also referred to as an "OH-containing polar group") is preferable, a carboxy group or a hydroxyl group is more preferable, and a carboxy group is particularly preferable.

More specific examples of the acid decomposable group include a group in which the above-described polar group has been protected with an acid dissociable group (such as a group in which a hydrogen atom of the OH-containing polar group has been protected with an acid dissociable group).

Here, the "acid dissociable group" indicates both (i) group having acid dissociability in which a bond between the acid dissociable group and an atom adjacent to the acid dissociable group can be cleaved due to the action of an acid; and (ii) group in which some bonds are cleaved due to the action of an acid, and then a decarboxylation reaction occurs, thereby cleaving the bond between the acid dissociable group and the atom adjacent to the acid dissociable group.

It is necessary that the acid dissociable group that constitutes the acid decomposable group is a group which exhibits a lower polarity than the polar group generated by the dissociation of the acid dissociable group. Thus, in a case where the acid dissociable group is dissociated due to the action of an acid, a polar group exhibiting a higher polarity than that of the acid dissociable group is generated, thereby increasing the polarity. As a result, the polarity of the entire component (A1) is increased. By the increase in the polarity, relatively, the solubility in a developing solution changes, and the solubility in an alkali developing solution is increased, whereas the solubility in an organic developing solution is decreased.

Examples of the acid dissociable group are the same as those which have been proposed as acid dissociable groups for the base resin for a chemically amplified resist composition.

Specific examples of acid dissociable groups for the base resin for a conventional chemically amplified resist composition include an "acetal type acid dissociable group", a "tertiary alkyl ester type acid dissociable group", and a "tertiary alkyloxycarbonyl acid dissociable group" described below.

Acetal Type Acid Dissociable Group:

Examples of the acid dissociable group for protecting a carboxy group or a hydroxyl group as a polar group include the acid dissociable group represented by Formula (a1-r-1) shown below (hereinafter, also referred to as "acetal type acid dissociable group").

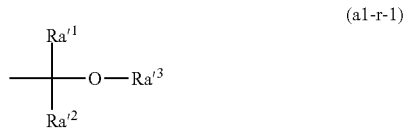

(a1-r-1)

[In the formula, Ra'$^1$ and Ra'$^2$ each represent a hydrogen atom or an alkyl group. Ra'$^3$ represents a hydrocarbon group. Here, Ra'$^3$ may be bonded to Ra'$^1$ or Ra'$^2$ to form a ring.]

In Formula (a1-r-1), it is preferable that at least one of Ra'$^1$ and Ra'$^2$ represents a hydrogen atom and more preferable that both of Ra'$^1$ and Ra'$^2$ represent a hydrogen atom.

In a case where Ra'$^1$ or Ra'$^2$ represents an alkyl group, examples of the alkyl group include the same alkyl groups exemplified as the substituent which may be bonded to the carbon atom at the α-position in the description on α-substituted acrylic acid ester. Among these, an alkyl group having 1 to 5 carbon atoms is preferable. More specific preferable examples thereof include linear or branched alkyl groups. Specific examples of the alkyl group include a methyl group, an ethyl group, a propyl group, an isopropyl group, an n-butyl group, an isobutyl group, a tert-butyl group, a pentyl group, an isopentyl group, a neopentyl group and the like. Among these, a methyl group or an ethyl group is more preferable, and a methyl group is particularly preferable.

In Formula (a1-r-1), examples of the hydrocarbon group as Ra'$^3$ include a linear or branched alkyl group and a cyclic hydrocarbon group.

The linear alkyl group has preferably 1 to 5 carbon atoms, more preferably 1 to 4 carbon atoms, and still more preferably 1 or 2 carbon atoms. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The branched alkyl group has preferably 3 to 10 carbon atoms and more preferably 3 to 5 carbon atoms. Specific examples thereof include an isopropyl group, an isobutyl group, a tert-butyl group, an isopentyl group, a neopentyl group, a 1,1-diethylpropyl group, a 2,2-dimethylbutyl group and the like. Among these, an isopropyl group is preferable.

In a case where Ra'$^3$ represents a cyclic hydrocarbon group, the cyclic hydrocarbon group may be an aliphatic hydrocarbon group or an aromatic hydrocarbon group, and may be a polycyclic group or a monocyclic group.

As the aliphatic hydrocarbon group which is a monocyclic group, a group in which one hydrogen atom has been removed from a monocycloalkane is preferable. The monocycloalkane has preferably 3 to 6 carbon atoms, and specific examples thereof include cyclopentane and cyclohexane.

As the aliphatic hydrocarbon group which is a polycyclic group, a group in which one hydrogen atom has been removed from a polycycloalkane is preferable. The polycycloalkane has preferably 7 to 12 carbon atoms, and specific examples thereof include adamantane, norbornane, isobornane, tricyclodecane, tetracyclododecane and the like.

In a case where the cyclic hydrocarbon group as Ra'$^3$ becomes an aromatic hydrocarbon group, the aromatic hydrocarbon group is a hydrocarbon group having at least one aromatic ring.

The aromatic ring is not particularly limited as long as it is a cyclic conjugated system having (4n+2) π electrons, and may be monocyclic or polycyclic. The aromatic ring has preferably 5 to 30 carbon atoms, more preferably 5 to 20 carbon atoms, still more preferably 6 to 15 carbon atoms, and particularly preferably 6 to 12 carbon atoms.

Specific examples of the aromatic ring include aromatic hydrocarbon rings such as benzene, naphthalene, anthracene, and phenanthrene; and aromatic heterocyclic rings in which some carbon atoms constituting the above-described aromatic hydrocarbon rings have been substituted with hetero atoms. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group as Ra'$^3$ include a group in which one hydrogen atom has been removed from the above-described aromatic hydrocarbon ring or aromatic heterocyclic ring (an aryl group or a heteroaryl group); a group in which one hydrogen atom has been removed from an aromatic compound having two or more aromatic rings (biphenyl, fluorene or the like); and a group in which one hydrogen atom of the above-described aromatic hydrocarbon ring or aromatic heterocyclic ring has been substituted with an alkylene group (an arylalkyl group such as a benzyl group, a phenethyl group, a 1-naphthylmethyl group, a 2-naphthylmethyl group, a 1-naphthylethyl group, a 2-naphthylethyl group or the like). The alkylene group which is bonded to the above-described aromatic hydrocarbon ring or aromatic heterocyclic ring has preferably 1 to 4 carbon atoms, more preferably 1 or 2 carbon atoms, and particularly preferably 1 carbon atom.

The cyclic hydrocarbon group as $Ra^{t3}$ may have a substituent. Examples of the substituent include —$R^{P1}$, —$R^{P2}$—O—$R^{P1}$, —$R^{P2}$—CO—$R^{P1}$, —$R^{P2}$—CO—$OR^{P1}$, —$R^{P2}$—O—CO—$R^1$, —$R^{P2}$—OH, —$R^{P2}$—CN, and —$R^{P2}$—COOH (hereinafter, these substituents are also collectively referred to as "$Ra^{05}$")

Here, $R^{P1}$ represents a chain-like monovalent saturated hydrocarbon group having 1 to 10 carbon atoms, a monovalent aliphatic cyclic saturated hydrocarbon group having 3 to 20 carbon atoms, or a monovalent aromatic hydrocarbon group having 6 to 30 carbon atoms. Further, $R^{P2}$ represents a single bond, a chain-like divalent saturated hydrocarbon group having 1 to 10 carbon atoms, a divalent aliphatic cyclic saturated hydrocarbon group having 3 to 20 carbon atoms, or a divalent aromatic hydrocarbon group having 6 to 30 carbon atoms.

Here, some or all hydrogen atoms in the chain-like saturated hydrocarbon group, the aliphatic cyclic saturated hydrocarbon group, and the aromatic hydrocarbon group as $R^{P1}$ and $R^{P2}$ may be substituted with fluorine atoms. The aliphatic cyclic hydrocarbon group may have one or more of one kind of substituents or one or more of each of plural kinds of the substituents.

Examples of the chain-like monovalent saturated hydrocarbon group having 1 to 10 carbon atoms include a methyl group, an ethyl group, a propyl group, a butyl group, a pentyl group, a hexyl group, a heptyl group, an octyl group, a decyl group and the like.

Examples of the monovalent aliphatic cyclic saturated hydrocarbon group having 3 to 20 carbon atoms include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, a cyclododecyl group or the like; and a polycyclic aliphatic saturated hydrocarbon group such as a bicyclo[2.2.2]octanyl group, a tricyclo[5.2.1.02,6]decanyl group, a tricyclo[3.3.1.13,7]decanyl group, a tetracyclo[6.2.1.13,6.02,7]dodecanyl group, an adamantyl group or the like.

Examples of the monovalent aromatic hydrocarbon group having 6 to 30 carbon atoms include a group formed by removing one hydrogen atom from an aromatic hydrocarbon ring, such as benzene, biphenyl, fluorene, naphthalene, anthracene, or phenanthrene.

In a case where $Ra^{t3}$ is bonded to $Ra^{t1}$ or $Ra^{t2}$ to form a ring, the cyclic group is preferably a 4- to 7-membered ring, and more preferably a 4- to 6-membered ring. Specific examples of the cyclic group include a tetrahydropyranyl group and a tetrahydrofuranyl group.

Tertiary Alkyl Ester Type Acid Dissociable Group:

Examples of the acid dissociable group for protecting the carboxy group as a polar group include the acid dissociable group represented by Formula (a1-r-2) shown below.

Among the acid dissociable groups represented by Formula (a1-r-2), for convenience, a group which is constituted of alkyl groups is referred to as "tertiary alkyl ester type acid dissociable group".

(a1-r-2)

[In the formula, $Ra^{t4}$ to $Ra^{t6}$ each independently represent a hydrocarbon group. Here, $Ra^{t5}$ and $Ra^{t6}$ may be bonded to each other to form a ring.]

Examples of the hydrocarbon group as $Ra^{t4}$ include a linear or branched alkyl group, a chain-like or cyclic alkenyl group, and a cyclic hydrocarbon group.

Examples of the linear or branched alkyl group and the cyclic hydrocarbon group (an aliphatic hydrocarbon group which is a monocyclic group, an aliphatic hydrocarbon group which is a polycyclic group, or an aromatic hydrocarbon group) as $Ra^{t4}$ are the same as those exemplified above as $Ra^{t3}$.

As the chain-like or cyclic alkenyl group as $Ra^{t4}$, an alkenyl group having 2 to 10 carbon atoms is preferable.

Examples of the hydrocarbon group as $Ra^{t5}$ or $Ra^{t6}$ are the same as those exemplified above as $Ra^{t3}$.

In a case where $Ra^{t5}$ and $Ra^{t6}$ are bonded to form a ring, suitable examples thereof include a group represented by Formula (a1-r2-1), a group represented by Formula (a1-r2-2), and a group represented by Formula (a1-r2-3).

Meanwhile, $Ra^{t4}$ to $Ra^{t6}$ are not bonded to one another and represent an independent hydrocarbon group, suitable examples thereof include a group represented by Formula (a1-r2-4).

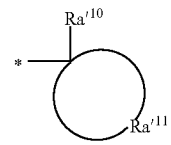

(a1-r2-1)

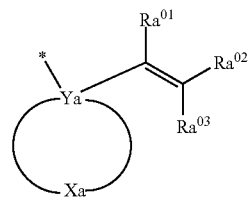

(a1-r2-2)

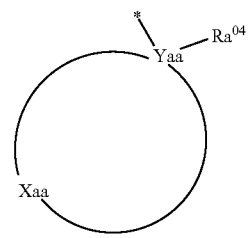

(a1-r2-3)

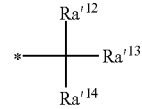

(a1-r2-4)

[In Formula (a1-r2-1), $Ra^{t0}$ represents an alkyl group having 1 to 10 carbon atoms, or a group represented by Formula (a1-r2-r1). $Ra^{t11}$ represents a group that forms an aliphatic cyclic group together with the carbon atom to which $Ra^{t10}$ is bonded. In Formula (a1-r2-2), Ya represents a carbon atom. Xa represents a group that forms a cyclic hydrocarbon group together with Ya. Some or all hydrogen atoms in this cyclic hydrocarbon group may be substituted. $Ra^{01}$ to $Ra^{03}$ each independently represent a hydrogen atom, a chain-like monovalent saturated hydrocarbon group having 1 to 10 carbon atoms, or a monovalent aliphatic cyclic saturated hydrocarbon group having 3 to 20 carbon atoms. Some or all hydrogen atoms in this cyclic saturated hydrocarbon group and the aliphatic cyclic saturated hydrocarbon group may be substituted. Two or more of $Ra^{o1}$ to $Ra^{o3}$ may be bonded to one another to form a cyclic structure. In Formula (a1-r2-3), Yaa represents a carbon atom. Xaa represents a group that forms an aliphatic cyclic group together with Yaa. $Ra^{o4}$ represents an aromatic hydrocarbon group which may have a substituent. In Formula (a1-r2-4), $Ra^{'12}$ and $Ra^{'13}$ each independently represent a chain-like monovalent saturated hydrocarbon group having 1 to 10 carbon atoms or a hydrogen atom. Some or all hydrogen atoms in this chain-like saturated hydrocarbon group may be substituted. $Ra^{'14}$ represents a hydrocarbon group which may have a substituent. The symbol "*" represents a bonding site (the same applies hereinafter).]

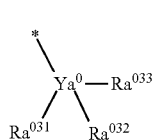

(a1-r2-r1)

[In the formula, $Ya^0$ represents a quaternary carbon atom. $Ra^{o31}$, $Ra^{o32}$, and $Ra^{o33}$ each independently represent a hydrocarbon group which may have a substituent. Here, one or more of $Ra^{o31}$, $Ra^{o32}$, and $Ra^{o33}$ are hydrocarbon groups having at least one polar group.]

In Formula (a1-r2-1), as the alkyl group having 1 to 10 carbon atoms as $Ra^{'10}$, a group exemplified as the linear or branched alkyl group represented by $Ra^{'3}$ in Formula (a1-r-1) is preferable. It is preferable that $Ra^{'10}$ represents an alkyl group having 1 to 5 carbon atoms.

In Formula (a1-r2-r1), $Ya^0$ represents a quaternary carbon atom. That is, there are four adjacent carbon atoms bonded to $Ya^0$ (carbon atom).

In Formula (a1-r2-r1), $Ra^{o31}$, $Ra^{o32}$, and $Ra^{o33}$ each independently represent a hydrocarbon group which may have a substituent. The hydrocarbon groups in $Ra^{o31}$, $Ra^{o32}$, and $Ra^{o33}$ each independently represent a linear or branched alkyl group, a chain-like or cyclic alkenyl group, or a cyclic hydrocarbon group.

The number of carbon atoms of the linear alkyl group as $Ra^{o31}$, $Ra^{o32}$, and $Ra^{o33}$ is preferably in a range of 1 to 5, more preferably in a range of 1 to 4, and still more preferably 1 or 2. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The number of carbon atoms of the branched alkyl group as $Ra^{o31}$, $Ra^{o32}$, and $Ra^{o33}$ is preferably in a range of 3 to 10, and more preferably in a range of 3 to 5. Specific examples thereof include an isopropyl group, an isobutyl group, a tert-butyl group, an isopentyl group, a neopentyl group, a 1,1-diethylpropyl group, a 2,2-dimethylbutyl group and the like. Among these, an isopropyl group is preferable.

As the chain-like or cyclic alkenyl group as $Ra^{o31}$, $Ra^{o32}$, and $Ra^{o33}$, an alkenyl group having 2 to 10 carbon atoms is preferable.

The cyclic hydrocarbon group as $Ra^{o31}$, $Ra^{o32}$, and $Ra^{o33}$ may be an aliphatic hydrocarbon group or an aromatic hydrocarbon group, and may be a polycyclic group or a monocyclic group.

As the aliphatic hydrocarbon group which is a monocyclic group, a group in which one hydrogen atom has been removed from a monocycloalkane is preferable. The monocycloalkane has preferably 3 to 6 carbon atoms, and specific examples thereof include cyclopentane and cyclohexane.

As the aliphatic hydrocarbon group which is a polycyclic group, a group in which one hydrogen atom has been removed from a polycycloalkane is preferable. The polycycloalkane has preferably 7 to 12 carbon atoms, and specific examples thereof include adamantane, norbornane, isobornane, tricyclodecane, tetracyclododecane and the like.

The aromatic hydrocarbon group as $Ra^{o31}$, $Ra^{o32}$, or $Ra^{o33}$ is a hydrocarbon group having at least one aromatic ring. The aromatic ring is not particularly limited as long as it is a cyclic conjugated system having (4n+2) π electrons, and may be monocyclic or polycyclic. The aromatic ring has preferably 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and aromatic heterocyclic rings in which some carbon atoms constituting the above-described aromatic hydrocarbon rings have been substituted with hetero atoms. Examples of the hetero atom in the aromatic heterocyclic rings include an oxygen atom, a sulfur atom, and a nitrogen atom. Specific examples of the aromatic heterocyclic ring include a pyridine ring and a thiophene ring. Specific examples of the aromatic hydrocarbon group include a group in which one hydrogen atom has been removed from the above-described aromatic hydrocarbon ring or aromatic heterocyclic ring (an aryl group or a heteroaryl group); a group in which one hydrogen atom has been removed from an aromatic compound having two or more aromatic rings (for example, biphenyl, fluorene or the like); and a group in which one hydrogen atom of the above-described aromatic hydrocarbon ring or aromatic heterocyclic ring has been substituted with an alkylene group (an arylalkyl group such as a benzyl group, a phenethyl group, a 1-naphthylmethyl group, a 2-naphthylmethyl group, a 1-naphthylethyl group, a 2-naphthylethyl group or the like). The alkylene group which is bonded to the above-described aromatic hydrocarbon ring or aromatic heterocyclic ring has preferably 1 to 4 carbon atoms, more preferably 1 or 2 carbon atoms, and particularly preferably 1 carbon atom.

In a case where the hydrocarbon group represented by $Ra^{o31}$, $Ra^{o32}$, and $Ra^{o33}$ is substituted, examples of substituent include a hydroxy group, a carboxy group, a halogen atom (such as a fluorine atom, a chlorine atom, or a bromine atom), an alkoxy group (such as a methoxy group, an ethoxy group, a propoxy group, or a butoxy group), an alkyloxycarbonyl group and the like.

Among these, the optionally substituted hydrocarbon group as $Ra^{o31}$, $Ra^{o32}$, and $Ra^{o33}$ is preferably a linear or branched alkyl group which may have a substituent. A linear alkyl group is more preferred.

Here, one or more of $Ra^{o31}$, $Ra^{o32}$, and $Ra^{o33}$ are hydrocarbon groups having at least a polar group.

The "hydrocarbon group having a polar group" means that a methylene group ($-CH_2-$) constituting the hydrocarbon group is substituted with a polar group, or at least one hydrogen atom constituting the hydrocarbon group is substituted with a polar group.

As the "hydrocarbon group having a polar group", a functional group represented by Formula (a1-p1) is preferable.

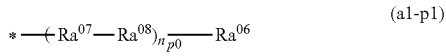
(a1-p1)

[In the formula, $Ra^{07}$ represents a divalent hydrocarbon group having 2 to 12 carbon atoms. $Ra^{08}$ represents a divalent linking group having a hetero atom. $Ra^{06}$ represents a monovalent hydrocarbon group having 1 to 12 carbon atoms.

$n_{p0}$ represents an integer of 1 to 6.]

In Formula (a1-p1), $Ra^{07}$ represents a divalent hydrocarbon group having 2 to 12 carbon atoms.

The number of carbon atoms of $Ra^{07}$ is in a range of 2 to 12, preferably in a range of 2 to 8, more preferably in a range of 2 to 6, still more preferably in a range of 2 to 4, and particularly preferably 2.

The hydrocarbon group as $Ra^{07}$ is preferably a chain-like or cyclic aliphatic hydrocarbon group, and more preferably a chain-like hydrocarbon group.

Examples of $Ra^{07}$ include a linear alkanediyl group such as an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group or the like; a branched alkanediyl group such as a propane-1,2-diyl group, a 1-methylbutane-1,3-diyl group, a 2-methylpropane-1,3-diyl group, a pentane-1,4-diyl group, a 2-methylbutane-1,4-diyl group or the like; a cycloalkanediyl group such as a cyclobutane-1,3-diyl group, a cyclopentane-1,3-diyl group, a cyclohexane-1,4-diyl group, a cyclooctane-1,5-diyl group or the like; a polycyclic divalent alicyclic hydrocarbon group such as a norbornane-1,4-diyl group, a norbornane-2,5-diyl group, an adamantane-1,5-diyl group, an adamantane-2,6-diyl group or the like; and the like.

Among these, an alkanediyl group is preferable, and a linear alkanediyl group is more preferable.

In Formula (a1-p1), $Ra^{08}$ represents a divalent linking group having a hetero atom.

Examples of $Ra^{08}$ includes —O—, —C(=O)—O—, —C(=O)—, —O—C(=O)—O—, —C(=O)—NH—, —NH—, —NH—C(=NH)—, in which H may be substituted with a substituent such as an alkyl group or an acyl group, —S—, —S(=O)$_2$—, —S(=O)$_2$—O— and the like.

Among these, —O—, —C(=O)—O—, —C(=O)—, and —O—C(=O)—O— are preferable from the viewpoint of solubility in a developing solution, —O— and —C(=O)— are particularly preferable.

In Formula (a1-p1), $Ra^{06}$ represents a monovalent hydrocarbon group having 1 to 12 carbon atoms.

The number of carbon atoms of $Ra^{06}$ is in a range of 1 to 12, preferably in a range of 1 to 8, more preferably in a range of 1 to 5, and still more preferably in a range of 1 to 3, particularly preferably 1 or 2, and most preferably 1, from the viewpoint of solubility in a developing solution.

The hydrocarbon group as $Ra^{06}$ includes a chain-like hydrocarbon group or a cyclic hydrocarbon group, or a hydrocarbon group obtained by combining chain-like and cyclic groups.

Examples of the chain-like hydrocarbon group, include a methyl group, an ethyl group, an n-propyl group, an isopropyl group, an n-butyl group, a sec-butyl group, a tert-butyl group, an n-pentyl group, an n-hexyl group, an n-heptyl group, 2-ethylhexyl group, an n-octyl group, an n-nonyl group, an n-decyl group, an n-undecyl group, an n-dodecyl group and the like.

The cyclic hydrocarbon group may be an alicyclic hydrocarbon group or an aromatic hydrocarbon group. The alicyclic hydrocarbon group may be monocyclic or polycyclic.

Examples of the monocyclic alicyclic hydrocarbon group include cycloalkyl groups such as a cyclopropyl group, a cyclobutyl group, a cyclopentyl group, a cyclohexyl group, a methylcyclohexyl group, a dimethylcyclohexyl group, a cycloheptyl group, a cyclooctyl group, a cyclodecyl group and the like. Examples of the polycyclic alicyclic hydrocarbon group include a decahydronaphthyl group, an adamantyl group, a 2-alkyladamantan-2-yl group, a 1-(adamantan-1-yl) alkane-1-yl group, a norbornyl group, a methyl norbornyl group, an isobornyl group and the like.

Examples of the aromatic hydrocarbon group include a phenyl group, a naphthyl group, anthryl group, a p-methylphenyl group, a p-tert-butylphenyl group, a p-adamantylphenyl group, a tolyl group, a xylyl group, a cumenyl group, a mesityl group, a biphenyl group, a phenanthryl group, a 2,6-diethylphenyl group, a 2-methyl-6-ethylphenyl group and the like.

As $Ra^{06}$, a chain-like hydrocarbon group is preferable, an alkyl group is more preferable, and a linear alkyl group is still more preferable, from the viewpoint of solubility in a developing solution.

In Formula (a1-p1), $n_{p0}$ represents an integer of 1 to 6, preferably an integer of 1 to 3, more preferably 1 or 2, and still more preferably 1.

Hereinafter, the specific examples of the hydrocarbon group having at least a polar group are shown.

In the following formulae, * indicates a bond bonded to a quaternary carbon atom ($Ya^0$).

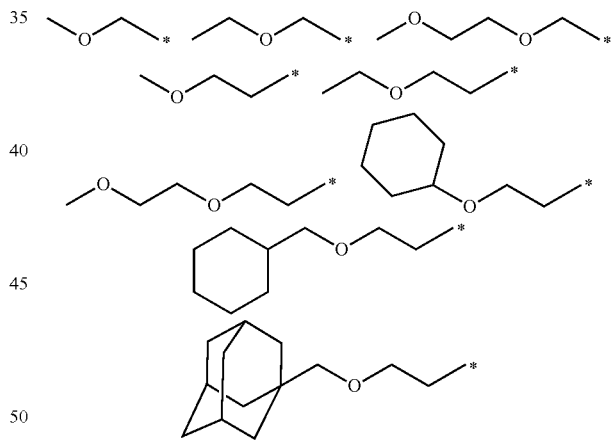

The number of hydrocarbon groups having at least a polar group in Formula (a1-r2-r1) among $Ra^{031}$, $Ra^{032}$ and $Ra^{033}$ is one or more. However, it can be appropriately determined with consideration of the solubility in a developing solution at the time of forming a resist pattern. For example, it is preferable that one or two of $Ra^{031}$, $Ra^{032}$ and $Ra^{033}$ are hydrocarbon groups having at least a polar group, and particularly preferable that one of $Ra^{031}$, $Ra^{032}$ and $Ra^{033}$ is a hydrocarbon group having at least a polar group.

The hydrocarbon group having at least a polar group may have a substituent other than the polar group.

Examples of the substituent include a halogen atom (a fluorine atom, a chlorine atom, a bromine atom and the like), a halogenated alkyl group having 1 to 5 carbon atoms, and the like.

In Formula (a1-r2-1), as $Ra'^{11}$ (the aliphatic cyclic group formed together with the carbon atom to which $Ra'^{10}$ is bonded), a group exemplified as the aliphatic hydrocarbon group which is a monocyclic group or a polycyclic group as $Ra'^{3}$ in Formula (a1-r-1) is preferable.

In Formula (a1-r2-2), as the cyclic hydrocarbon group that is formed by Xa together with Ya, a group formed by further removing one or more hydrogen atoms from the cyclic monovalent hydrocarbon group (such as an aliphatic hydrocarbon group) as $Ra'^{3}$ in Formula (a1-r-1) is exemplified.

The cyclic hydrocarbon group that is formed by Xa together with Ya may have a substituent. Examples of the substituent are the same as those exemplified as the substituents which may be included in the cyclic hydrocarbon group as $Ra'^{3}$.

In Formula (a1-r2-2), examples of the chain-like monovalent saturated hydrocarbon group having 1 to 10 carbon atoms as $Ra^{01}$ to $Ra^{03}$ include a methyl group, an ethyl group, a propyl group, a butyl group, a pentyl group, a hexyl group, a heptyl group, an octyl group, and a decyl group.

Examples of the monovalent aliphatic cyclic saturated hydrocarbon group having 3 to 20 carbon atoms as $Ra^{01}$ to $Ra^{03}$ include a monocyclic aliphatic saturated hydrocarbon group such as a cyclopropyl group, a cyclobutyl group, a cyclopentyl group, a cyclohexyl group, a cycloheptyl group, a cyclooctyl group, a cyclodecyl group, a cyclododecyl group or the like; and a polycyclic aliphatic saturated hydrocarbon group such as a bicyclo[2.2.2]octanyl group, a tricycle[5.2.1.02,6]decanyl group, a tricycle[3.3.1.13,7]decanyl group, a tetracyclo[6.2.1.13,6.02,7]dodecanyl group, an adamantyl group or the like.

From the viewpoint of easily synthesizing a monomer compound from which the constitutional unit (a1) is derived, it is preferable that $Ra^{01}$ to $Ra^{03}$ represents a hydrogen atom or a chain-like monovalent saturated hydrocarbon group having 1 to 10 carbon atoms. Among these, a hydrogen atom, a methyl group, or an ethyl group is more preferable, and a hydrogen atom is particularly preferable.

Examples of the substituent included in the chain-like saturated hydrocarbon group or the aliphatic cyclic saturated hydrocarbon group represented by $Ra^{01}$ to $Ra^{03}$ are the same as those exemplified as $Ra^{05}$.

Examples of the group having a carbon-carbon double bond generated by two or more of $Ra^{01}$ to $Ra^{03}$ being bonded to one another to form a cyclic structure include a cyclopentenyl group, a cyclohexenyl group, a methylcyclopentenyl group, a methylcyclohexenyl group, a cyclopentylidenethenyl group, a cyclohexylidenethenyl group and the like. Among these, from the viewpoint of easily synthesizing a monomer compound from which the constitutional unit (a1) is derived, a cyclopentenyl group, a cyclohexenyl group, or a cyclopentylidenethenyl group is preferable.

In Formula (a1-r2-3), as the aliphatic cyclic group that is formed by Xaa together with Yaa, a group exemplified as the aliphatic hydrocarbon group which is a monocyclic group or a polycyclic group as $Ra'^{3}$ in Formula (a1-r-1) is preferable.

In Formula (a1-r2-3), examples of the aromatic hydrocarbon group as $Ra^{04}$ include a group formed by removing one or more hydrogen atoms from an aromatic hydrocarbon ring having 5 to 30 carbon atoms. Among the examples, $Ra^{04}$ represents preferably a group formed by removing one or more hydrogen atoms from an aromatic hydrocarbon ring having 6 to 15 carbon atoms, more preferably a group formed by removing one or more hydrogen atoms from benzene, naphthalene, anthracene, or phenanthrene, still more preferably a group formed by removing one or more hydrogen atoms from benzene, naphthalene, or anthracene, particularly preferably a group formed by removing one or more hydrogen atoms from benzene or naphthalene, and most preferably a group formed by removing one or more hydrogen atoms from benzene.

Examples of the substituent which may be included in $Ra^{04}$ in Formula (a1-r2-3) include a methyl group, an ethyl group, a propyl group, a hydroxyl group, a carboxyl group, a halogen atom (such as a fluorine atom, a chlorine atom, a bromine atom or the like), an alkoxy group (such as a methoxy group, an ethoxy group, a propoxy group, a butoxy group or the like), an alkyloxycarbonyl group, and the like.

In Formula (a1-r2-4), $Ra'^{12}$ and $Ra'^{13}$ each independently represent a chain-like monovalent saturated hydrocarbon group having 1 to 10 carbon atoms or a hydrogen atom. Examples of the chain-like monovalent saturated hydrocarbon group having 1 to 10 carbon atoms as $Ra'^{12}$ and $Ra'^{13}$ are the same as those exemplified as the chain-like monovalent saturated hydrocarbon group having 1 to 10 carbon atoms as $Ra^{01}$ to $Ra^{03}$. Some or all hydrogen atoms in this chain-like saturated hydrocarbon group may be substituted.

$Ra'^{12}$ and $Ra'^{13}$ represent preferably a hydrogen atom or an alkyl group having 1 to 5 carbon atoms, more preferably an alkyl group having 1 to 5 carbon atoms, still more preferably a methyl group or an ethyl group, and particularly preferably a methyl group.

In a case where the chain-like saturated hydrocarbon group represented by $Ra'^{12}$ and $Ra'^{13}$ is substituted, examples of the substituent are the same as those exemplified as $Ra^{05}$.

In Formula (a1-r2-4), $Ra'^{14}$ represents a hydrocarbon group which may have a substituent. Examples of the hydrocarbon group as $Ra'^{14}$ include a linear or branched alkyl group and a cyclic hydrocarbon group.

The number of carbon atoms of the linear alkyl group as $Ra'^{14}$ is preferably in a range of 1 to 5, more preferably in a range of 1 to 4, and still more preferably 1 or 2. Specific examples thereof include a methyl group, an ethyl group, an n-propyl group, an n-butyl group, and an n-pentyl group. Among these, a methyl group, an ethyl group, or an n-butyl group is preferable, and a methyl group or an ethyl group is more preferable.

The number of carbon atoms of the branched alkyl group as $Ra'^{14}$ is preferably in a range of 3 to 10 and more preferably in a range of 3 to 5. Specific examples thereof include an isopropyl group, an isobutyl group, a tert-butyl group, an isopentyl group, a neopentyl group, a 1,1-diethylpropyl group, a 2,2-dimethylbutyl group and the like. Among these, an isopropyl group is preferable.

In a case where $Ra'^{14}$ represents a cyclic hydrocarbon group, the cyclic hydrocarbon group may be an aliphatic hydrocarbon group or an aromatic hydrocarbon group, and may be a polycyclic group or a monocyclic group.

As the aliphatic hydrocarbon group which is a monocyclic group, a group in which one hydrogen atom has been removed from a monocycloalkane is preferable. The monocycloalkane has preferably 3 to 6 carbon atoms, and specific examples thereof include cyclopentane and cyclohexane.

As the aliphatic hydrocarbon group which is a polycyclic group, a group in which one hydrogen atom has been removed from a polycycloalkane is preferable. The polycycloalkane has preferably 7 to 12 carbon atoms, and specific examples thereof include adamantane, norbornane, isobornane, tricyclodecane, tetracyclododecane and the like.

Examples of the aromatic hydrocarbon group as $Ra'^{14}$ are the same as those exemplified as the aromatic hydrocarbon group as $Ra^{04}$. Among these, $Ra'^{14}$ represents preferably a group formed by removing one or more hydrogen atoms from an aromatic hydrocarbon ring having 6 to 15 carbon atoms, more preferably a group formed by removing one or more hydrogen atoms from benzene, naphthalene, anthracene, or phenanthrene, still more preferably a group formed by removing one or more hydrogen atoms from benzene, naphthalene, or anthracene, particularly preferably a group formed by removing one or more hydrogen atoms from naphthalene or anthracene, and most preferably a group formed by removing one or more hydrogen atoms from naphthalene.

Examples of the substituent which may be included in $Ra'^{14}$ are the same as those exemplified as the substituent which may be included in $Ra^{04}$.

In a case where $Ra'^{14}$ in Formula (a1-r2-4) represents a naphthyl group, the position bonded to the tertiary carbon atom in Formula (a1-r2-4) may be the 1-position or the 2-position of the naphthyl group.

In a case where $Ra'^{14}$ in Formula (a1-r2-4) represents an anthryl group, the position bonded to the tertiary carbon atom in Formula (a1-r2-4) may be the 1-position, the 2-position, or the 9-position of the anthryl group.

Specific examples of the group represented by Formula (a1-r2-1) are shown below.

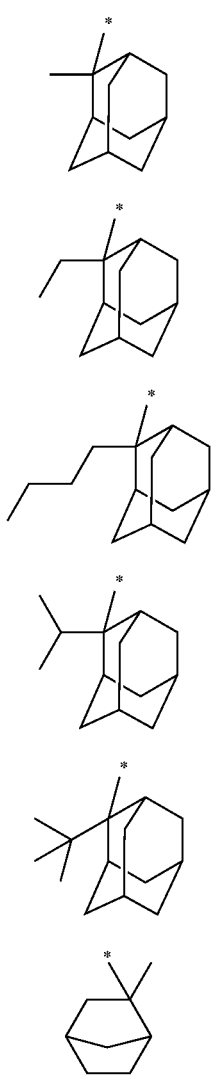
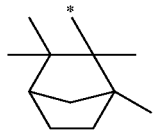
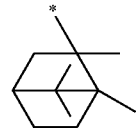
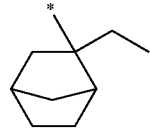
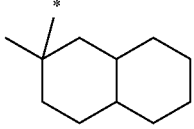
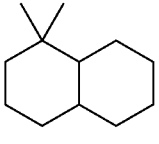
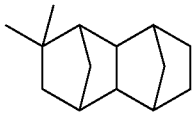
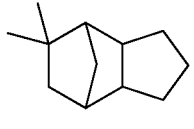
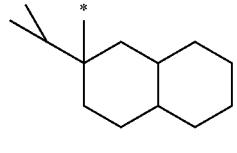
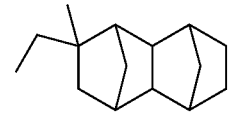

-continued
(r-pr-m17)
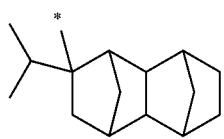
(r-pr-s1)
(r-pr-s2)
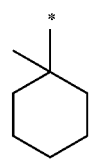
(r-pr-s3)
(r-pr-s4)
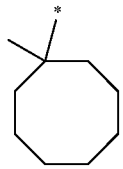
(r-pr-s5)
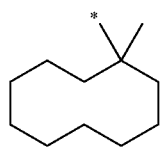
(r-pr-s6)
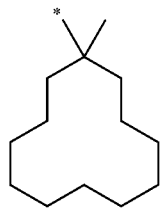
(r-pr-s7)
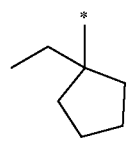
(r-pr-s8)
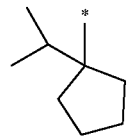
-continued
(r-pr-s9)
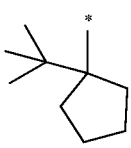
(r-pr-s10)
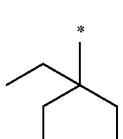
(r-pr-s11)
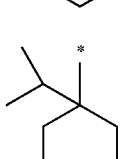
(r-pr-s12)
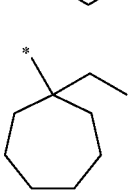
(r-pr-s13)
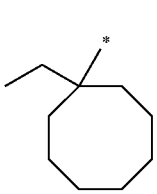
(r-pr-s14)
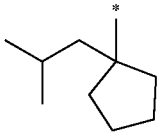
(r-pr-s15)
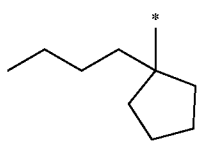
(r-pr-s16)
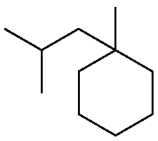
(r-pr-s17)

(r-pr-s18)
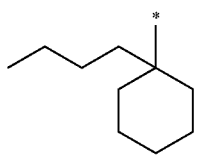
(r-pr-s19)
(r-pr-s20)
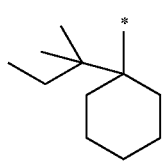
(r-pr-sp1)
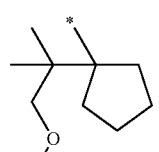
(r-pr-sp2)
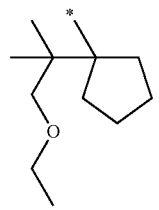
(r-pr-sp3)
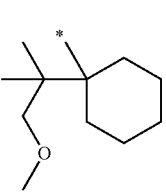
(r-pr-sp4)
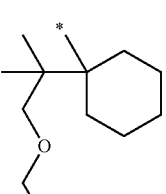
(r-pr-mp1)
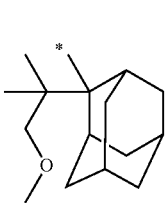
(r-pr-mp2)
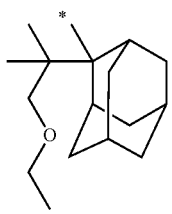
Specific examples of the group represented by Formula (a1-r2-2) are shown below.
(r-pr-sv1)
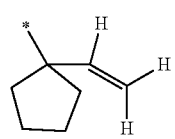
(r-pr-sv2)
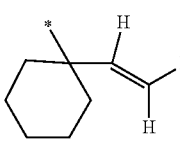
(r-pr-sv3)
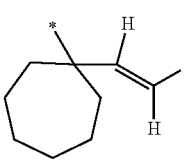
(r-pr-sv4)
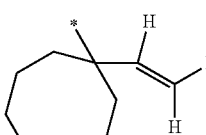
(r-pr-sv5)
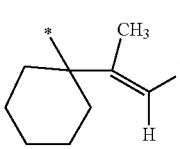
(r-pr-sv6)
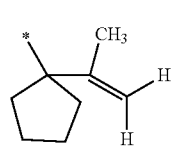
(r-pr-sv7)
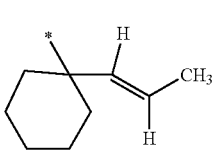
(r-pr-sv8)
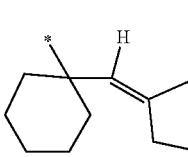

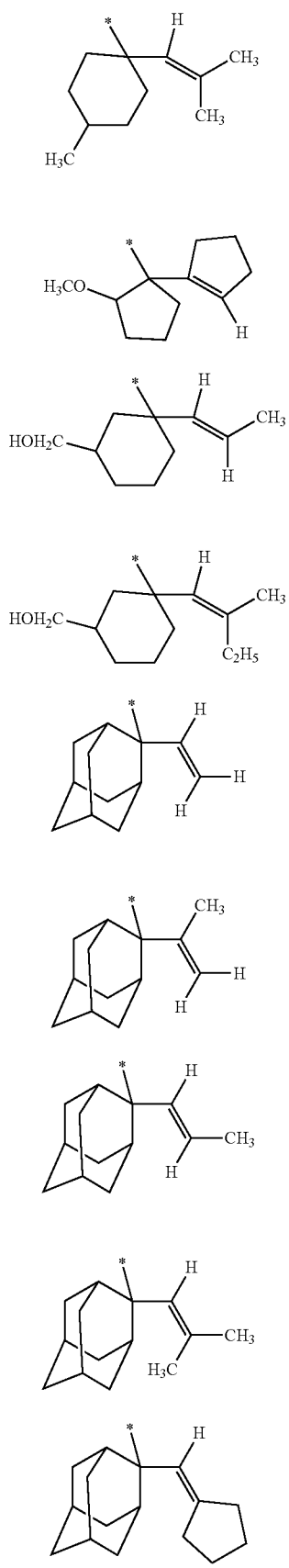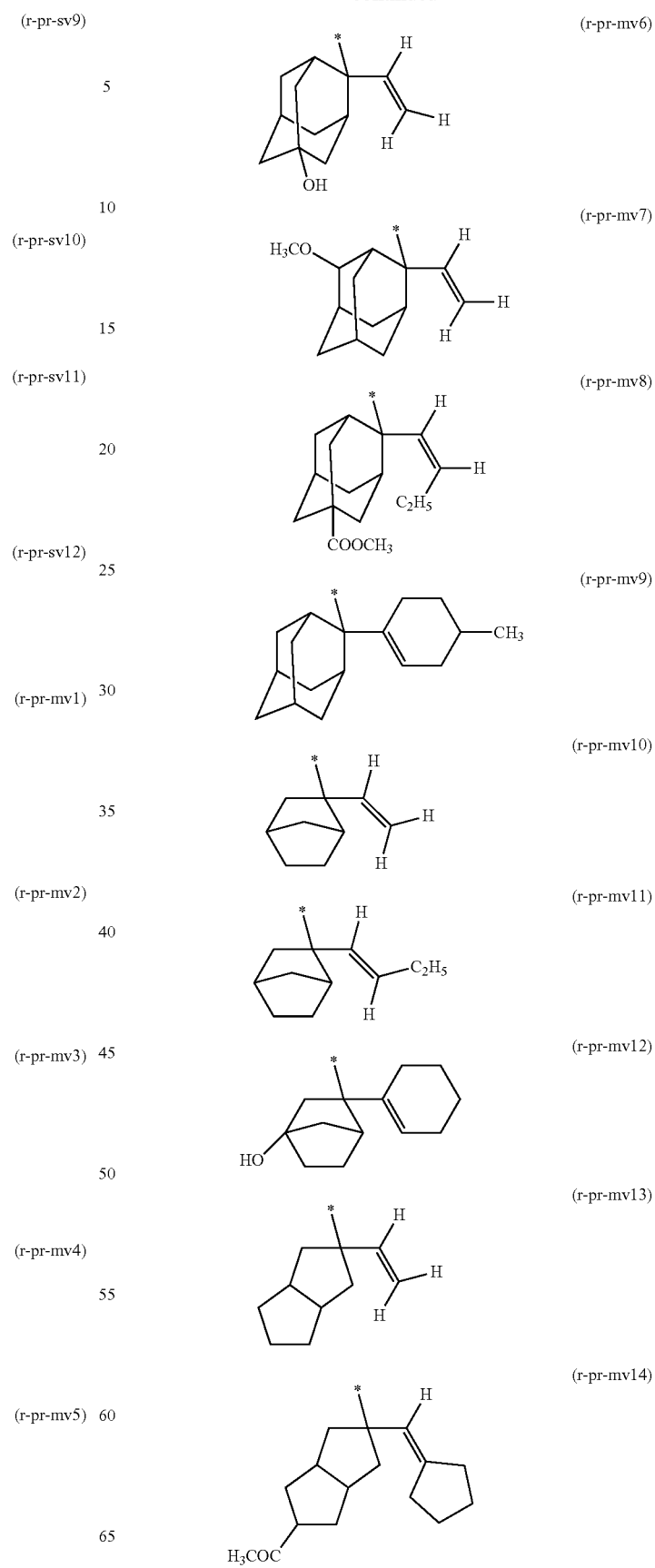

-continued
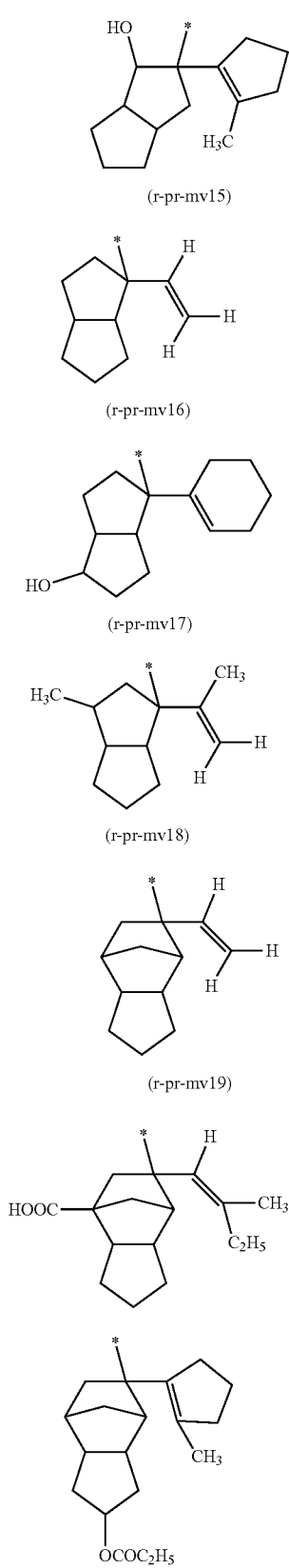
(r-pr-mv15)
(r-pr-mv16)
(r-pr-mv17)
(r-pr-mv18)
(r-pr-mv19)
(r-pr-mv20)
(r-pr-mv21)
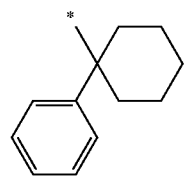
(r-pr-sa1)
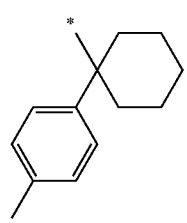
(r-pr-sa2)
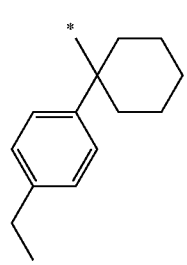
(r-pr-sa3)
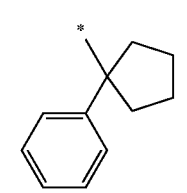
(r-pr-sa4)
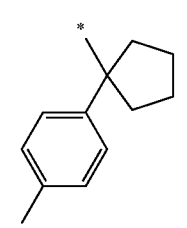
(r-pr-sa5)
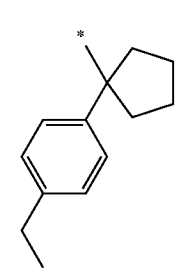
(r-pr-sa6)
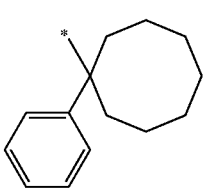
(r-pr-sa7)
Specific examples of the group represented by Formula (a1-r2-3) are shown below.

(r-pr-sa8)
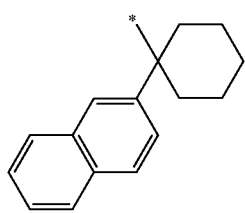
(r-pr-sa9)
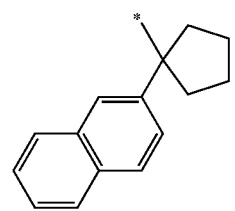
(r-pr-ma1)
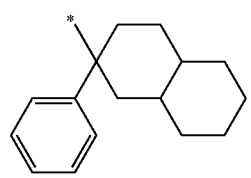
(r-pr-ma2)
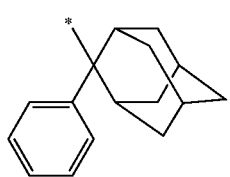
Specific examples of the group represented by Formula (a1-r2-4) are shown below.
(r-pr-cm1)
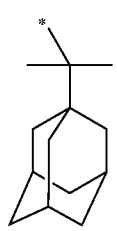
(r-pr-cm2)
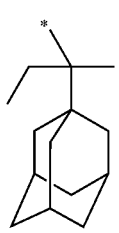
(r-pr-cm3)
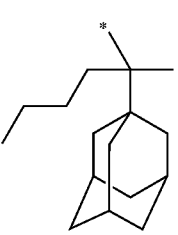
(r-pr-cm4)
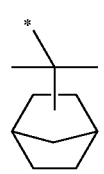
(r-pr-cm5)
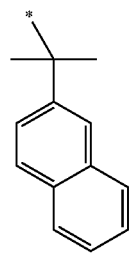
(r-pr-cm6)
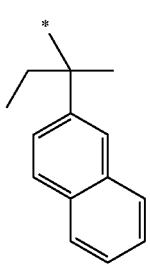
(r-pr-cm7)
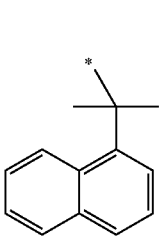
(r-pr-cm8)
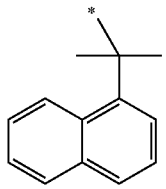
(r-pr-cs1)
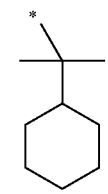
(r-pr-cs2)
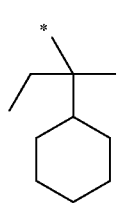

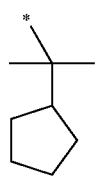 (r-pr-cs3)

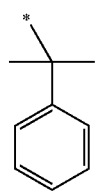 (r-pr-cs4)

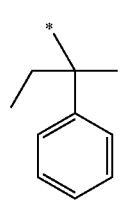 (r-pr-cs5)

 (r-pr-c1)

 (r-pr-c2)

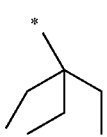 (r-pr-c3)

Tertiary Alkyloxycarbonyl Acid Dissociable Group:

Examples of the acid dissociable group for protecting a hydroxyl group as a polar group include an acid dissociable group (hereinafter, for convenience, also referred to as a "tertiary alkyloxycarbonyl acid dissociable group") represented by Formula (a1-r-3) shown below.

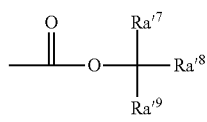 (a1-r-3)

[In the formula, $Ra'^7$ to $Ra'^9$ each represent an alkyl group.]

In Formula (a1-r-3), $Ra'^7$ to $Ra'^9$ each represent preferably an alkyl group having 1 to 5 carbon atoms and more preferably an alkyl group having 1 to 3 carbon atoms.

Furthermore, the total number of carbon atoms in each alkyl group is preferably in a range of 3 to 7, more preferably in a range of 3 to 5, and most preferably 3 or 4.

Examples of the constitutional unit (a1) include a constitutional unit derived from acrylic acid ester in which the hydrogen atom bonded to the carbon atom at the α-position may be substituted with a substituent; a constitutional unit derived from acrylamide; a constitutional unit in which at least some hydrogen atoms in a hydroxyl group of a constitutional unit derived from hydroxystyrene or a hydroxystyrene derivative are protected by a substituent containing the acid decomposable group; and a constitutional unit in which at least some hydrogen atoms in —C(═O)—OH of a constitutional unit derived from vinylbenzoic acid or a vinylbenzoic acid derivative are protected by a substituent containing the acid decomposable group.

Among the examples, as the constitutional unit (a1), a constitutional unit derived from acrylic acid ester in which the hydrogen atom bonded to the carbon atom at the α-position may be substituted with a substituent is preferable.

Specific preferred examples of such a constitutional unit (a1) include constitutional units represented by Formula (a1-1) or (a1-2) shown below.

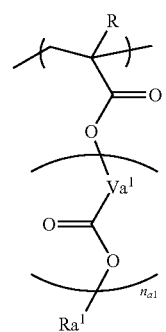 (a1-1)

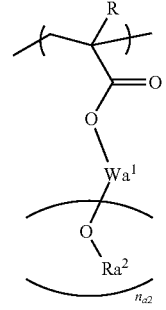 (a1-2)

[In the formula, R represents a hydrogen atom, an alkyl group having 1 to 5 carbon atoms, or a halogenated alkyl group having 1 to 5 carbon atoms. $Va^1$ represents a divalent hydrocarbon group which may contain an ether bond. $n_{a1}$ represents an integer of 0 to 2. $Ra^1$ represents an acid dissociable group represented by Formula (a1-r-1) or (a1-r-2). $Wa^1$ represents a $(n_{a2}+1)$-valent hydrocarbon group, $n_{a2}$ represents an integer of 1 to 3, and $Ra^2$ represents an acid dissociable group represented by Formula (a1-r-1) or (a1-r-3).]

In Formula (a1-1), as the alkyl group having 1 to 5 carbon atoms as R, a linear or branched alkyl group having 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group, and a neopentyl group. The halogenated alkyl group having 1 to 5 carbon atoms is a group in which some or all hydrogen atoms of the alkyl group having 1 to 5 carbon atoms have been substituted with halogen atoms. Examples of the halogen atom include a fluorine atom, a chlorine atom, a bromine atom and an iodine atom, and a fluorine atom is particularly preferable.

R represents preferably a hydrogen atom, an alkyl group having 1 to 5 carbon atoms, or a fluorinated alkyl group having 1 to 5 carbon atoms and most preferably a hydrogen atom or a methyl group from the viewpoint of industrial availability.

In Formula (a1-1), the divalent hydrocarbon group as $Va^1$ may be an aliphatic hydrocarbon group or an aromatic hydrocarbon group.

The aliphatic hydrocarbon group as the divalent hydrocarbon group represented by $Va^1$ may be saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof.

The linear aliphatic hydrocarbon group has preferably 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—CH$_2$—], an ethylene group [—(CH$_2$)$_2$—], a trimethylene group [—(CH$_2$)$_3$—], a tetramethylene group [—(CH$_2$)$_4$—], and a pentamethylene group [—(CH$_2$)$_5$—].

The branched aliphatic hydrocarbon group has preferably 2 to 10 carbon atoms, more preferably 3 to 6 carbon atoms, still more preferably 3 or 4 carbon atoms, and most preferably 3 carbon atoms.

As the branched aliphatic hydrocarbon group, a branched alkylene group is preferred, and specific examples thereof include alkylalkylene groups, for example, alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group in the alkylalkylene group, a linear alkyl group having 1 to 5 carbon atoms is preferable.

Examples of the aliphatic hydrocarbon group containing a ring in the structure thereof include an alicyclic hydrocarbon group (a group in which two hydrogen atoms have been removed from an aliphatic hydrocarbon ring), a group in which the alicyclic hydrocarbon group is bonded to the terminal of the linear or branched aliphatic hydrocarbon group, and a group in which the alicyclic hydrocarbon group is interposed in the linear or branched aliphatic hydrocarbon group. The linear or branched aliphatic hydrocarbon group is the same as defined for the above-described linear aliphatic hydrocarbon group or the above-described branched aliphatic hydrocarbon group.

The alicyclic hydrocarbon group has preferably 3 to 20 carbon atoms and more preferably 3 to 12 carbon atoms.

The alicyclic hydrocarbon group may be monocyclic or polycyclic. As the monocyclic alicyclic hydrocarbon group, a group in which two hydrogen atoms have been removed from a monocycloalkane is preferable. The monocycloalkane has preferably 3 to 6 carbon atoms, and specific examples thereof include cyclopentane and cyclohexane. As the polycyclic alicyclic hydrocarbon group, a group in which two hydrogen atoms have been removed from a polycycloalkane is preferable. The polycycloalkane has preferably 7 to 12 carbon atoms, and specific examples thereof the polycycloalkane include adamantane, norbornane, isobornane, tricyclodecane, and tetracyclododecane.

The aromatic hydrocarbon group as the divalent hydrocarbon group represented by $Va^1$ is a hydrocarbon group having an aromatic ring.

The aromatic hydrocarbon group has preferably 3 to 30 carbon atoms, more preferably 5 to 30 carbon atoms, still more preferably 5 to 20 carbon atoms, particularly preferably 6 to 15 carbon atoms, and most preferably 6 to 12 carbon atoms. Here, the number of carbon atoms in a substituent is not included in the number of carbon atoms.

Specific examples of the aromatic ring contained in the aromatic hydrocarbon group include aromatic hydrocarbon rings such as benzene, biphenyl, fluorene, naphthalene, anthracene, and phenanthrene; and aromatic heterocyclic rings in which some carbon atoms constituting the above-described aromatic hydrocarbon rings have been substituted with hetero atoms. Examples of the hetero atom in the aromatic heterocyclic rings include an oxygen atom, a sulfur atom, and a nitrogen atom.

Specific examples of the aromatic hydrocarbon group include a group in which two hydrogen atoms have been removed from the above-described aromatic hydrocarbon ring (an arylene group); and a group in which one hydrogen atom of a group (an aryl group) formed by removing one hydrogen atom from the aromatic hydrocarbon ring has been substituted with an alkylene group (a group formed by removing one more hydrogen atom from an aryl group in an arylalkyl group such as a benzyl group, a phenethyl group, a 1-naphthylmethyl group, a 2-naphthylmethyl group, a 1-naphthylethyl group, or a 2-naphthylethyl group). The alkylene group (an alkyl chain in the arylalkyl group) has preferably 1 to 4 carbon atoms, more preferably 1 or 2 carbon atoms, and particularly preferably 1 carbon atom.

In Formula (a1-1), $Ra^1$ represents an acid dissociable group represented by Formula (a1-r-1) or (a1-r-2).

In Formula (a1-2), the ($n_{a2}$+1)-valent hydrocarbon group as $Wa^1$ may be an aliphatic hydrocarbon group or an aromatic hydrocarbon group. The aliphatic hydrocarbon group indicates a hydrocarbon group that has no aromaticity, and may be saturated or unsaturated, but is preferably saturated in general. Examples of the aliphatic hydrocarbon group include a linear or branched aliphatic hydrocarbon group, an aliphatic hydrocarbon group containing a ring in the structure thereof, and a combination of the linear or branched aliphatic hydrocarbon group and the aliphatic hydrocarbon group containing a ring in the structure thereof.

The valency of $n_{a2}$+1 is preferably divalent, trivalent or tetravalent, and divalent or trivalent is more preferable.

In Formula (a1-2), $Ra^2$ represents an acid dissociable group represented by Formula (a1-r-1) or (a1-r-3).

Specific examples of the constitutional unit represented by Formula (a1-1) are shown below. In the formulae shown below, $R^\alpha$ represents a hydrogen atom, a methyl group, or a trifluoromethyl group.

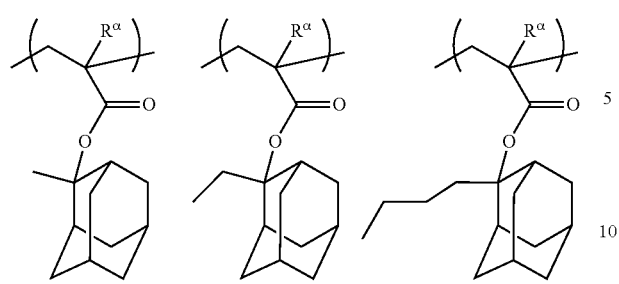
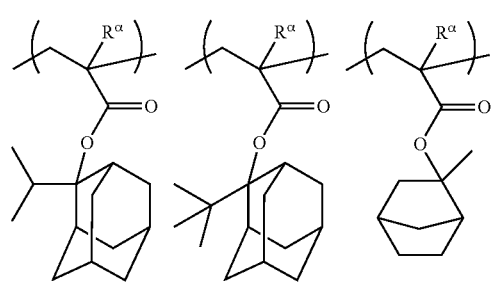
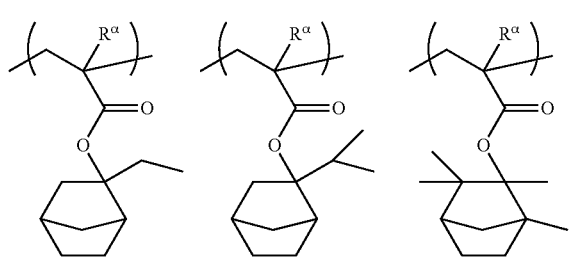
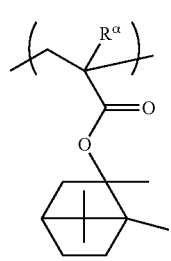
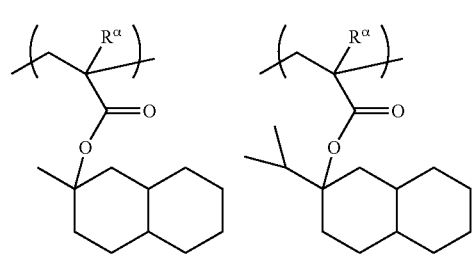
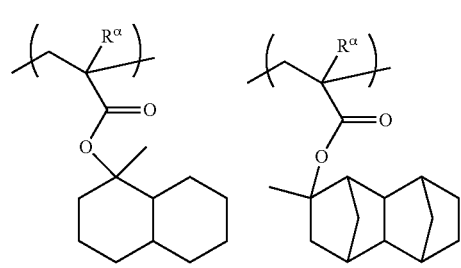
-continued
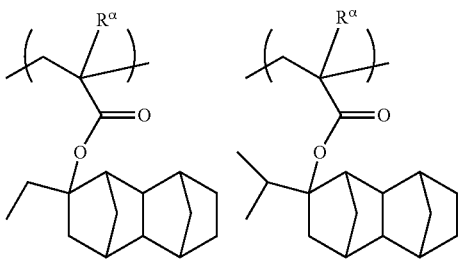
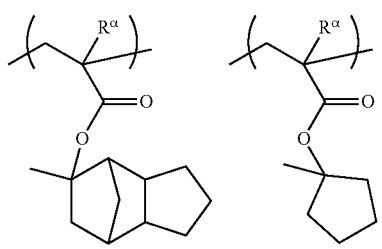
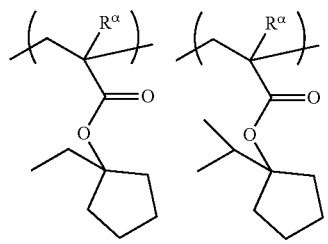
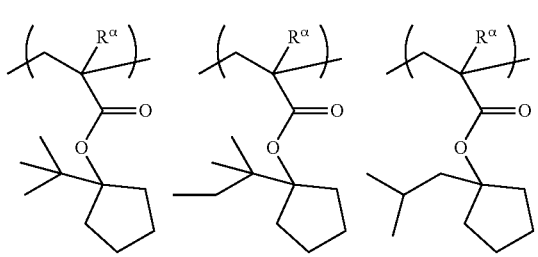
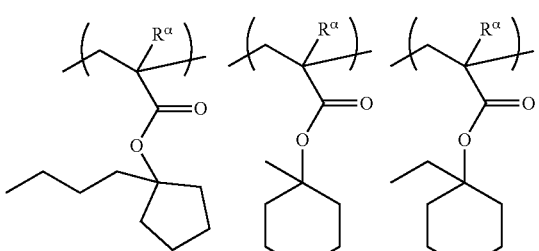
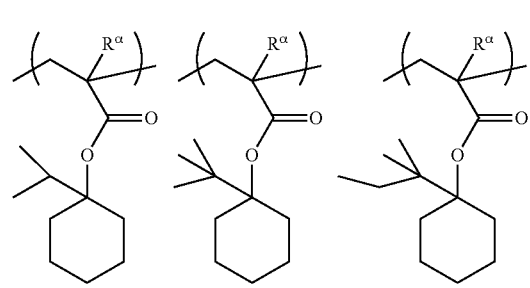

-continued
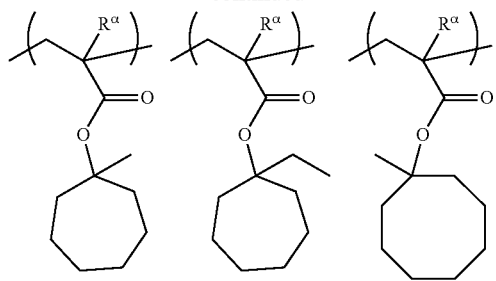
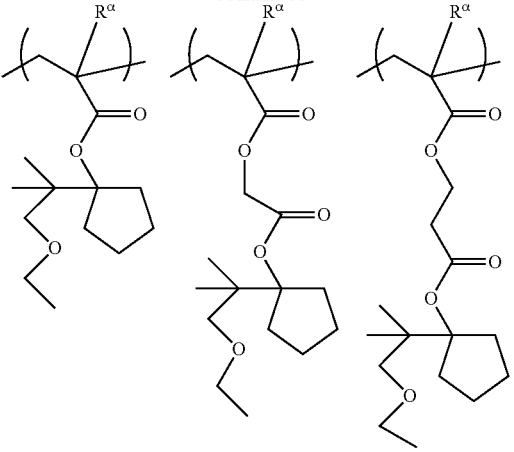
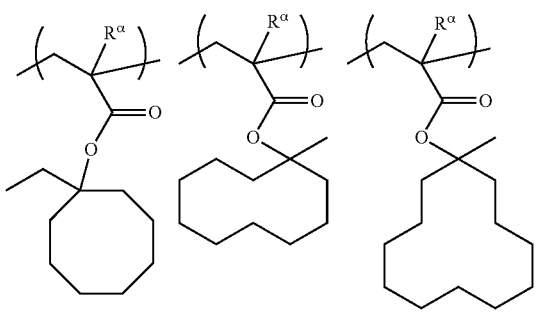
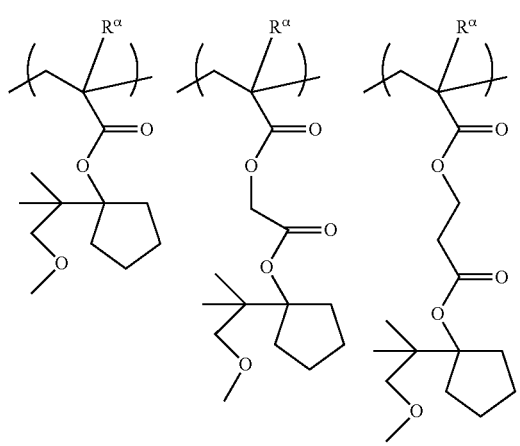
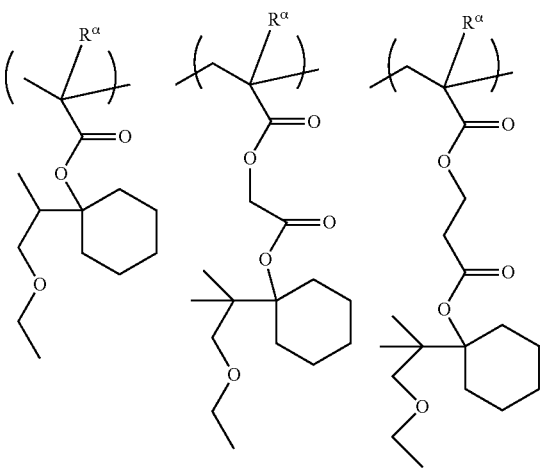
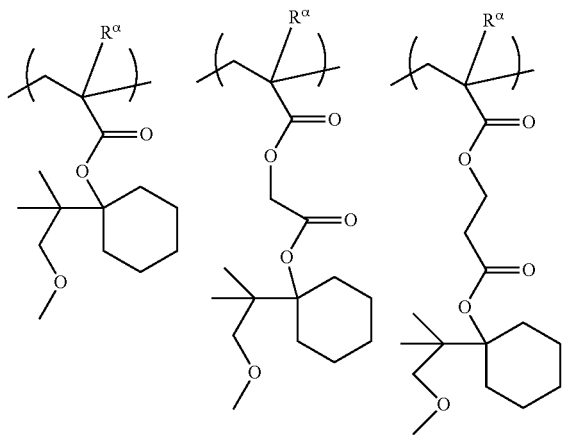
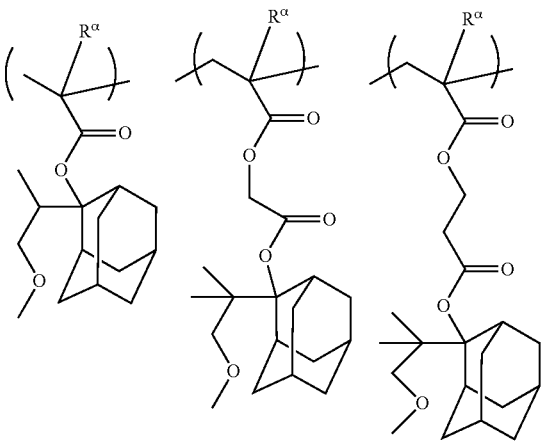

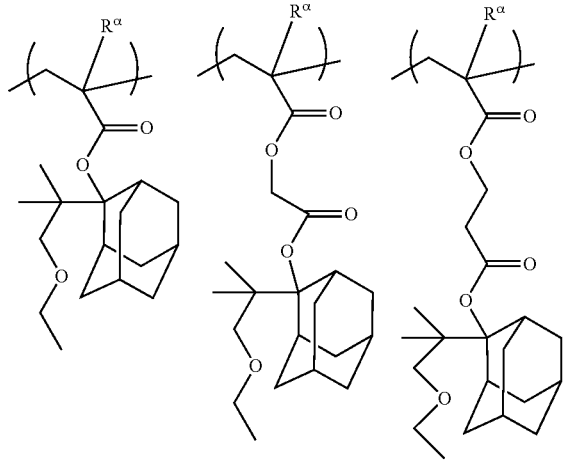
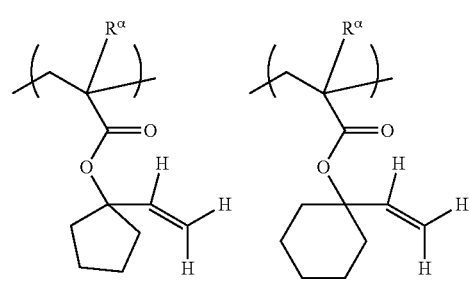
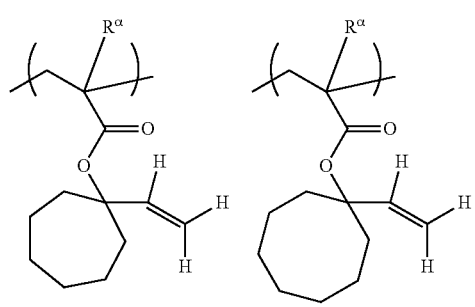
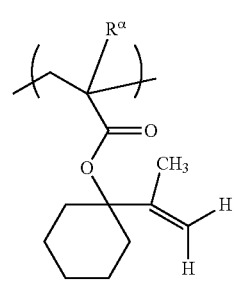
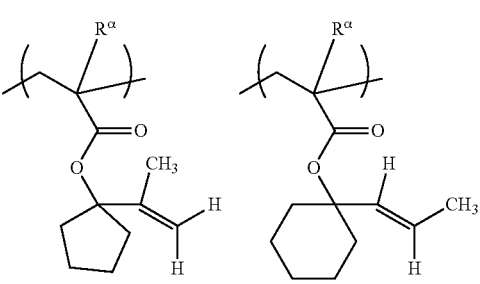
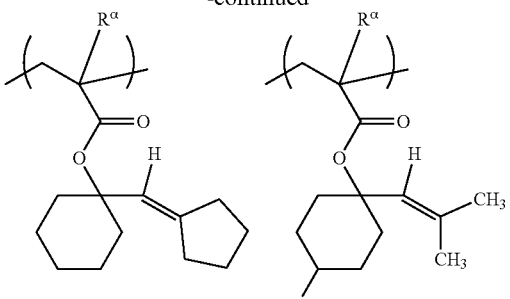
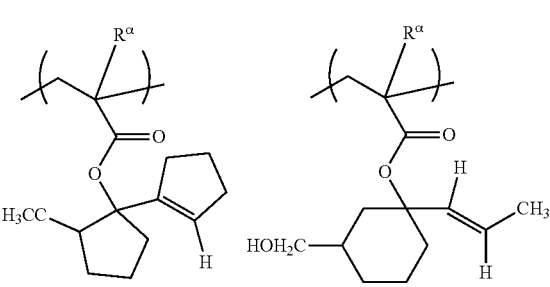
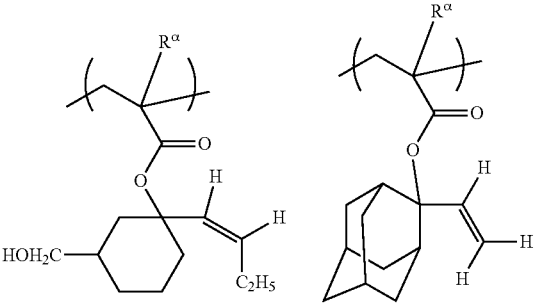
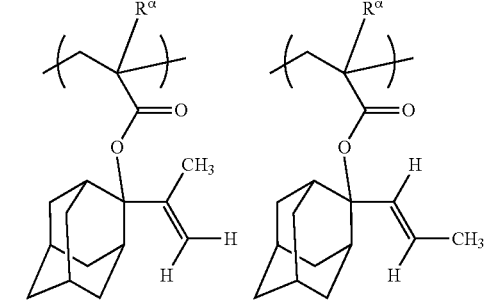
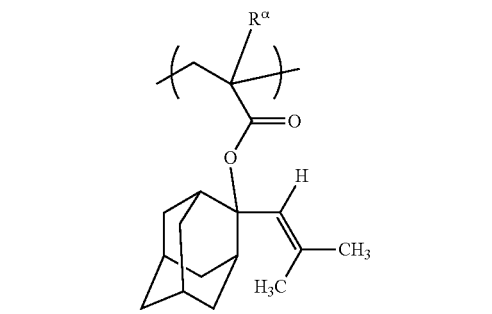

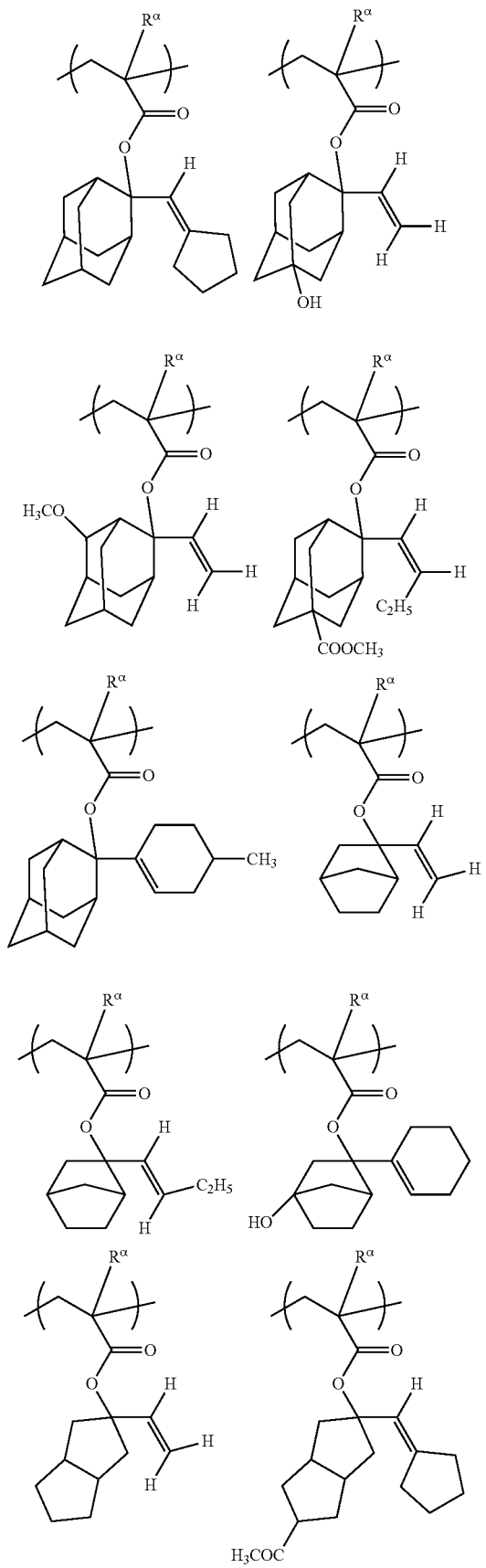
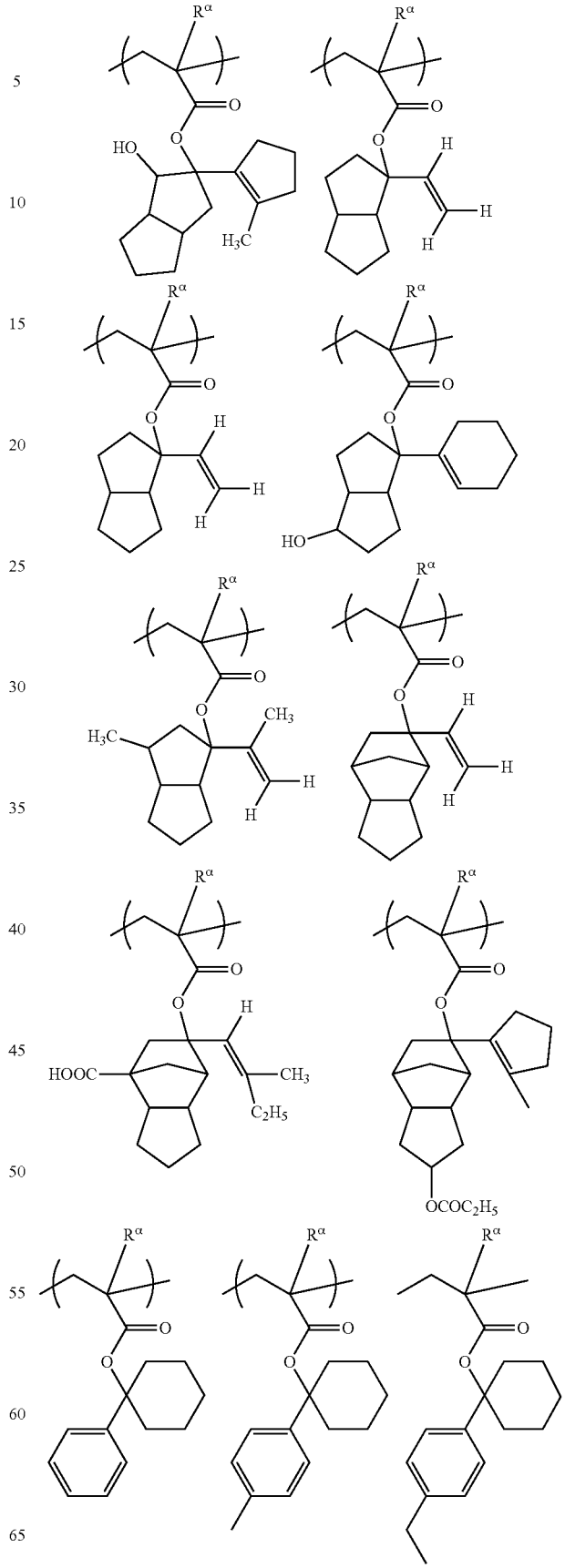

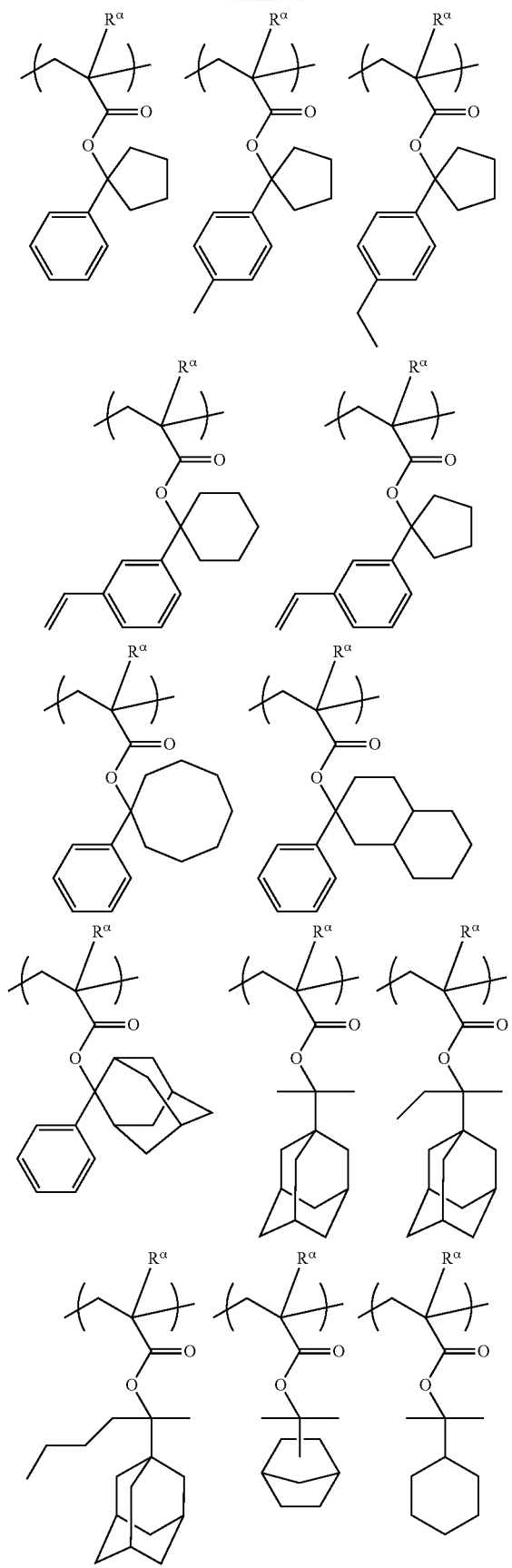
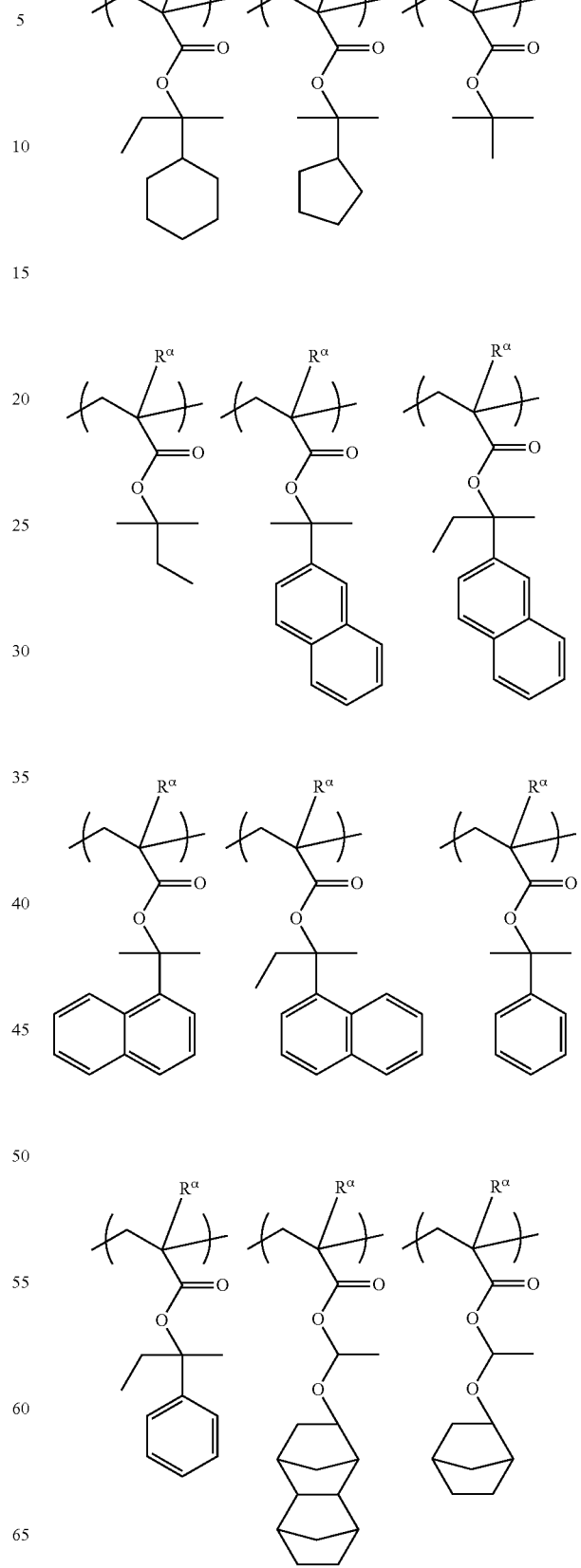

-continued
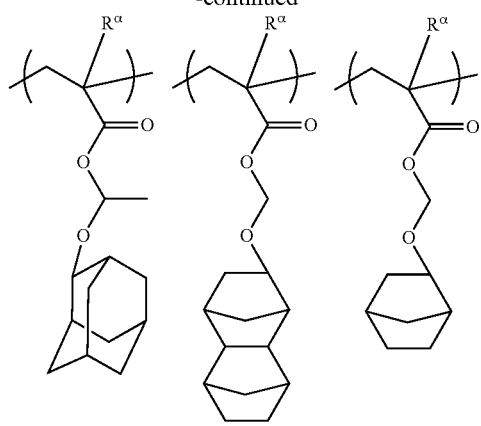
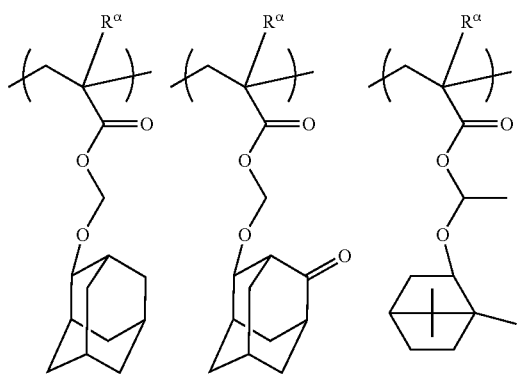
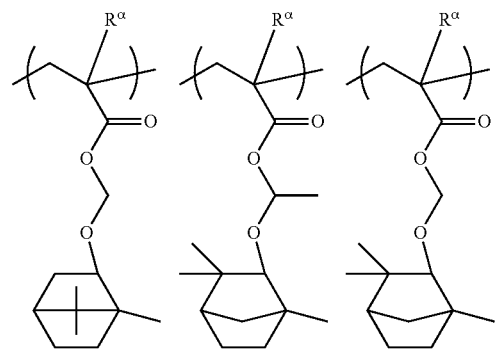
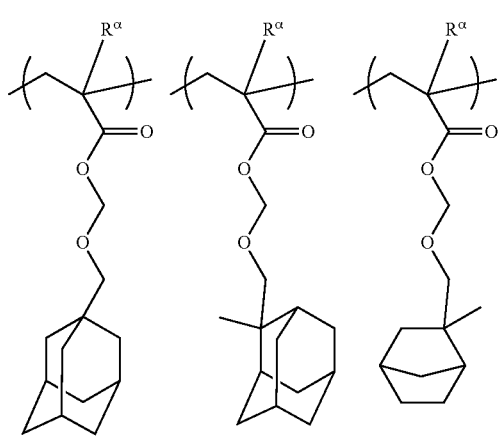
-continued
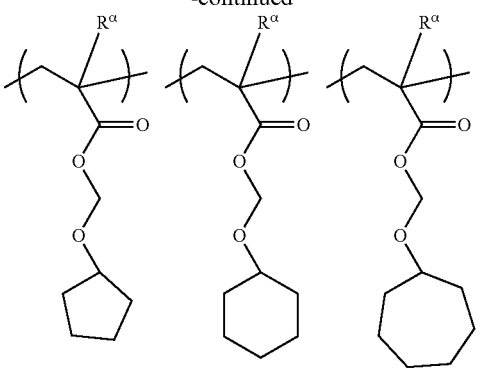
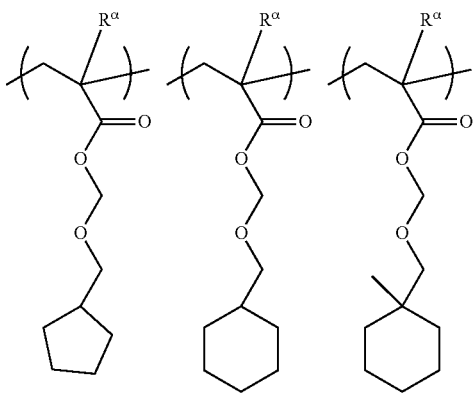
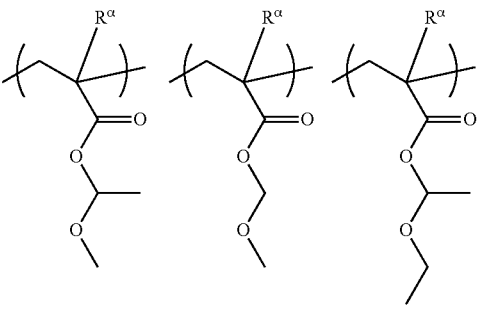
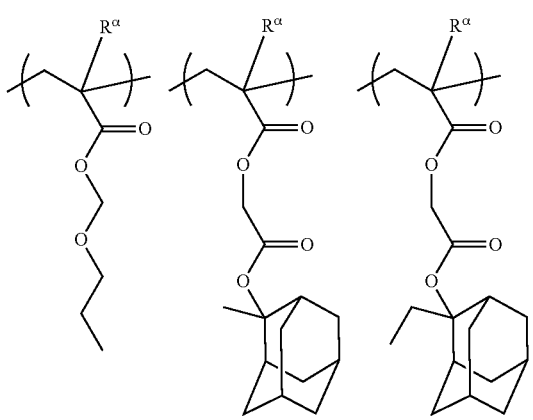

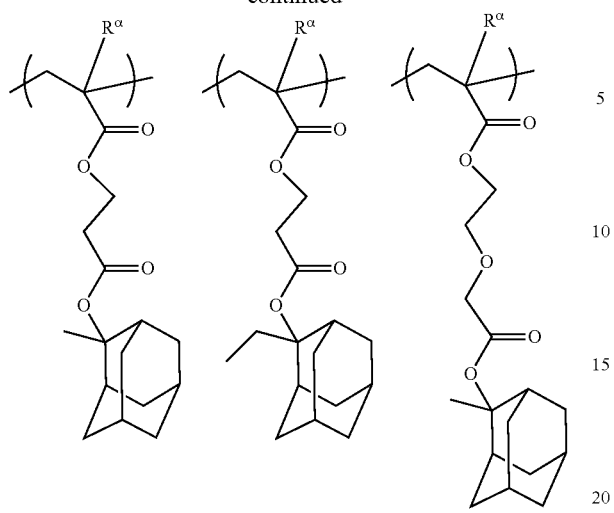
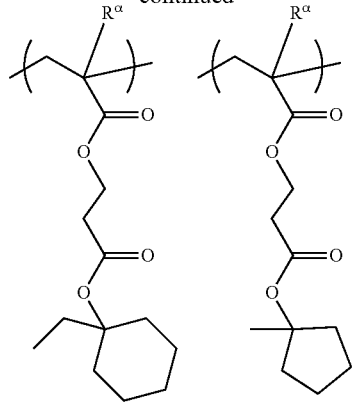
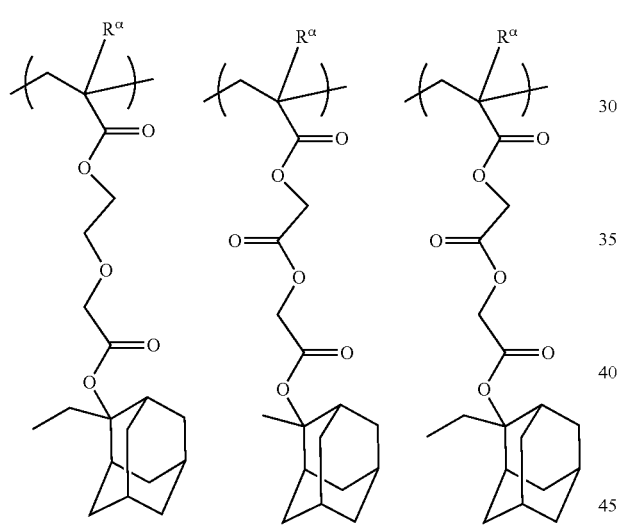
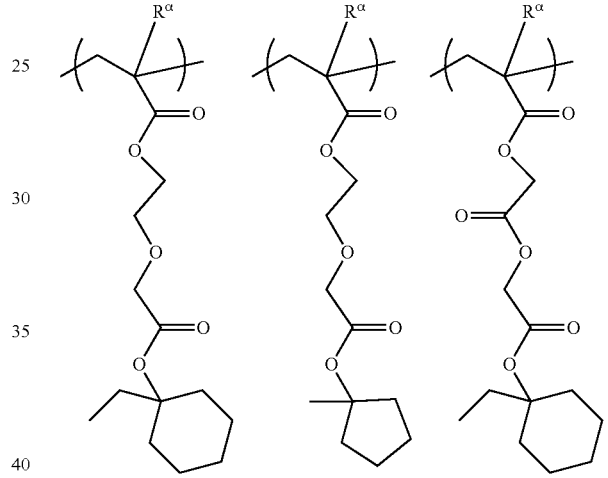
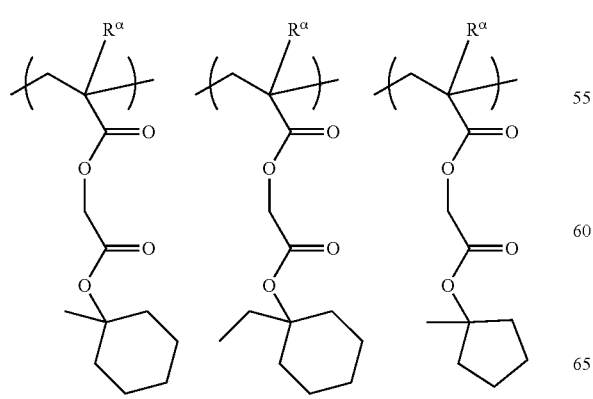
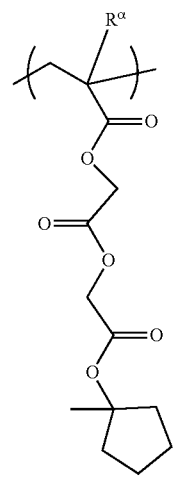
Specific examples of the constitutional unit represented by Formula (a1-2) are shown below.

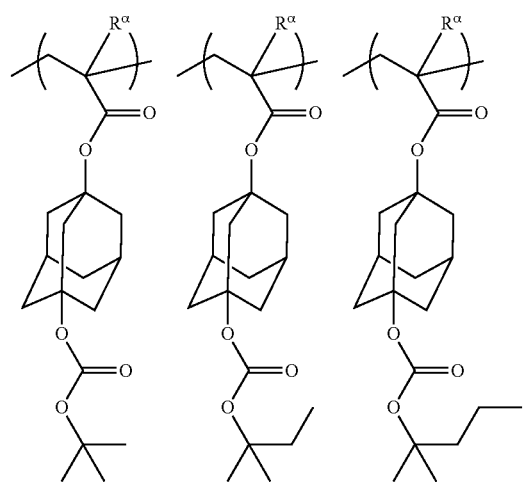
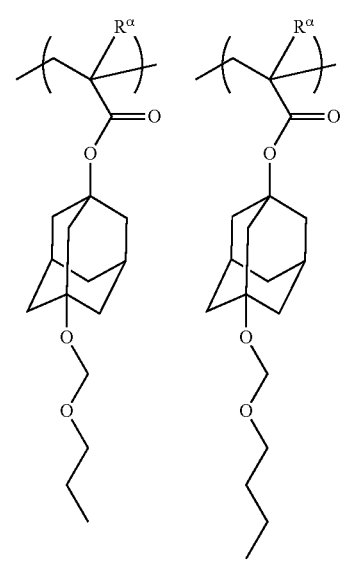
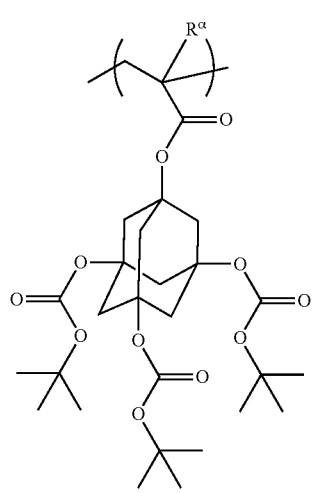
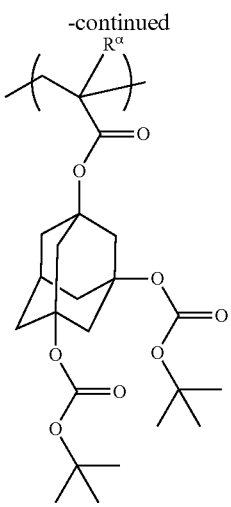
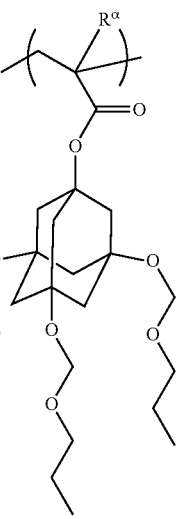
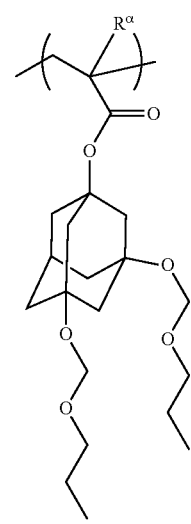
The constitutional unit (a1) in the component (A1) may be used alone or two or more kinds thereof.
As the constitutional unit (a1), the constitutional unit represented by Formula (a1-1) is more preferable since the characteristics (sensitivity, shape and the like) in lithography by electron beam or EUV are easily enhanced.

Among these, as the constitutional unit (a1), particularly preferred is one containing a constitutional unit represented by Formula (a1-1-1).

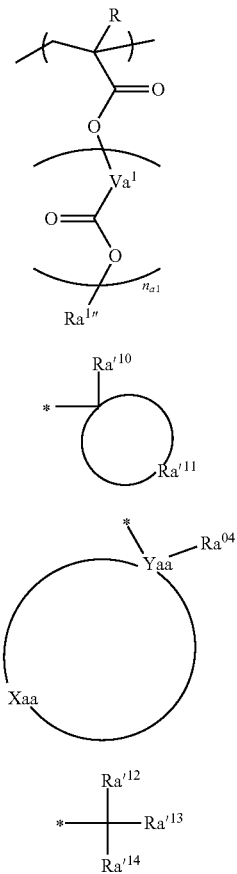

(a1-1-1)

(a1-r2-1)

(a1-r2-3)

(a1-r2-4)

[In the formulae, $Ra^{1\prime\prime}$ represents an acid dissociable group represented by Formula (a1-r2-1), (a1-r2-3) or (a1-r2-4).]

In Formula (a1-1-1), R, $Va^1$ and $n_{a1}$ are the same as R, $Va^1$ and $n_{a1}$ defined in Formula (a1-1).

The acid dissociable group represented by Formula (a1-r2-1), (a1-r2-3) or (a1-r2-4) is defined as described above.

$Ra^{1\prime\prime}$ in Formula (a1-1-1) is preferably an acid dissociable group represented by (a1-r2-1) or (a1-r2-3) among them. Further, in Formula (a1-r2-1), $Ra'^{11}$ (the aliphatic cyclic group formed together with the carbon atom to which $Ra'^{10}$ is bonded) is preferably an aliphatic monocyclic group, and specific examples thereof include those described as the aliphatic monocyclic groups as $Ra'^{3}$ in Formula (a1-r-1). In Formula (a1-r2-3), the aliphatic cyclic group formed by Xaa together with Yaa is preferably an aliphatic monocyclic group, and specific examples thereof include those described as the aliphatic monocyclic groups as $Ra'^{3}$ in Formula (a1-r-1).

The proportion of the constitutional unit (a1) in the component (A1) is preferably in a range of 5% to 80% by mole, more preferably in a range of 10% to 75% by mole, and still more preferably in a range of 30% to 70% by mole with respect to the total amount (100% by mole) of all constitutional units constituting the component (A1).

By setting the proportion of the constitutional unit (a1) to be greater than or equal to the lower limit of the above-described preferable range, lithography characteristics such as sensitivity, resolution, and roughness can be improved. On the other hand, when the proportion thereof is lower than or equal to the upper limit of the preferable range, the balance with other constitutional units can be easily taken, and various lithography characteristics are enhanced.

<<Constitutional Unit (a10) Containing Hydroxystyrene Skeleton>>

It is preferable that the component (A1) further has a constitutional unit (a10) containing a hydroxystyrene skeleton, in addition to the constitutional unit (a1).

The constitutional unit (a10) is suitably, for example, a constitutional unit represented by Formula (a10-1).

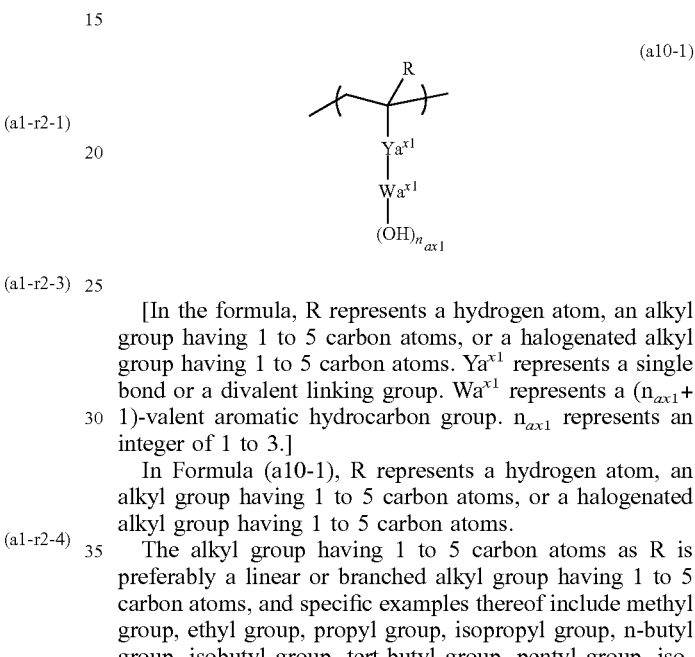

(a10-1)

[In the formula, R represents a hydrogen atom, an alkyl group having 1 to 5 carbon atoms, or a halogenated alkyl group having 1 to 5 carbon atoms. $Ya^{x1}$ represents a single bond or a divalent linking group. $Wa^{x1}$ represents a ($n_{ax1}$+1)-valent aromatic hydrocarbon group. $n_{ax1}$ represents an integer of 1 to 3.]

In Formula (a10-1), R represents a hydrogen atom, an alkyl group having 1 to 5 carbon atoms, or a halogenated alkyl group having 1 to 5 carbon atoms.

The alkyl group having 1 to 5 carbon atoms as R is preferably a linear or branched alkyl group having 1 to 5 carbon atoms, and specific examples thereof include methyl group, ethyl group, propyl group, isopropyl group, n-butyl group, isobutyl group, tert-butyl group, pentyl group, isopentyl group, neopentyl group and the like. The halogenated alkyl group having 1 to 5 carbon atoms as R is a group in which some or all hydrogen atoms of the above-described alkyl group having 1 to 5 carbon atoms have been substituted with halogen atoms. Examples of the halogen atom include a fluorine atom, a chlorine atom, a bromine atom and an iodine atom, and a fluorine atom is particularly preferable.

R represents preferably a hydrogen atom, an alkyl group having 1 to 5 carbon atoms, or a fluorinated alkyl group having 1 to 5 carbon atoms and most preferably a hydrogen atom or a methyl group from the viewpoint of industrial availability.

In Formula (a10-1), $Ya^{x1}$ represents a single bond or a divalent linking group.

Suitable examples of the divalent linking group as $Ya^{x1}$ include a divalent hydrocarbon group which may have a substituent and a divalent linking group having hetero atoms.

Divalent Hydrocarbon Group which May have Substituent:

In a case where $Ya^{x1}$ represents a divalent hydrocarbon group which may have a substituent, the hydrocarbon group may be an aliphatic hydrocarbon group or an aromatic hydrocarbon group.

Aliphatic Hydrocarbon Group as $Ya^{x1}$

The aliphatic hydrocarbon group indicates a hydrocarbon group that has no aromaticity. The aliphatic hydrocarbon group may be saturated or unsaturated. In general, the aliphatic hydrocarbon group is preferably saturated.

Examples of the aliphatic hydrocarbon group include a linear or branched aliphatic hydrocarbon group, and an aliphatic hydrocarbon group containing a ring in the structure thereof.

Linear or Branched Aliphatic Hydrocarbon Group

The linear aliphatic hydrocarbon group has preferably 1 to 10 carbon atoms, more preferably 1 to 6 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group has preferably 2 to 10 carbon atoms, more preferably 3 to 6 carbon atoms, still more preferably 3 or 4 carbon atoms, and most preferably 3 carbon atoms.

As the branched aliphatic hydrocarbon group, a branched alkylene group is preferred, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group in the alkylalkylene group, a linear alkyl group having 1 to 5 carbon atoms is preferable.

The linear or branched aliphatic hydrocarbon group may or may not have a substituent. Examples of the substituent include a fluorine atom, a fluorinated alkyl group having 1 to 5 carbon atoms which has been substituted with a fluorine atom, and a carbonyl group.

Aliphatic Hydrocarbon Group Containing Ring in Structure Thereof

Examples of the aliphatic hydrocarbon group containing a ring in the structure thereof include a cyclic aliphatic hydrocarbon group which may have a substituent containing a hetero atom in the ring structure thereof (a group in which two hydrogen atoms have been removed from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group is interposed in a linear or branched aliphatic hydrocarbon group. As the linear or branched aliphatic hydrocarbon group, the same groups as those described above can be used.

The cyclic aliphatic hydrocarbon group has preferably 3 to 20 carbon atoms and more preferably 3 to 12 carbon atoms.

The cyclic aliphatic hydrocarbon group may be a polycyclic group or a monocyclic group. As the monocyclic alicyclic hydrocarbon group, a group in which two hydrogen atoms have been removed from a monocycloalkane is preferable. The monocycloalkane has preferably 3 to 6 carbon atoms, and specific examples thereof include cyclopentane and cyclohexane. As the polycyclic alicyclic hydrocarbon group, a group in which two hydrogen atoms have been removed from a polycycloalkane is preferable. As the polycycloalkane, a group having 7 to 12 carbon atoms is preferable. Examples of the polycycloalkane include adamantane, norbornane, isobornane, tricyclodecane, and tetracyclododecane.

The cyclic aliphatic hydrocarbon group may or may not have a substituent. Examples of the substituent include an alkyl group, an alkoxy group, a halogen atom, a halogenated alkyl group, a hydroxyl group, a carbonyl group, and the like.

The alkyl group as the substituent is preferably an alkyl group having 1 to 5 carbon atoms, and a methyl group, an ethyl group, a propyl group, an n-butyl group, a tert-butyl group or the like is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, a tert-butoxy group or the like, and most preferably a methoxy group or an ethoxy group.

Examples of the halogen atom as the substituent include a fluorine atom, a chlorine atom, a bromine atom, an iodine atom and the like, and a fluorine atom is preferable.

Examples of the halogenated alkyl group as the substituent include groups in which some or all hydrogen atoms in the above-described alkyl groups have been substituted with the above-described halogen atoms.

In the cyclic aliphatic hydrocarbon group, some carbon atoms constituting the ring structure thereof may be substituted with a substituent containing a hetero atom. As the substituent containing a hetero atom, —O—, —C(=O)—O—, —S—, —S(=O)$_2$—, or —S(=O)$_2$—O— is preferable.

Aromatic Hydrocarbon Group as $Y_a^{x1}$

The aromatic hydrocarbon group is a hydrocarbon group having at least one aromatic ring.

The aromatic ring is not particularly limited as long as it is a cyclic conjugated system having (4n+2) π electrons, and may be monocyclic or polycyclic. The aromatic ring has preferably 5 to 30 carbon atoms, more preferably 5 to 20 carbon atoms, still more preferably 6 to 15 carbon atoms, and particularly preferably 6 to 12 carbon atoms. Here, the number of carbon atoms in a substituent is not included in the number of carbon atoms. Specific examples of the aromatic ring include aromatic hydrocarbon rings such as benzene, naphthalene, anthracene, and phenanthrene; and aromatic heterocyclic rings in which some carbon atoms constituting the above-described aromatic hydrocarbon rings have been substituted with hetero atoms. Examples of the hetero atom in the aromatic heterocyclic rings include an oxygen atom, a sulfur atom, and a nitrogen atom. Specific examples of the aromatic heterocyclic ring include a pyridine ring and a thiophene ring.

Specific examples of the aromatic hydrocarbon group include a group in which two hydrogen atoms have been removed from the above-described aromatic hydrocarbon ring or aromatic heterocyclic ring (an arylene group or a heteroarylene group); a group in which two hydrogen atoms have been removed from an aromatic compound having two or more aromatic rings (biphenyl, fluorene or the like); a group in which one hydrogen atom of a group (an aryl group or a heteroaryl group) obtained by removing one hydrogen atom from the above-described aromatic hydrocarbon ring or aromatic heterocyclic ring has been substituted with an alkylene group (a group in which one hydrogen atom has been further removed from the aryl group in the arylalkyl group such as a benzyl group, a phenethyl group, a 1-naphthylmethyl group, a 2-naphthylmethyl group, a 1-naphthylethyl group, or a 2-naphthylethyl group), and the like. The alkylene group which is bonded to the above-described aryl group or heteroaryl group has preferably 1 to 4 carbon atoms, more preferably 1 or 2 carbon atoms, and particularly preferably 1 carbon atom.

With respect to the aromatic hydrocarbon group, the hydrogen atom in the aromatic hydrocarbon group may be substituted with a substituent. For example, the hydrogen atom bonded to the aromatic ring in the aromatic hydrocarbon group may be substituted with a substituent. Examples of substituents include an alkyl group, an alkoxy group, a halogen atom, a halogenated alkyl group, and a hydroxyl group.

The alkyl group as the substituent is preferably an alkyl group having 1 to 5 carbon atoms, and a methyl group, an ethyl group, a propyl group, an n-butyl group, a tert-butyl group or the like is most preferable.

As the alkoxy group, the halogen atom, and the halogenated alkyl group as the substituents, the same groups as the above-described substituent groups for substituting a hydrogen atom in the cyclic aliphatic hydrocarbon group can be exemplified.

Divalent Linking Group Containing Hetero Atom:

In a case where $Ya^{x1}$ represents a divalent linking group containing a hetero atom, preferred examples of the linking group include —O—, —C(=O)—O—, —C(=O)—, —O—C(=O)—O—, —C(=O)—NH—, —NH—, —NH—C(=NH)—, in which H may be substituted with a substituent such as an alkyl group, an acyl group, or the like, —S—, —S(=O)$_2$—, —S(=O)$_2$—O—, and a group represented by Formula: —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$— [in the formulae, Y$^{21}$ and Y$^{22}$ each independently represent a divalent hydrocarbon group which may have a substituent, O represents an oxygen atom, and m'' represents an integer of 0 to 3].

In a case where the divalent linking group containing a hetero atom is —C(=O)—NH—, —C(=O)—NH—C(=O)—, —NH— or —NH—C(=NH)—, in which H may be substituted with a substituent such as an alkyl group, an acyl group, or the like. The substituent (an alkyl group, an acyl group, or the like) has preferably 1 to 10 carbon atoms, more preferably 1 to 8 carbon atoms, and particularly preferably 1 to 5 carbon atoms.

In Formulae —Y$^{21}$—O—Y$^{22}$—, —Y$^{21}$—O—, —Y$^{21}$—C(=O)—O—, —C(=O)—O—Y$^{21}$—, —[Y$^{21}$—C(=O)—O]$_{m''}$—Y$^{22}$—, —Y$^{21}$—O—C(=O)—Y$^{22}$— or —Y$^{21}$—S(=O)$_2$—O—Y$^{22}$—, Y$^{21}$ and Y$^{22}$ each independently represent a divalent hydrocarbon group which may have a substituent. Examples of the divalent hydrocarbon group include the same groups as those described above as the "divalent hydrocarbon group which may have a substituent" in the explanation of the above-described divalent linking group.

As Y$^{21}$, a linear aliphatic hydrocarbon group is preferable, a linear alkylene group is more preferable, a linear alkylene group having 1 to 5 carbon atoms is still more preferable, and a methylene group or an ethylene group is particularly preferable.

As Y$^{22}$, a linear or branched aliphatic hydrocarbon group is preferable, and a methylene group, an ethylene group, or an alkylmethylene group is more preferable. The alkyl group in the alkylmethylene group is preferably a linear alkyl group having 1 to 5 carbon atoms, more preferably a linear alkyl group having 1 to 3 carbon atoms, and most preferably a methyl group.

In the group represented by Formula —[Y$^{21}$—C(=O)—O]$_{m''}$—Y$^{22}$—, m'' represents an integer of 0 to 3, preferably an integer of 0 to 2, more preferably 0 or 1, and particularly preferably 1. In other words, it is particularly preferable that the group represented by Formula —[Y$^{21}$—C(=O)—O]$_{m''}$—Y$^{22}$— is a group represented by Formula —Y$^{21}$—C(=O)—O—Y$^{22}$—. Among these, a group represented by Formula —(CH$_2$)$_{a'}$—C(=O)—O—(CH$_2$)$_{b'}$— is preferable. In the formula, a' represents an integer of 1 to 10, preferably an integer of 1 to 8, more preferably an integer of 1 to 5, still more preferably 1 or 2, and most preferably 1. b' represents an integer of 1 to 10, preferably an integer of 1 to 8, more preferably an integer of 1 to 5, still more preferably 1 or 2, and most preferably 1.

As Ya$^{x1}$, a single bond, an ester bond [—C(=O)—O—], an ether bond (—O—), —C(=O)—NH—, a linear or branched alkylene group, or a combination of these is preferable, and among these, a single bond is particularly preferable.

In Formula (a10-1), Wa$^{x1}$ represents a ($n_{ax1}$+1)-valent aromatic hydrocarbon group.

Examples of the aromatic hydrocarbon group as Wa$^{x1}$ include groups in which ($n_{ax1}$+1) hydrogen atoms have been removed from an aromatic ring. The aromatic ring is not particularly limited as long as it is a cyclic conjugated system having (4n+2) π electrons, and may be monocyclic or polycyclic. The aromatic ring has preferably 5 to 30 carbon atoms, more preferably 5 to 20 carbon atoms, still more preferably 6 to 15 carbon atoms, and particularly preferably 6 to 12 carbon atoms. Specific examples of the aromatic ring include aromatic hydrocarbon rings such as benzene, naphthalene, anthracene, and phenanthrene; and aromatic heterocyclic rings in which some carbon atoms constituting the above-described aromatic hydrocarbon rings have been substituted with hetero atoms. Examples of the hetero atom in the aromatic heterocyclic rings include an oxygen atom, a sulfur atom, and a nitrogen atom. Specific examples of the aromatic heterocyclic ring include a pyridine ring and a thiophene ring.

In Formula (a10-1), $n_{ax1}$ represents an integer of 1 to 3, preferably 1 or 2, and more preferably 1.

Specific examples of the constitutional unit represented by Formula (a10-1) are shown below.

In each formula, Ra represents a hydrogen atom, a methyl group, or a trifluoromethyl group.

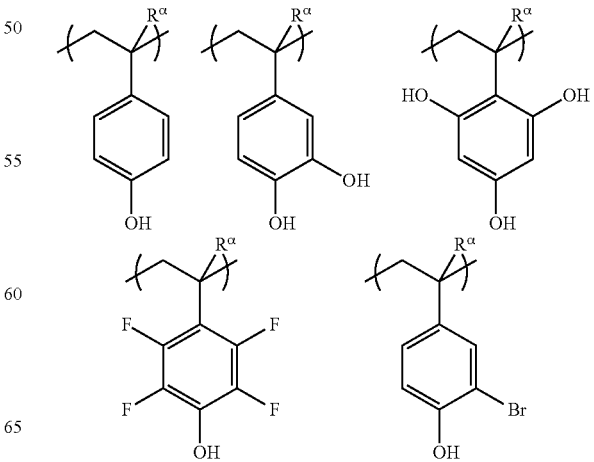

-continued

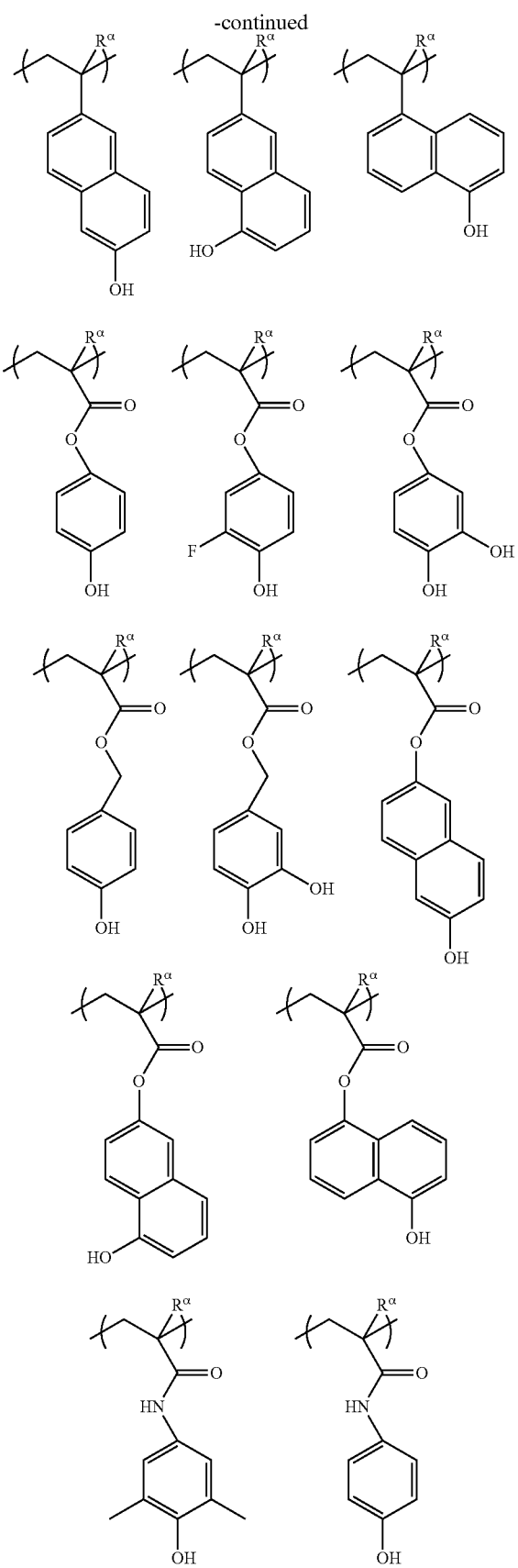

The constitutional unit (a10) included in the component (A1) may be used alone or two or more kinds thereof.

The proportion of the constitutional unit (a10) in the component (A1) is, for example, in a range of 0% to 80% by mole, preferably in a range of 10% to 80% by mole, more preferably in a range of 20% to 70% by mole, and particularly preferably in a range of 30% to 60% by mole with respect to the total amount (100% by mole) of all constitutional units constituting the component (A1).

By setting the proportion of the constitutional unit (a10) to be greater than or equal to the lower limit of the above-described preferable range, lithography characteristics such as sensitivity, resolution, and roughness can be improved. On the other hand, when the proportion thereof is lower than or equal to the upper limit of the preferable range, the balance with other constitutional units can be easily taken, and various lithography characteristics are enhanced.

<<Constitutional Unit (a2)>>

It is preferable that the component (A1) has a constitutional unit (a2) (here, a constitutional unit corresponding to the constitutional unit (a1) is excluded) containing a lactone-containing cyclic group, a —SO₂-containing cyclic group, or a carbonate-containing cyclic group, in addition to the constitutional unit (a1).

In a case where the component (A1) is used for forming a resist film, the lactone-containing cyclic group, the —SO₂-containing cyclic group, or the carbonate-containing cyclic group in the constitutional unit (a2) is effective for improving the adhesiveness of the resist film to the substrate. Additionally, as the constitutional unit (a2) is contained, for example, the acid diffusion length is appropriately adjusted, the adhesion of the resist film to the substrate is enhanced, the solubility during development is appropriately adjusted, and the etching resistance is improved. Therefore, the lithography characteristics are enhanced.

The term "lactone-containing cyclic group" indicates a cyclic group that contains a ring (lactone ring) containing a —O—C(=O)— in the ring structure. In a case where the lactone ring is counted as the first ring and the group contains only the lactone ring, the group is referred to as a monocyclic group. Further, in a case where the group has other ring structures, the group is referred to as a polycyclic group regardless of the structures. The lactone-containing cyclic group may be a monocyclic group or a polycyclic group.

The lactone-containing cyclic group for the constitutional unit (a2) is not particularly limited, and an optional constitutional unit may be used. Specific examples thereof include groups represented by Formulae (a2-r-1) to (a2-r-7) shown below.

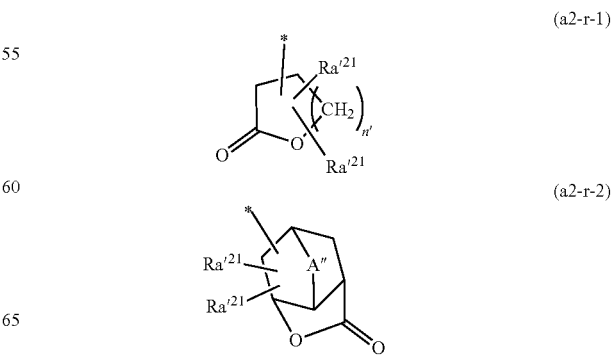

-continued

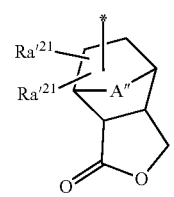 (a2-r-3)

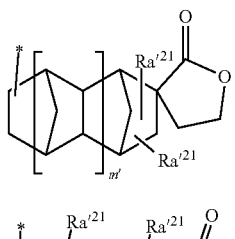 (a2-r-4)

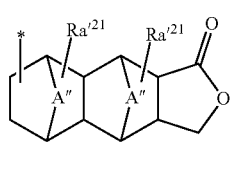 (a2-r-5)

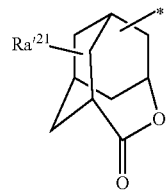 (a2-r-6)

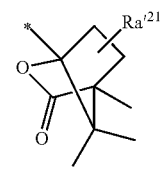 (a2-r-7)

[In the formulae, each $Ra'^{21}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group; and R" represents a hydrogen atom, an alkyl group, a lactone-containing cyclic group, a carbonate-containing cyclic group, or a —SO$_2$-containing cyclic group; A" represents an oxygen atom (—O—), a sulfur atom (—S—) or an alkylene group having 1 to 5 carbon atoms which may contain an oxygen atom or a sulfur atom; n' represents an integer of 0 to 2; and m' represents 0 or 1.]

In Formulae (a2-r-1) to (a2-r-7), the alkyl group as $Ra'^{21}$ is preferably an alkyl group having 1 to 6 carbon atoms. Further, the alkyl group is preferably a linear alkyl group or a branched alkyl group. Specific examples thereof include a methyl group, an ethyl group, a propyl group, an isopropyl group, an n-butyl group, an isobutyl group, a tert-butyl group, a pentyl group, an isopentyl group, a neopentyl group, a hexyl group and the like. Among these, a methyl group or ethyl group is preferable, and a methyl group is particularly preferable.

The alkoxy group as $Ra'^{21}$ is preferably an alkoxy group having 1 to 6 carbon atoms.

Further, the alkoxy group is preferably a linear alkoxy group or a branched alkoxy group. Specific examples of the alkoxy groups include a group formed by linking the above-described alkyl group as $Ra'^{21}$ to an oxygen atom (—O—).

Examples of the halogen atom as $Ra'^{21}$ include a fluorine atom, a chlorine atom, a bromine atom, and an iodine atom. Among these, a fluorine atom is preferable.

Examples of the halogenated alkyl group as $Ra'^{21}$ include groups in which some or all hydrogen atoms in the above-described alkyl group as $Ra'^{21}$ have been substituted with the above-described halogen atoms. As the halogenated alkyl group, a fluorinated alkyl group is preferable, and a perfluoroalkyl group is particularly preferable.

In —COOR" and —OC(=O)R" as $Ra'^{21}$, R" represents a hydrogen atom, an alkyl group, a lactone-containing cyclic group, a carbonate-containing cyclic group, or a —SO$_2$-containing cyclic group.

The alkyl group as R" may be linear, branched, or cyclic, and preferably has 1 to 15 carbon atoms.

In a case where R" represents a linear or branched alkyl group, it is preferably an alkyl group having 1 to 10 carbon atoms, more preferably an alkyl group having 1 to 5 carbon atoms, and particularly preferably a methyl group or an ethyl group.

In a case where R" represents a cyclic alkyl group, the number of carbon atoms thereof is preferably in a range of 3 to 15, more preferably in a range of 4 to 12, and most preferably in a range of 5 to 10. Specific examples thereof include groups in which one or more hydrogen atoms have been removed from a monocycloalkane, which may or may not be substituted with a fluorine atom or a fluorinated alkyl group; and groups in which one or more hydrogen atoms have been removed from a polycycloalkane such as bicycloalkane, tricycloalkane, or tetracycloalkane. More specific examples thereof include groups in which one or more hydrogen atoms have been removed from a monocycloalkane such as cyclopentane or cyclohexane; groups in which one or more hydrogen atoms have been removed from a polycycloalkane such as adamantane, norbornane, isobornane, tricyclodecane, or tetracyclododecane; and the like.

Examples of the lactone-containing cyclic group as R" include those exemplified as the groups represented by Formulae (a2-r-1) to (a2-r-7).

The carbonate-containing cyclic group as R" has the same definition as that for the carbonate-containing cyclic group described below. Specific examples of the carbonate-containing cyclic group include groups represented by Formulae (ax3-r-1) to (ax3-r-3).

The —SO$_2$-containing cyclic group as R" has the same definition as that for the —SO$_2$-containing cyclic group described below. Specific examples of the —SO$_2$-containing cyclic group include groups represented by Formulae (a5-r-1) to (a5-r-4).

The hydroxyalkyl group as $Ra'^{21}$ has preferably 1 to 6 carbon atoms, and specific examples thereof include a group in which at least one hydrogen atom in the alkyl group as $Ra'^{21}$ has been substituted with a hydroxyl group.

In Formulae (a2-r-2), (a2-r-3) and (a2-r-5), as the alkylene group having 1 to 5 carbon atoms as A", a linear or branched alkylene group is preferable, and examples thereof include a methylene group, an ethylene group, an n-propylene group, an isopropylene group and the like. Specific examples of alkylene groups that contain an oxygen atom or a sulfur atom include groups in which —O— or —S— is interposed in the terminal of the alkylene group or between the carbon atoms of the alkylene group, and examples thereof include —O—CH$_2$—, —CH$_2$—O—CH$_2$—, —S—CH$_2$—, and —CH$_2$—S—CH$_2$—. As A", an alkylene group having 1 to 5 carbon atoms or —O— is preferable, an alkylene group having 1 to 5 carbon atoms is more preferable, and a methylene group is most preferable.

Specific examples of the groups represented by Formulae (a2-r-1) to (a2-r-7) are shown below.
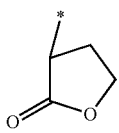 (r-lc-1-1)
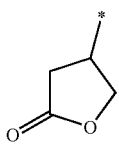 (r-lc-1-2)
 (r-lc-1-3)
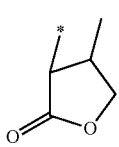 (r-lc-1-4)
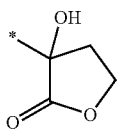 (r-lc-1-5)
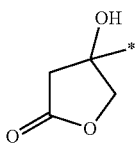 (r-lc-1-6)
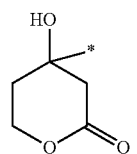 (r-lc-1-7)
 (r-lc-2-1)
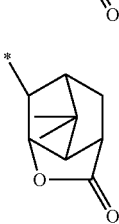 (r-lc-2-2)
-continued
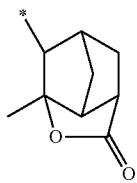 (r-lc-2-3)
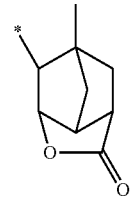 (r-lc-2-4)
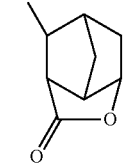 (r-lc-2-5)
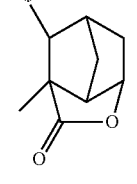 (r-lc-2-6)
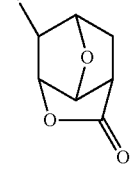 (r-lc-2-7)
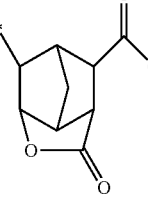 (r-lc-2-8)
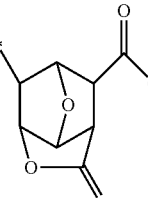 (r-lc-2-9)
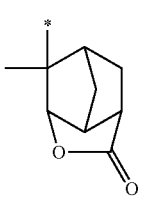 (r-lc-2-10)

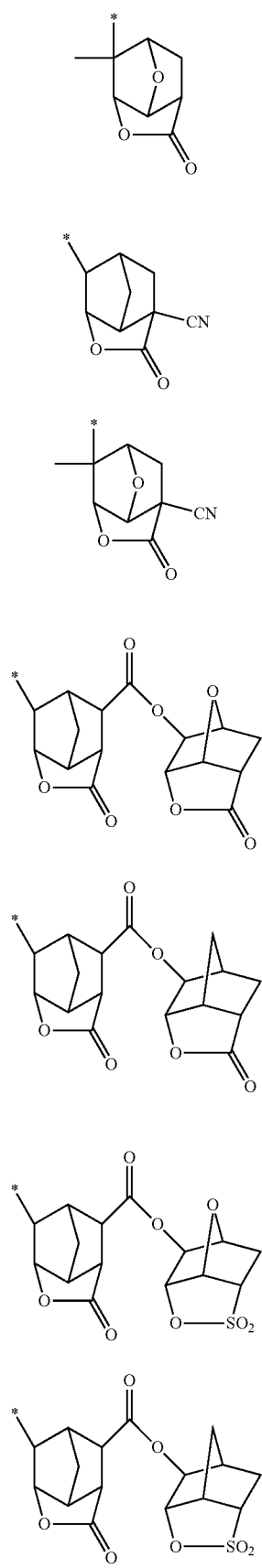
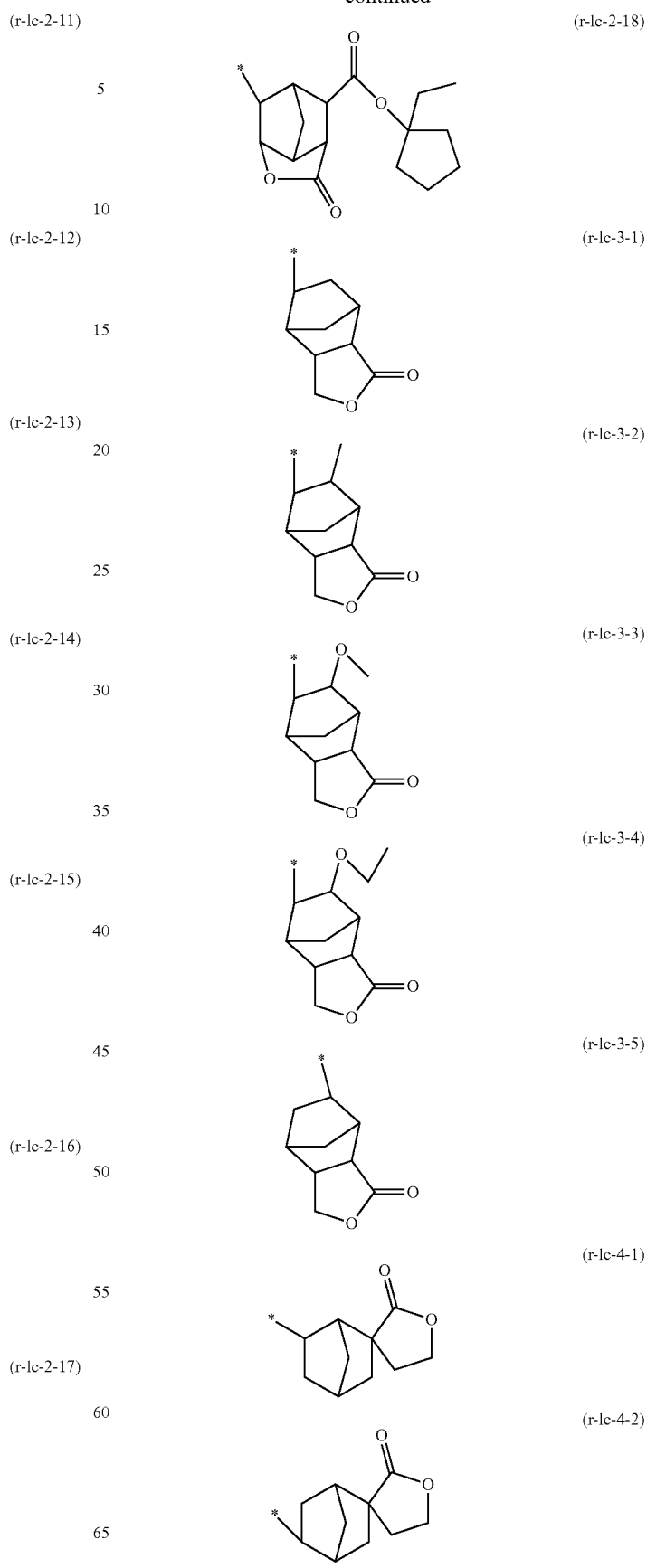

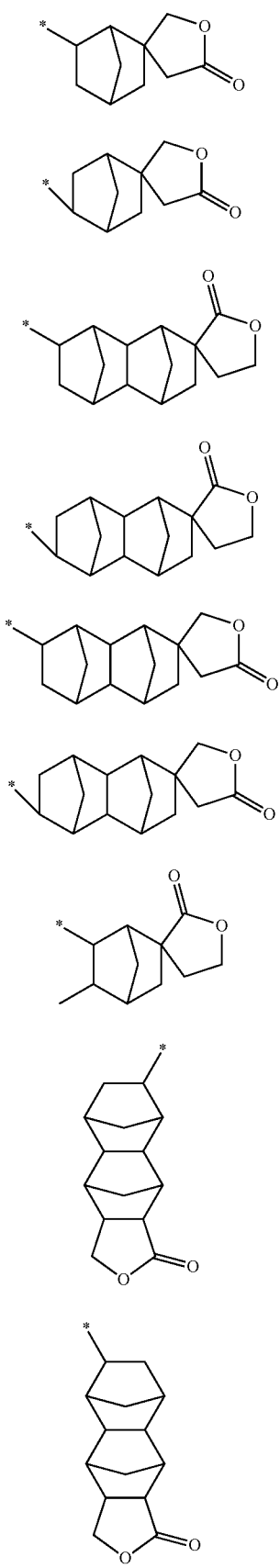
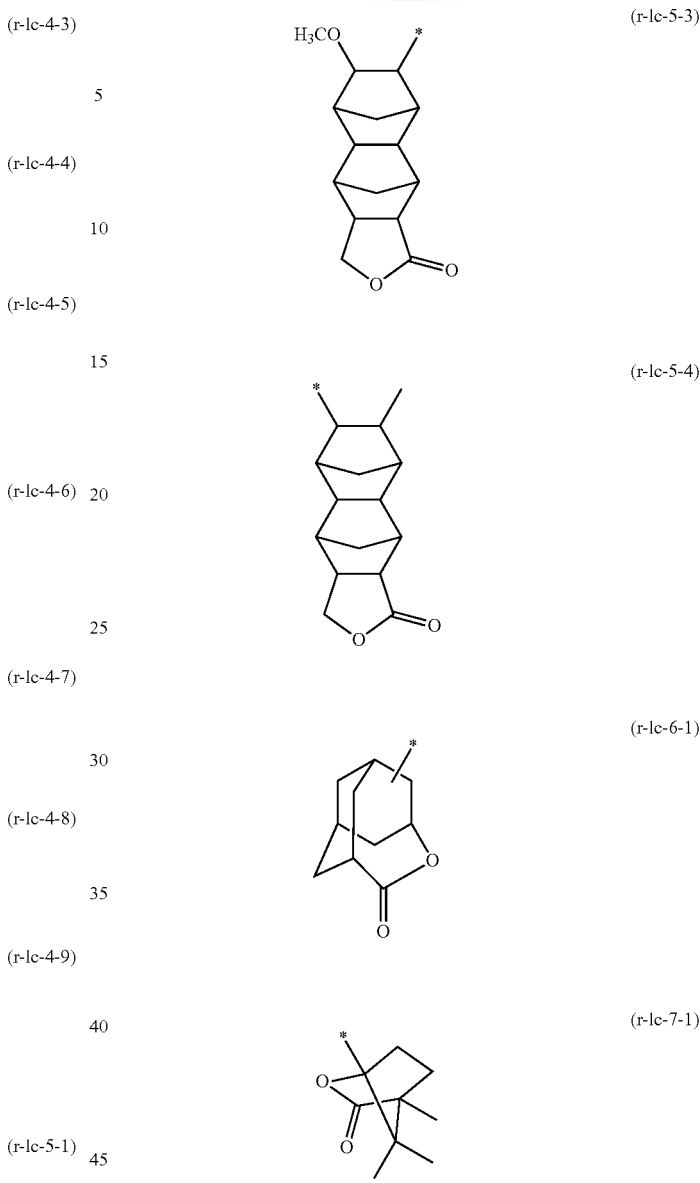

The "—SO$_2$-containing cyclic group" indicates a cyclic group having a ring containing —SO$_2$— in the ring structure thereof. Specifically, the —SO$_2$-containing cyclic group is a cyclic group in which the sulfur atom (S) in —SO$_2$— forms a part of the ring skeleton of the cyclic group. In a case where the ring containing —SO$_2$— in the ring skeleton thereof is counted as the first ring and the group contains only the ring, the group is referred to as a monocyclic group. Further, in a case where the group has other ring structures, the group is referred to as a polycyclic group regardless of the structures. The —SO$_2$-containing cyclic group may be a monocyclic group or a polycyclic group. As the —SO$_2$-containing cyclic group, a cyclic group containing —O—SO$_2$— in the ring skeleton thereof, in other words, a cyclic group containing a sultone ring in which —O—S— in the —O—SO$_2$— group forms a part of the ring skeleton thereof is particularly preferable.

More specific examples of the —SO$_2$-containing cyclic group include groups represented by Formulae (a5-r-1) to (a5-r-4) shown below.

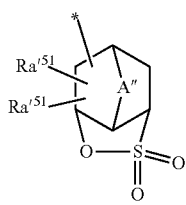
(a5-r-1)

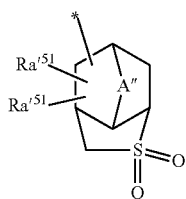
(a5-r-2)

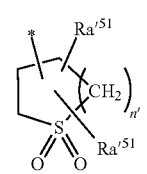
(a5-r-3)

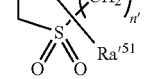
(a5-r-4)

[In the formulae, each $Ra'^{51}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group. R" represents a hydrogen atom, an alkyl group, a lactone-containing cyclic group, a carbonate-containing cyclic group, or a —SO$_2$-containing cyclic group. A" represents an oxygen atom, a sulfur atom or an alkylene group having 1 to 5 carbon atoms which may contain an oxygen atom or a sulfur atom. n' represents an integer of 0 to 2.]

In Formulae (a5-r-1) and (a5-r-2), A" has the same definition as that for A" in Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group as $Ra'^{51}$ include the same groups as those described above in the explanation of $Ra'^{21}$ in Formulae (a2-r-1) to (a2-r-7).

Specific examples of the groups represented by Formulae (a5-r-1) to (a5-r-4) are shown below. In the formulae shown below, "Ac" represents an acetyl group.

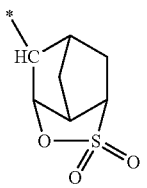
(r-s1-1-1)

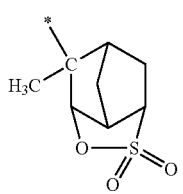
(r-s1-1-2)

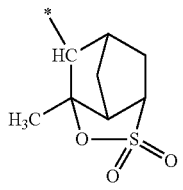
(r-s1-1-3)

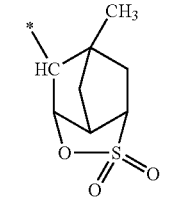
(r-s1-1-4)

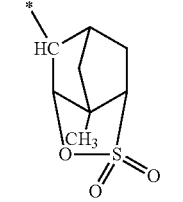
(r-s1-1-5)

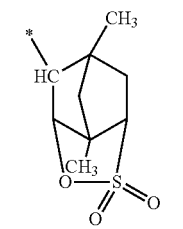
(r-s1-1-6)

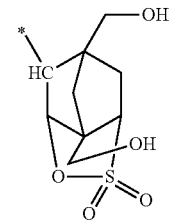
(r-s1-1-7)

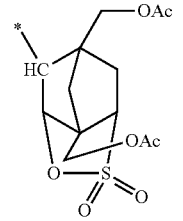
(r-s1-1-8)

(r-s1-1-9)
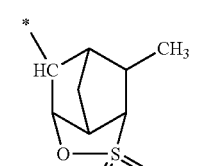
(r-s1-1-10)
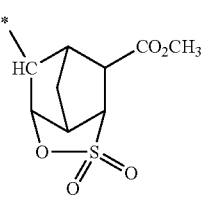
(r-s1-1-11)
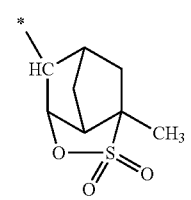
(r-s1-1-12)
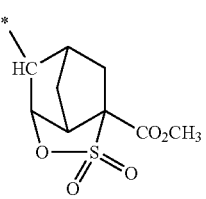
(r-s1-1-13)
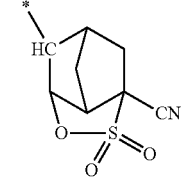
(r-s1-1-14)
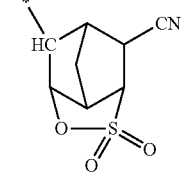
(r-s1-1-15)
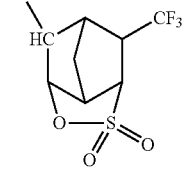
(r-s1-1-16)
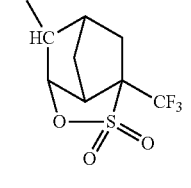
(r-s1-1-17)
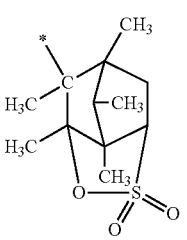
(r-s1-1-18)
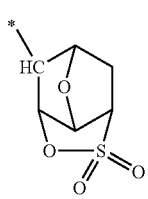
(r-s1-1-19)
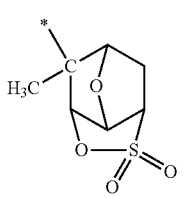
(r-s1-1-20)
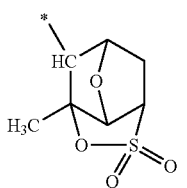
(r-s1-1-21)
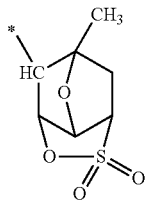
(r-s1-1-22)
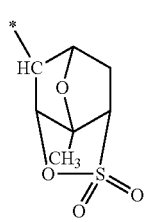
(r-s1-1-23)
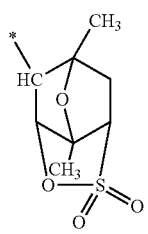

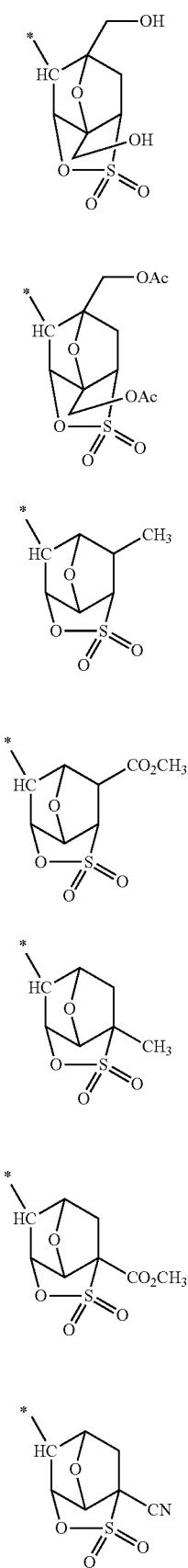
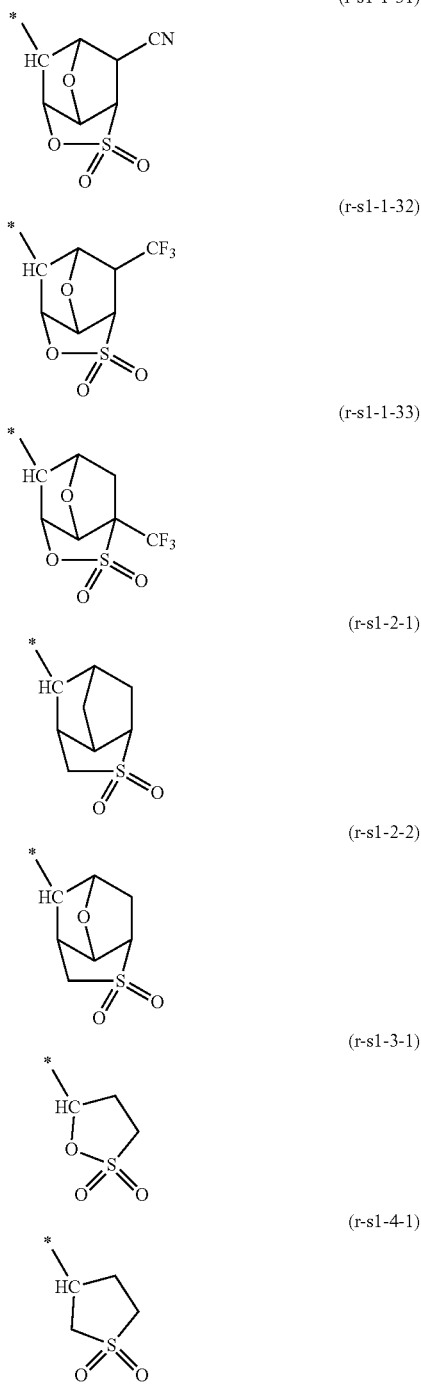

The "carbonate-containing cyclic group" indicates a cyclic group having a ring (a carbonate ring) containing —O—C(=O)—O— in the ring structure thereof. In a case where the carbonate ring is counted as the first ring and the group contains only the carbonate ring, the group is referred to as a monocyclic group. Further, in a case where the group has other ring structures, the group is referred to as a polycyclic group regardless of the structures. The carbonate-containing cyclic group may be a monocyclic group or a polycyclic group.

The carbonate ring-containing cyclic group is not particularly limited, and an optional group may be used. Specific examples thereof include groups represented by Formulae (ax3-r-1) to (ax3-r-3) shown below.

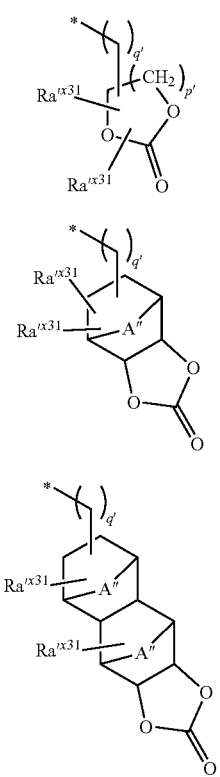

(ax3-r-1)

(ax3-r-2)

(ax3-r-3)

[In the formulae, each Ra'$^{x31}$ independently represents a hydrogen atom, an alkyl group, an alkoxy group, a halogen atom, a halogenated alkyl group, a hydroxyl group, —COOR", —OC(=O)R", a hydroxyalkyl group, or a cyano group. R" represents a hydrogen atom, an alkyl group, a lactone-containing cyclic group, a carbonate-containing cyclic group, or a —SO$_2$-containing cyclic group. A" represents an oxygen atom, a sulfur atom or an alkylene group having 1 to 5 carbon atoms which may contain an oxygen atom or a sulfur atom. p' represents an integer of 0 to 3, and q' represents 0 or 1.]

In Formulae (ax3-r-2) and (ax3-r-3), A" has the same definition as that for A" in Formulae (a2-r-2), (a2-r-3) and (a2-r-5).

Examples of the alkyl group, the alkoxy group, the halogen atom, the halogenated alkyl group, —COOR", —OC(=O)R", and the hydroxyalkyl group as Ra'$^{31}$ include the same groups as those described above in the explanation of Ra'$^{21}$ in Formulae (a2-r-1) to (a2-r-7).

Specific examples of the groups represented by Formulae (ax3-r-1) to (ax3-r-3) are shown below.

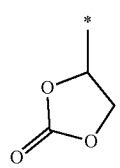

(r-cr-1-1)

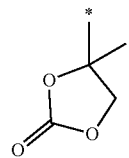

(r-cr-1-2)

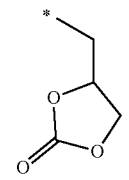

(r-cr-1-3)

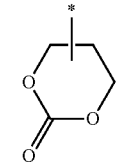

(r-cr-1-4)

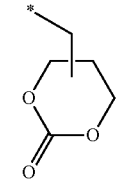

(r-cr-1-5)

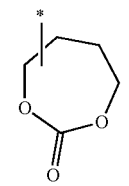

(r-cr-1-6)

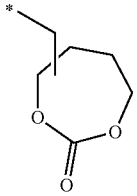

(r-cr-1-7)

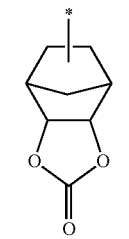

(r-cr-2-1)

(r-cr-2-2) 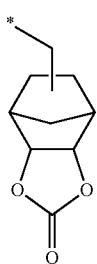

(r-cr-2-3) 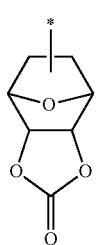

(r-cr-2-4) 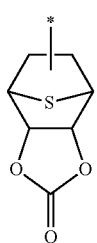

(r-cr-3-1) 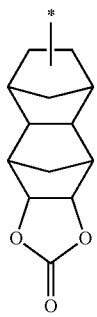

(r-cr-3-2) 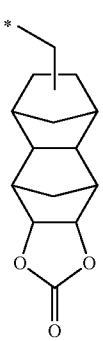

(r-cr-3-3) 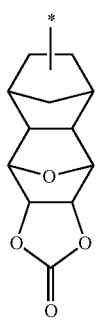

(r-cr-3-4) 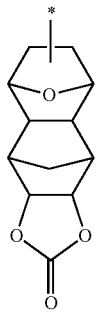

(r-cr-3-5) 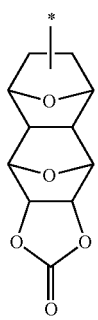

As the constitutional unit (a2), a constitutional unit derived from acrylic acid ester in which the hydrogen atom bonded to the carbon atom at the α-position may be substituted with a substituent is preferable.

Specific preferred examples of such a constitutional unit (a2) include a constitutional unit represented by Formula (a2-1) shown below.

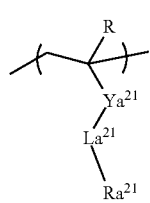

(a2-1)

[In the formula, R represents a hydrogen atom, an alkyl group having 1 to 5 carbon atoms, or a halogenated alkyl group having 1 to 5 carbon atoms. $Ya^{21}$ represents a single bond or a divalent linking group. $La^{21}$ represents —O—, —COO—, —CON(R')—, —OCO—, —CONHCO— or —CONHCS—. R' represents a hydrogen atom or a methyl group; here, in a case where $La^{21}$ represents —O—, $Ya^{21}$ does not represents —CO—. $Ra^{21}$ represents a lactone-containing cyclic group, a carbonate-containing cyclic group, or a —SO$_2$-containing cyclic group.]

In Formula (a2-1), R has the same definition as described above. R represents preferably a hydrogen atom, an alkyl group having 1 to 5 carbon atoms, or a fluorinated alkyl group having 1 to 5 carbon atoms and particularly preferably a hydrogen atom or a methyl group from the viewpoint of industrial availability.

In Formula (a2-1), the divalent linking group as Ya$^{21}$ is not particularly limited, and suitable examples thereof include a divalent hydrocarbon group which may have a substituent and a divalent linking group having hetero atoms. The divalent hydrocarbon group which may have a substituent and the divalent linking group containing a hetero atom as Ya$^{21}$ are defined the same as the divalent hydrocarbon group which may be a substituent and the divalent linking group containing a hetero atom as Ya$^{x1}$ in Formula (a10-1) stated above, respectively.

As Ya$^{21}$, a single bond, an ester bond [—C(=O)—O—], an ether bond (—O—), a linear or branched alkylene group, or a combination of these is preferable.

In Formula (a2-1), Ra$^{21}$ represents a lactone-containing cyclic group, a —SO$_2$-containing cyclic group, or a carbonate-containing cyclic group.

Preferred examples of the lactone-containing cyclic group, the —SO$_2$-containing cyclic group, and the carbonate-containing cyclic group as Ra$^{21}$ include groups represented by Formulae (a2-r-1) to (a2-r-7), groups represented by Formulae (a5-r-1) to (a5-r-4), and groups represented by Formulae (ax3-r-1) to (ax3-r-3).

Among the examples, Ra$^{21}$ represents preferably a lactone-containing cyclic group or a —SO$_2$-containing cyclic group and more preferably a group represented by Formula (a2-r-1), (a2-r-2), (a2-r-6) or (a5-r-1). Specifically, a group represented by any of Chemical Formulae (r-1c-1-1) to (r-1c-1-7), (r-1c-2-1) to (r-1c-2-18), (r-1c-6-1) to (r-s1-1-1), and (r-s1-1-18) is more preferable, and a group represented by Formula (r-1c-1-1) is still more preferable.

The constitutional unit (a2) in the component (A1) may be used alone or two or more kinds thereof.

In a case where the component (A1) has the constitutional unit (a2), the proportion of the constitutional unit (a2) in the component (A1) is preferably in a range of 1% to 50% by mole, more preferably in a range of 5% to 45% by mole, still more preferably in a range of 10% to 40% by mole, and particularly preferably in a range of 10% to 30% by mole with respect to the total amount (100% by mole) of all constitutional units constituting the component (A1).

By setting the proportion of the constitutional unit (a2) to be greater than or equal to the preferable lower limit, the effects obtained by allowing the constitutional unit (a2) to be contained in the component (A1) can be sufficiently obtained. Further, in a case where the proportion of the constitutional unit (a2) is lower than or equal to the upper limit of the above-described preferable range, the constitutional unit (a2) and other constitutional units can be balanced, and various lithography characteristics are enhanced.

<<Constitutional Unit (a3)>>

It is preferable that the component (A1) further has a constitutional unit (a3) (here, a constitutional unit corresponding to the constitutional unit (a1) or the constitutional unit (a2) is excluded) containing a polar group-containing aliphatic hydrocarbon group, in addition to the constitutional unit (a1). As the component (A1) has the constitutional unit (a3), for example, the acid diffusion length is appropriately adjusted, the adhesion of the resist film to the substrate is enhanced, the solubility during development is appropriately adjusted, and the etching resistance is improved. Therefore, the lithography characteristics are enhanced.

Examples of the polar group include a hydroxyl group, a cyano group, a carboxy group, or a hydroxyalkyl group in which some hydrogen atoms of the alkyl group have been substituted with fluorine atoms. Among these, a hydroxyl group is particularly preferable.

Examples of the aliphatic hydrocarbon group include linear or branched hydrocarbon groups (preferably alkylene groups) having 1 to 10 carbon atoms, and cyclic aliphatic hydrocarbon groups (cyclic groups). The cyclic group may be a monocyclic group or a polycyclic group. For example, these cyclic groups may be a monocyclic group or a polycyclic group and can be selected appropriately from the multitude of groups that have been proposed for the resins of resist compositions for ArF excimer lasers. The cyclic group is preferably a polycyclic group and more preferably a polycyclic group having 7 to 30 carbon atoms.

Among the examples, constitutional units derived from acrylic acid ester that include an aliphatic polycyclic group containing a hydroxyl group, cyano group, carboxy group, or a hydroxyalkyl group in which some hydrogen atoms of the alkyl group have been substituted with fluorine atoms are particularly preferable. Examples of the polycyclic group include groups in which two or more hydrogen atoms have been removed from a bicycloalkane, tricycloalkane, tetracycloalkane or the like. Specific examples thereof include groups in which two or more hydrogen atoms have been removed from a polycycloalkane such as adamantane, norbornane, isobornane, tricyclodecane or tetracyclododecane. Among these polycyclic groups, groups in which two or more hydrogen atoms have been removed from adamantane, groups in which two or more hydrogen atoms have been removed from norbornane or groups in which two or more hydrogen atoms have been removed from tetracyclododecane are preferred industrially.

The constitutional unit (a3) is not particularly limited as long as the constitutional unit contains a polar group-containing aliphatic hydrocarbon group, and an optional constitutional unit may be used.

The constitutional unit (a3) is a constitutional unit derived from acrylic acid ester in which the hydrogen atom bonded to the carbon atom at the α-position may be substituted with a substituent, and a constitutional unit containing a polar group-containing aliphatic hydrocarbon group is preferable.

In a case where the hydrocarbon group in the polar group-containing aliphatic hydrocarbon group is a linear or branched hydrocarbon group having 1 to 10 carbon atoms, the constitutional unit (a3) is preferably a constitutional unit derived from hydroxyethyl ester of acrylic acid.

On the other hand, in a case where the hydrocarbon group in the polar group-containing aliphatic hydrocarbon group is a polycyclic group, a constitutional unit represented by Formula (a3-1), a constitutional unit represented by Formula (a3-2), and a constitutional unit represented by Formula (a3-3) shown below are preferable as the constitutional unit (a3), and in particular, the constitutional unit represented by Formula (a3-1) is more preferable.

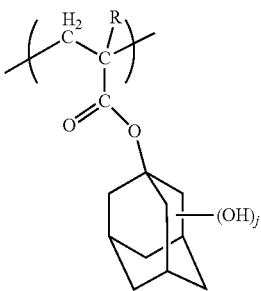

(a3-1)

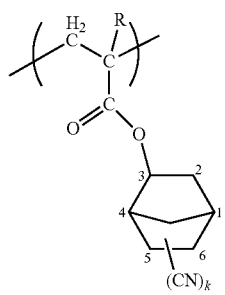

(a3-2)

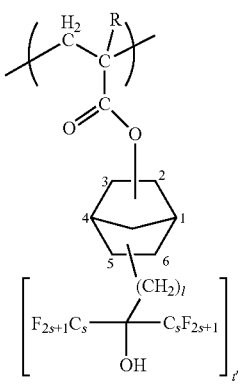

(a3-3)

[In the formulae, R has the same definition as described above, j represents an integer of 1 to 3, k represents an integer of 1 to 3, t' represents an integer of 1 to 3, l represents an integer of 1 to 5, and s represents an integer of 1 to 3.]

In Formula (a3-1), j represents preferably 1 or 2 and more preferably 1. In a case where j represents 2, it is preferable that the hydroxyl groups are bonded to the 3rd and 5th positions of the adamantyl group. In a case where j represents 1, it is preferable that the hydroxyl group is bonded to the 3rd position of the adamantyl group.

j represents preferably 1, and it is particularly preferable that the hydroxyl group is bonded to the 3rd position of the adamantyl group.

In Formula (a3-2), k represents preferably 1. The cyano group is preferably bonded to the 5th or 6th position of the norbornyl group.

In Formula (a3-3), t' represents preferably 1. l represents preferably 1. s represents preferably 1. Further, it is preferable that a 2-norbornyl group or a 3-norbornyl group is bonded to the terminal of the carboxy group of the acrylic acid. The fluorinated alkyl alcohol is preferably bonded to the 5th or 6th position of the norbornyl group.

The constitutional unit (a3) included in the component (A1) may be used alone or two or more kinds thereof.

In a case where the component (A1) has the constitutional unit (a3), the proportion thereof is preferably in a range of 1% to 40% by mole, more preferably in a range of 2% to 30% by mole, still more preferably in a range of 5% to 25% by mole, and particularly preferably in a range of 5% to 20% by mole with respect to the total amount of all constitutional units constituting the component (A1).

By setting the proportion of the constitutional unit (a3) to be greater than or equal to the preferable lower limit, the effects obtained by allowing the constitutional unit (a3) to be contained in the component (A1) can be sufficiently obtained. Further, in a case where the proportion thereof is lower than or equal to the upper limit of the preferable range, the balance with other constitutional units can be easily taken, and various lithography characteristics are enhanced.

<<Other Constitutional Units>>

The component (A1) may have other constitutional units other than the constitutional unit (a1), the constitutional unit (a10), the constitutional unit (a2), and the constitutional unit (a3) described above.

Examples of the other constitutional units include a constitutional unit (a9) represented by Formula (a9-1) described below, a constitutional unit derived from styrene, a constitutional unit derived from a styrene derivative (here, a constitutional unit corresponding to the constitutional unit (a10) is excluded), and a constitutional unit containing a non-acid dissociable aliphatic cyclic group.

Constitutional Unit (a9):

The constitutional unit (a9) is a constitutional unit represented by Formula (a9-1) shown below.

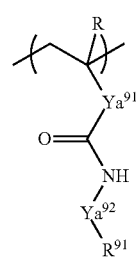

(a9-1)

[In the formula, R represents a hydrogen atom, an alkyl group having 1 to 5 carbon atoms, or a halogenated alkyl group having 1 to 5 carbon atoms. $Ya^{91}$ represents a single bond or a divalent linking group. $Ya^{92}$ represents a divalent linking group. $R^{91}$ represents a hydrocarbon group which may have a substituent.]

In Formula (a9-1), R has the same definition as described above.

R represents preferably a hydrogen atom, an alkyl group having 1 to 5 carbon atoms, or a fluorinated alkyl group having 1 to 5 carbon atoms and particularly preferably a hydrogen atom or a methyl group from the viewpoint of industrial availability.

Examples of the divalent linking group as $Ya^{91}$ in Formula (a9-1) include the same as the divalent linking groups as $Ya^{x1}$ in Formula (a10-1) described above. Among these, $Ya^{91}$ is preferably a single bond.

Examples of the divalent linking group as $Ya^{92}$ in Formula (a9-1) include the same as the divalent linking groups as $Ya^{x1}$ in Formula (a10-1) described above.

As the divalent hydrocarbon group which may have a substituent in the divalent linking group as $Ya^{92}$, a linear or branched aliphatic hydrocarbon group is preferable.

In a case where $Ya^{92}$ represents a divalent linking group containing a hetero atom, preferred examples of the linking group including a hetero atom include —O—, —C(=O)—O—, —C(=O)—, —O—C(=O)—O—, —C(=O)—NH—, —NH—, —NH—C(=NH)—, in which H may be substituted with a substituent such as an alkyl group, an acyl group, or the like, —S—, —S(=O)$_2$—, —S(=O)$_2$—O—, —C(=S)— and a group represented by Formula: —Y$^{21}$—O—Y$^{22}$—, —Y$^{21}$—O—, —Y$^{21}$—C(=O)—O—, —C(=O)—O—Y$^{21}$—, [Y$^{21}$—C(=O)—O]$_{m'}$—Y$^{22}$—, or —Y$^{21}$—O—C(=O)—Y$^{22}$— [in the formulae, Y$^{21}$ and Y$^{22}$ each independently represent a divalent hydrocarbon group which may have a substituent, O represents an oxygen atom, and m' represents an integer of 0 to 3]. Among these, —C(=O)— and —C(=S)— are preferable.

In Formula (a9-1), examples of the hydrocarbon group as R$^{91}$ include an alkyl group, a monovalent alicyclic hydrocarbon group, an aryl group, an aralkyl group and the like.

The alkyl group as R$^{91}$ preferably has 1 to 8 carbon atoms, more preferably 1 to 6 carbon atoms, and still more preferably 1 to 4 carbon atoms, and may be linear or branched. Specific preferable examples thereof include a methyl group, an ethyl group, a propyl group, a butyl group, a hexyl group, an octyl group and the like.

The monovalent alicyclic hydrocarbon group as R$^{91}$ preferably has 3 to 20 carbon atoms, and more preferably 3 to 12 carbon atoms, and may be polycyclic or monocyclic. As the monocyclic alicyclic hydrocarbon group, a group in which one or more hydrogen atoms have been removed from a monocycloalkane is preferable. The monocycloalkane has preferably 3 to 6 carbon atoms, and specific examples thereof include cyclobutane, cyclopentane, cyclohexane and the like. As the polycyclic alicyclic hydrocarbon group, a group in which one or more hydrogen atoms have been removed from a polycycloalkane is preferable. As the polycycloalkane, a group having 7 to 12 carbon atoms is preferable. Specific examples of the polycycloalkane include adamantane, norbornane, isobornane, tricyclodecane, tetracyclododecane and the like.

The aryl group as R$^{91}$ preferably has 6 to 18 carbon atoms, and more preferably 6 to 10 carbon atoms. In particular, a phenyl group is particularly preferable.

The aralkyl group as R$^{91}$ is preferably an aralkyl group in which an alkylene group having 1 to 8 carbon atoms is bonded to the "aryl group as R$^{91}$", more preferably an aralkyl group in which alkylene group having 1 to 6 carbon atoms is bonded to the "aryl group as R$^{91}$", and particularly preferably an aralkyl group in which an alkylene group having 1 to 4 carbon atoms is bonded to the "aryl group as R91".

The hydrocarbon group as R$^{91}$ is preferably a group in which some or all hydrogen atoms of the hydrocarbon group have been substituted with fluorine atoms, and more preferably a group in which 30% to 100% of the hydrogen atoms in the hydrocarbon group are substituted with fluorine atoms. Among these, a perfluoroalkyl group in which all the hydrogen atoms of the alkyl group are substituted with fluorine atoms is particularly preferable.

The hydrocarbon group as R$^{91}$ may have a substituent. Examples of the substituent include a halogen atom, an oxo group (=O), a hydroxyl group (—OH), an amino group (—NH$_2$), —SO$_2$—NH$_2$ and the like. Additionally, a part of carbon atoms constituting the hydrocarbon group may be substituted with substituents containing a hetero atom. Examples of the substituent containing a hetero atom include —O—, —NH—, —N=, —C(=O)—O—, —S—, —S(=O)$_2$—, and —S(=O)$_2$—O—.

Examples of the hydrocarbon group having a substituent as R$^{91}$ include lactone-containing cyclic groups represented by Formulae (a2-r-1) to (a2-r-7).

Examples of the hydrocarbon group having a substituent as R$^{91}$ include a —SO$_2$-containing cyclic group represented by Formulae (a5-r-1) to (a5-r-4) above; a substituted aryl group represented by the following chemical formulae, a monovalent heterocyclic group, and the like.

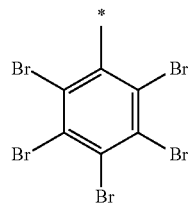

(r-ar-1)

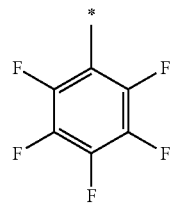

(r-ar-2)

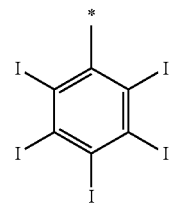

(r-ar-3)

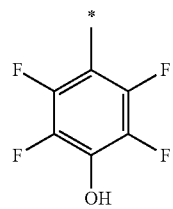

(r-ar-4)

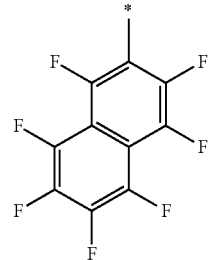

(r-ar-5)

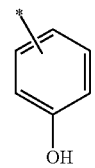

(r-ar-6)

(r-ar-7) 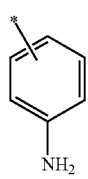

(r-ar-8) 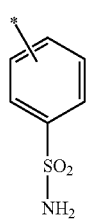

(r-hr-1) 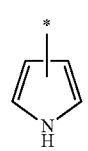

(r-hr-2) 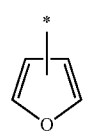

(r-hr-3) 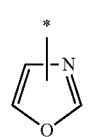

(r-hr-4) 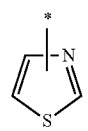

(r-hr-5) 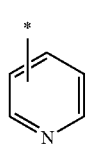

(r-hr-6) 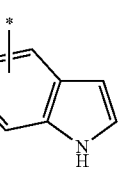

(r-hr-7) 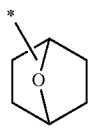

(r-hr-8) 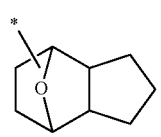

(r-hr-9) 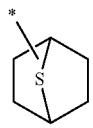

(r-hr-10) 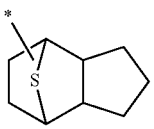

(r-hr-11) 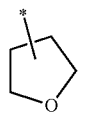

(r-hr-12) 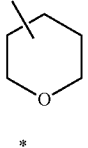

(r-hr-13) 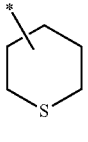

(r-hr-14) 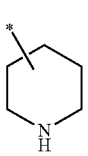

(r-hr-15) 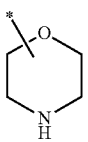

(r-hr-16)

Among the constitutional units (a9), a constitutional unit represented by Formula (a9-1-1) shown below is preferable.

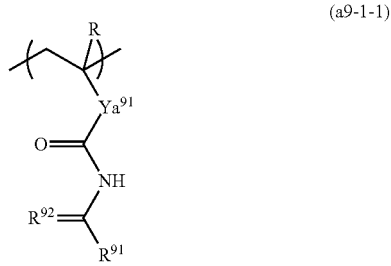

(a9-1-1)

[In the formula, R is as defined above, $Ya^{91}$ represents a single bond or a divalent linking group, $R^{91}$ represents a hydrocarbon group which may have a substituent, and $R^{92}$ represents an oxygen atom or a sulfur atom.]

In Formula (a9-1-1), $Ya^{91}$, $R^{91}$ and R are defined the same as above.
Moreover, $R^{92}$ represents an oxygen atom or a sulfur atom.
Specific examples of the constitutional unit represented by Formula (a9-1) or Formula (a9-1-1) are shown below. In formulae, Ra represents a hydrogen atom, a methyl group, or a trifluoromethyl group.
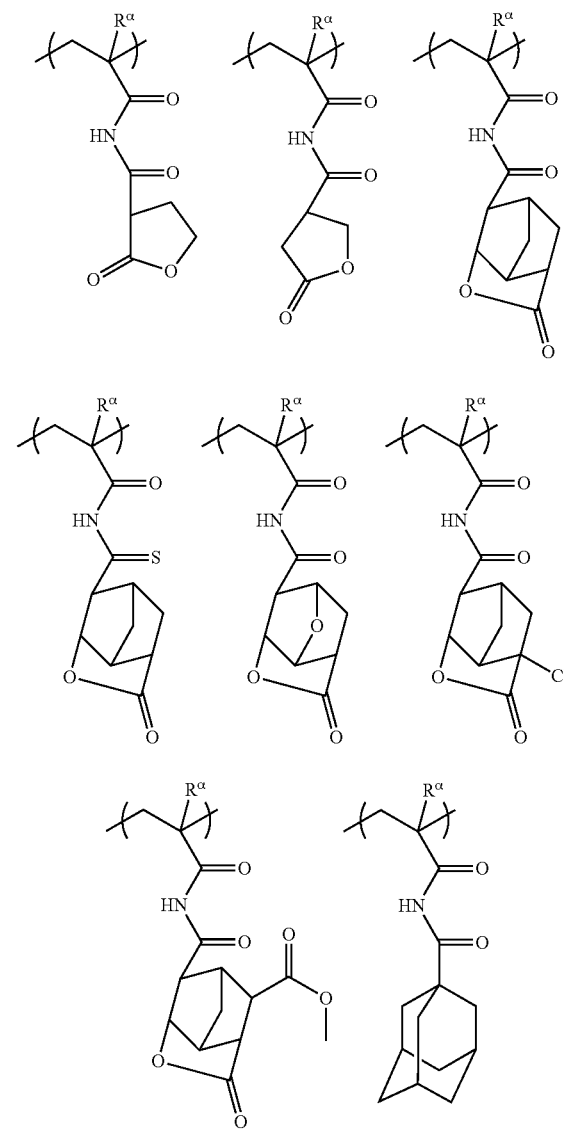
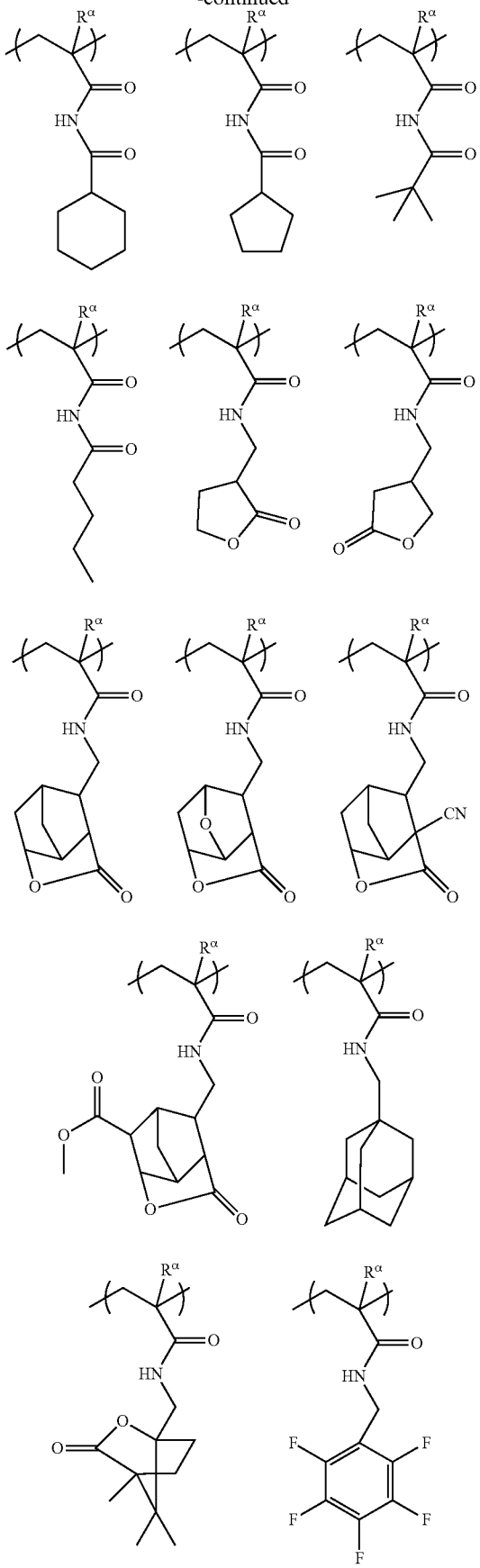

-continued

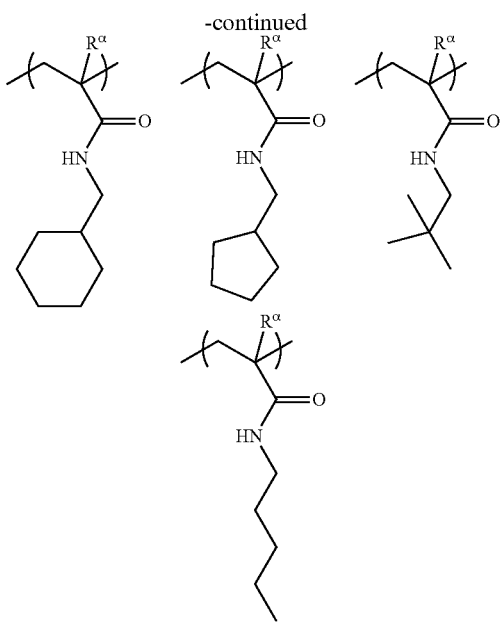

The constitutional unit (a9) included in the component (A1) may be used alone or two or more kinds thereof.

In a case where the component (A1) has the constitutional unit (a9), the proportion of the constitutional unit (a9) is preferably in a range of 1% to 40% by mole, more preferably in a range of 3% to 30% by mole, still more preferably in a range of 5% to 25% by mole, and particularly preferably in a range of 10% to 20% by mole with respect to the total amount (100% by mole) of all constitutional units constituting the component (A1).

By setting the proportion of the constitutional unit (a9) to be greater than or equal to the lower limit of the preferable range, the advantageous effects can be obtained, for example, the acid diffusion length is appropriately adjusted, the adhesion of the resist film to the substrate is enhanced, the solubility during development is appropriately adjusted, and the etching resistance is improved. Further, in a case where the proportion of the constitutional unit (a9) is lower than or equal to the upper limit of the preferable range, the constitutional unit (a9) and other constitutional units can be balanced, and various lithography characteristics are enhanced.

The component (A1) contained in the resist composition may be used alone or in combination of two or more.

The component (A1) preferably contains the polymer compound (A1-1) (hereinafter also referred to as a "component (A1-1)") having the constitutional unit (a1).

Preferred examples of the component (A1-1) include a polymer compound having repeating structures of the constitutional unit (a1) and the constitutional unit (a10) and the like.

In addition to the combination of the two constitutional units described above, the constitutional unit described above may be combined appropriately in order to obtain desired effects as a third constitutional unit, or alternatively, three or more of such constitutional units may be combined. The third constitutional unit is preferably the constitutional unit (a3).

In addition to the combination of the three constitutional units described above, a fourth constitutional unit is preferably the constitutional unit (a2).

The component (A1) can be prepared by dissolving a monomer from which each constitutional unit is derived in a polymerization solvent and polymerizing the dissolved monomer using a radical polymerization initiator such as azobisisobutylonitrile (AIBN) or dimethyl azobisisobutyrate (for example, V-601). Alternatively, the component (A1) can be prepared by dissolving a monomer from which the constitutional unit (a1) is derived, and optionally a precursor monomer (monomer for which the functional group is protected) from which the constitutional unit other than the constitutional unit (a1) is derived in a polymerization solvent, polymerizing the dissolved monomers using the radical polymerization initiator described above, followed by performing a deprotection reaction. Further, a —C(CF$_3$)$_2$—OH group may be introduced into a terminal during the polymerization using a chain transfer agent such as HS—CH$_2$—CH$_2$—CH$_2$—C(CF$_3$)$_2$—OH together. As described above, a copolymer into which a hydroxyalkyl group, formed by substitution of some hydrogen atoms in the alkyl group with fluorine atoms, has been introduced is effective for reducing development defects and reducing line edge roughness (LER: uneven irregularities of a line sidewall).

The weight average molecular weight (Mw) (in terms of polystyrene determined by gel permeation chromatography (GPC)) of the component (A1) is not particularly limited, but is preferably in a range of 1,000 to 50,000, more preferably in a range of 2,000 to 30,000, and still more preferably in a range of 3,000 to 20,000.

In a case where the weight average molecular weight (Mw) of the component (A1) is less than or equal to the preferable upper limit of the above-described range, the resist composition exhibits a satisfactory solubility in a solvent for a resist enough to be used as a resist. Meanwhile, in a case where the weight average molecular weight is greater than or equal to the preferable lower limit of the above-described range, dry etching resistance and the cross-sectional shape of the resist pattern become excellent.

The dispersity (Mw/Mn) of the component (A1) is not particularly limited, but preferably in a range of 1.0 to 4.0, more preferably in a range of 1.0 to 3.0, and particularly preferably in a range of 1.1 to 2.0. Moreover, Mn indicates a number average molecular weight.

Regarding Component (A2)

In the resist composition of the present embodiment, a base material component (hereinafter, referred to as a "component (A2)") which does not correspond to the component (A1) and of which solubility in a developing solution is changed due to the action of an acid may be used in combination as the component (A).

The component (A2) is not particularly limited, and may be optionally selected from those known in the related art as the base material components for a chemically amplified resist composition.

In the component (A2), a high molecular weight compound or a low molecular weight compound may be used alone or in combination of two or more kinds thereof.

The proportion of the component (A1) in the component (A) is preferably 25% by mass or greater, more preferably 50% by mass or greater, still more preferably 75% by mass or greater, or may be 100% by mass with respect to the total mass of the component (A). In a case where the proportion thereof is 25% by mass or greater, a resist pattern with excellent lithography characteristics of enhancing the high sensitivity, resolution, or roughness and the like is easily formed. These advantageous effects are particularly remarkable in electron beam lithography and EUV lithography.

In the resist composition of the present embodiment, the content of the component (A) may be adjusted according to the film thickness of a resist intended to be formed.

<Compound (BD1)>

In the resist composition of the present embodiment, the component (BD1) is a compound represented by Formula (bd1) and composed of an anion moiety and a cation moiety.

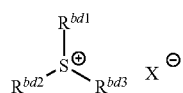
(bd1)

[In the formula, $R^{bd1}$ to $R^{bd3}$ each independently represent an aryl group which may have a substituent. Here, at least two of $R^{bd1}$ to $R^{bd3}$ are aryl groups having one or more fluorine atoms as substituents, and at least one of the fluorine atoms included in the aryl group is bonded to a carbon atom adjacent to a carbon atom that is bonded to a sulfur atom in the formula. In $R^{bd1}$ to $R^{bd3}$, the total number of the fluorine atoms bonded as substituents to the carbon atom adjacent to the carbon atom that is bonded to the sulfur atom in the formula is 4 or more. Two of $R^{bd1}$ to $R^{bd3}$ may be bonded to each other to form a fused ring together with the sulfur atom in the formula. $X^-$ represents a counter anion.]

Regarding Cation Moiety

In Formula (bd1), $R^{bd1}$ to $R^{bd3}$ each independently represent an aryl group which may have a substituent. Here, at least two of $R^{bd1}$ to $R^{bd3}$ are aryl groups having one or more fluorine atoms as substituents, and at least one of the fluorine atoms of the aryl group is bonded to a carbon atom adjacent to a carbon atom that is bonded to a sulfur atom in the formula.

In $R^{bd1}$ to $R^{bd3}$, the total number of the fluorine atoms bonded as substituents to the carbon atom adjacent to the carbon atom that is bonded to the sulfur atom in the formula is 4 or more. Two of $R^{bd1}$ to $R^{bd3}$ may be bonded to each other to form a fused ring together with the sulfur atom in the formula.

Examples of the aryl group as $R^{bd1}$ to $R^{bd3}$ include a group formed by removing one hydrogen atom from an aromatic hydrocarbon ring, such as benzene, naphthalene, anthracene, phenanthrene, biphenyl, and fluorene. Among them, as the aryl group as $R^{bd1}$ to $R^{bd3}$, a group formed by removing one hydrogen atom from benzene or naphthalene (phenyl group or naphthyl group) is preferable, and a group formed by removing one hydrogen atom from benzene (phenyl group) is more preferable.

Examples of substituents that the aryl group as $R^{bd1}$ to $R^{bd3}$ may have include an alkyl group, an alkoxy group, an acyl group, a halogen atom, a halogenated alkyl group, a sulfonyl group, a sulfonylalkyl group, a hydroxyl group, a carbonyl group, a cyano group, a nitro group, and an amino group. Among them, at least two of the aryl groups $R^{bd1}$ to $R^{bd3}$ have one or more fluorine atoms. Further, at least one of the fluorine atoms is bonded to a carbon atom adjacent to the carbon atom that is bonded to the sulfur atom in the formula.

In $R^{bd1}$ to $R^{bd3}$, the total number of the fluorine atoms bonded as substituents to the carbon atom adjacent to the carbon atom that is bonded to the sulfur atom in the formula is 4 or more, and may be 5 or more and may be 6 or more.

Four or more fluorine atoms being bonded to the site brings the effect of the present embodiment.

Two of $R^{bd1}$ to $R^{bd3}$ may be bonded to each other to form a fused ring together with the sulfur atom in the formula. In a case where two of $R^{bd1}$ to $R^{bd3}$ are bonded to one another to form a fused ring with a sulfur atom in the formula, these groups may be bonded via a hetero atom such as a sulfur atom, an oxygen atom or a nitrogen atom, or a functional group such as a carbonyl group, —SO—, —SO$_2$—, —COO—, —CONH—, —N(R$_N$)— (here, R$_N$ represents an alkyl group having 1 to 5 carbon atoms) or the like.

Specific examples of the fused ring to be formed include a dibenzothiophene ring.

Specific examples of the cation moiety in the compound (BD1) include cations represented by Formulae (ca-bd-1) to (ca-bd-15).

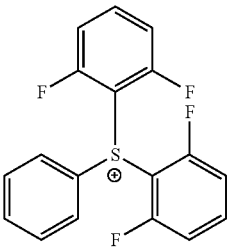
(ca-bd-1)

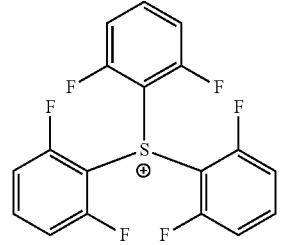
(ca-bd-2)

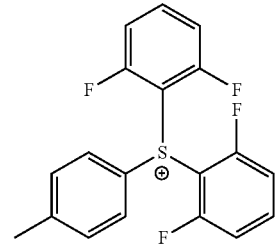
(ca-bd-3)

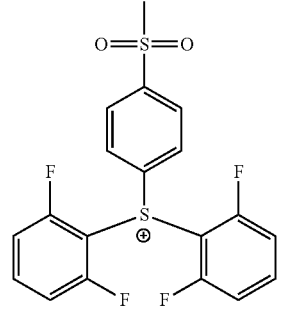
(ca-bd-4)

-continued
(ca-bd-5)
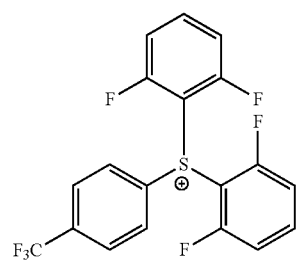
(ca-bd-6)
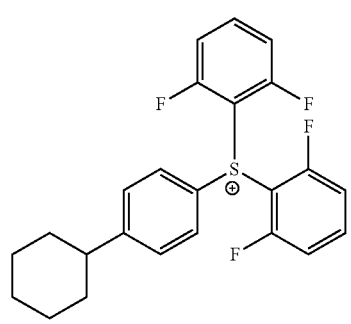
(ca-bd-7)
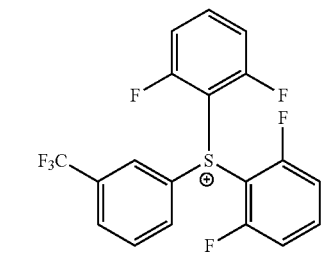
(ca-bd-8)
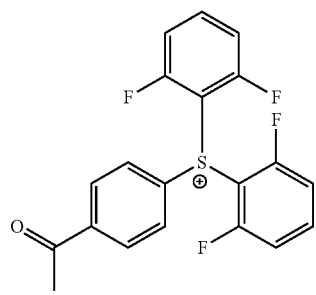
(ca-bd-9)
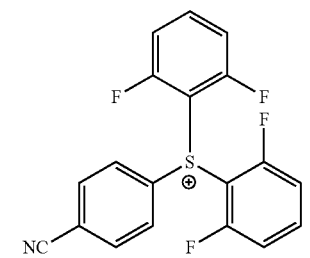
-continued
(ca-bd-10)
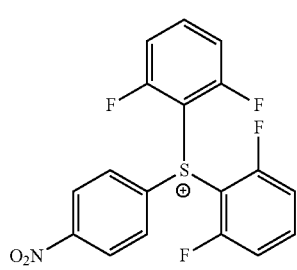
(ca-bd-11)
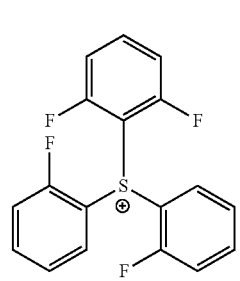
(ca-bd-12)
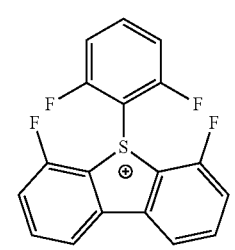
(ca-bd-13)
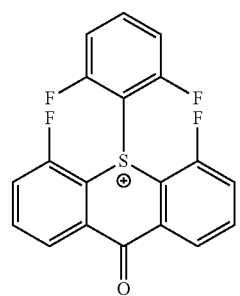
(ca-bd-14)
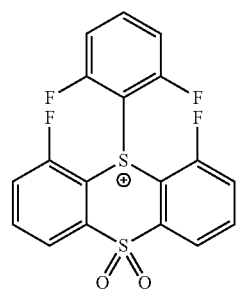

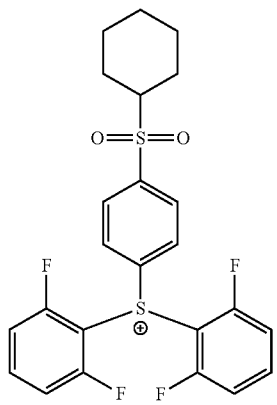

(ca-bd-15)

As the cation in the compound (BD1), a cation represented by Formula (ca-bd0-1) is preferable.

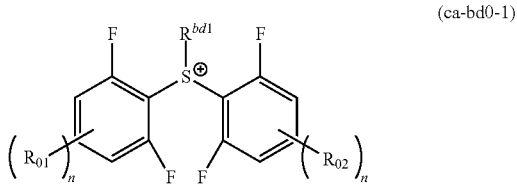

(ca-bd0-1)

[In the formula, $R^{bd1}$ represents an aryl group which may have a substituent. $R_{01}$ and $R_{02}$ each independently represent a substituent; each n independently represents an integer of 0 to 3.]

In Formula (ca-bd0-1), $R^{bd1}$ is the same as described in explanation of $R^{bd1}$ to $R^{bd3}$ in Formula (bd1).

Examples of $R_{01}$ and $R_{02}$ are the same as the substituents described in the explanation of $R^{bd1}$ to $R^{bd3}$ in Formula (bd1).

Each n independently represents an integer of 0 to 3.

As the cation moiety in the compound (BD1), a cation represented by any of Formulae (ca-bd-1) to (ca-bd-15) is preferable. Among them, a cation represented by any of Formulae (ca-bd-1) to (ca-bd-11) corresponding to the cation of Formula (ca-bd0-1) is more preferable, and a cation represented by any of Formulae (ca-bd-1) to (ca-bd-4) is still more preferable.

Regarding Anion Moiety

In Formula (bd1), X⁻ represents a counter anion.

The counter anion is not particularly limited, and examples thereof include a sulfonate anion, a carboxylate anion, an imide anion, a methide anion, a carbanion, a borate anion, a halogen anion, a phosphate anion, an antimonate anion, an arsenate anion and the like.

In the resist composition of the present embodiment, the component (BD1) may be used as the component (B) or as the component (D) by selecting the counter anion (anion moiety).

In a case where the component (BD1) is used as an acid generator, the component (BD1) is referred to as the component (B1), and in a case where the component (BD1) is used as a base component for trapping the acid generated from the component (B) (controlling acid diffusion), the component (BD1) is referred to as the component (D1).

Hereinafter, the anion moiety of the component (BD1) is classified into anion moiety (counter anion) of the component (B1) and anion moiety (counter anion) of the component (D1), and preferable anions for each of those will be described.

Anion Moiety of Component (B1)

In a case where the component (BD1) is used as an acid generator, any known anion as the anion moiety of acid generator component for resist composition can be appropriately used as X⁻ in Formula (bd1).

Examples of X⁻ include an anion represented by Formula (b1-1-an1), an anion represented by Formula (b1-1-an2), or an anion represented by Formula (b1-1-an3).

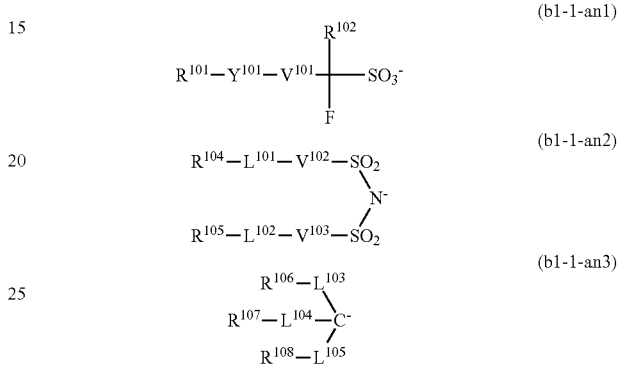

[In the formulae, $R^{101}$ and $R^{104}$ to $R^{108}$ independently represent a cyclic group which may have a substituent, a chain-like alkyl group which may have a substituent, or a chain-like alkenyl group which may have a substituent. $R^{104}$ and $R^{105}$ may be bonded to each other to form a ring structure. $R^{102}$ represents a fluorinated alkyl group having 1 to 5 carbon atoms or a fluorine atom. $Y^{101}$ represents a divalent linking group containing an oxygen atom or a single bond. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO—, or —SO₂—.

Anion Represented by Formula (b1-1-an1)

In Formula (b1-1-an1), $R^{101}$ represents a cyclic group which may have a substituent, a chain-like alkyl group which may have a substituent, or a chain-like alkenyl group which may have a substituent.

Cyclic Group which May have Substituent:

The cyclic group is preferably a cyclic hydrocarbon group, and the cyclic hydrocarbon group may be an aromatic hydrocarbon group or an aliphatic hydrocarbon group. The aliphatic hydrocarbon group indicates a hydrocarbon group that has no aromaticity. The aliphatic hydrocarbon group may be saturated or unsaturated, but in general, the aliphatic hydrocarbon group is preferably saturated.

The aromatic hydrocarbon group as $R^{101}$ is a hydrocarbon group having an aromatic ring. The aromatic hydrocarbon group has preferably 3 to 30 carbon atoms, more preferably 5 to 30 carbon atoms, still more preferably 5 to 20 carbon atoms, and particularly preferably 6 to 18 carbon atoms. Here, the number of carbon atoms in a substituent is not included in the number of carbon atoms.

Specific examples of the aromatic ring contained in the aromatic hydrocarbon group as $R^{101}$ include benzene, fluorene, naphthalene, anthracene, phenanthrene, biphenyl, or an aromatic heterocyclic ring in which some carbon atoms constituting any of these aromatic rings have been substituted with hetero atoms. Examples of the hetero atom in the aromatic heterocyclic rings include an oxygen atom, a sulfur atom, and a nitrogen atom.

Specific examples of the aromatic hydrocarbon group as $R^{101}$ include a group in which one hydrogen atom has been removed from the above-described aromatic ring (an aryl group such as a phenyl group, a naphthyl group or the like), a group in which one hydrogen atom in the aromatic ring has been substituted with an alkylene group (an arylalkyl group such as a benzyl group, a phenethyl group, a 1-naphthylmethyl group, a 2-naphthylmethyl group, 1-naphthylethyl group, a 2-naphthylethyl group or the like), and a group in which one hydrogen atom has been removed from a fused ring in which the aromatic ring is fused with a bridged aliphatic ring such as bicycloheptane and bicyclooctane. The alkylene group (an alkyl chain in the arylalkyl group) has preferably 1 to 4 carbon atoms, more preferably 1 or 2 carbon atoms, and particularly preferably 1 carbon atom.

Examples of the cyclic aliphatic hydrocarbon group as $R^{101}$ include aliphatic hydrocarbon groups containing a ring in the structure thereof.

Examples of the aliphatic hydrocarbon group containing a ring in the structure thereof include an alicyclic hydrocarbon group (a group in which one hydrogen atom has been removed from an aliphatic hydrocarbon ring), a group in which the alicyclic hydrocarbon group is bonded to the terminal of a linear or branched aliphatic hydrocarbon group, and a group in which the alicyclic hydrocarbon group is interposed in a linear or branched aliphatic hydrocarbon group.

The alicyclic hydrocarbon group has preferably 3 to 20 carbon atoms and more preferably 3 to 12 carbon atoms.

The alicyclic hydrocarbon group may be a polycyclic group or a monocyclic group. As the monocyclic alicyclic hydrocarbon group, a group in which one or more hydrogen atoms have been removed from a monocycloalkane is preferable. The monocycloalkane has preferably 3 to 6 carbon atoms, and specific examples thereof include cyclopentane and cyclohexane. As the polycyclic alicyclic hydrocarbon group, a group in which one or more hydrogen atoms have been removed from a polycycloalkane is preferable, and the number of carbon atoms of the polycycloalkane is preferably in a range of 7 to 30. Among polycycloalkanes, a polycycloalkane having a bridged ring polycyclic skeleton, such as adamantane, norbornane, isobornane, tricyclodecane, or tetracyclododecane, and a polycycloalkane having a fused ring polycyclic skeleton, such as a cyclic group having a steroid skeleton are preferable.

Among these examples, as the cyclic aliphatic hydrocarbon group as $R^{101}$, a group in which one or more hydrogen atoms have been removed from a monocycloalkane or a polycycloalkane is preferable, a group in which one hydrogen atom has been removed from a polycycloalkane is more preferable, an adamantyl group and a norbornyl group are particularly preferable, and an adamantyl group is most preferable.

The linear aliphatic hydrocarbon group which may be bonded to the alicyclic hydrocarbon group has preferably 1 to 10 carbon atoms, more preferably 1 to 6 carbon atoms, still more preferably 1 to 4 carbon atoms, and most preferably 1 to 3 carbon atoms. As the linear aliphatic hydrocarbon group, a linear alkylene group is preferable. Specific examples thereof include a methylene group [—$CH_2$—], an ethylene group [—$(CH_2)_2$—], a trimethylene group [—$(CH_2)_3$—], a tetramethylene group [—$(CH_2)_4$—], and a pentamethylene group [—$(CH_2)_5$—].

The branched aliphatic hydrocarbon group which may be bonded to the alicyclic hydrocarbon group has preferably 2 to 10 carbon atoms, more preferably 3 to 6 carbon atoms, still more preferably 3 or 4 carbon atoms, and most preferably 3 carbon atoms. As the branched aliphatic hydrocarbon group, a branched alkylene group is preferred, and specific examples thereof include alkylalkylene groups, for example, alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group in the alkylalkylene group, a linear alkyl group having 1 to 5 carbon atoms is preferable.

The cyclic hydrocarbon group as $R^{101}$ may contain a hetero atom as in a case of a heterocyclic ring and the like. Specific examples thereof include lactone-containing cyclic groups represented by Formulae (a2-r-1) to (a2-r-7), —$SO_2$—containing cyclic groups represented by Formulae (a5-r-1) to (a5-r-4), and other heterocyclic groups represented by Chemical Formulae (r-hr-1) to (r-hr-16).

Examples of the substituent for the cyclic group as $R^{101}$ include an alkyl group, an alkoxy group, a halogen atom, a halogenated alkyl group, a hydroxyl group, a carbonyl group, a nitro group, and the like.

The alkyl group as the substituent is preferably an alkyl group having 1 to 5 carbon atoms, and a methyl group, an ethyl group, a propyl group, an n-butyl group, or a tert-butyl group is most preferable.

The alkoxy group as the substituent is preferably an alkoxy group having 1 to 5 carbon atoms, more preferably a methoxy group, an ethoxy group, an n-propoxy group, an iso-propoxy group, an n-butoxy group, or a tert-butoxy group, and most preferably a methoxy group or an ethoxy group.

Examples of the halogen atom for the substituent include a fluorine atom, a chlorine atom, a bromine atom, and an iodine atom, and a fluorine atom is preferable.

Example of the halogenated alkyl group as the substituent includes a group in which some or all hydrogen atoms in an alkyl group having 1 to 5 carbon atoms such as a methyl group, an ethyl group, a propyl group, an n-butyl group, or a tert-butyl group have been substituted with the above-described halogen atoms.

The carbonyl group as the substituent is a group that substitutes a methylene group (—$CH_2$—) constituting the cyclic hydrocarbon group.

Among the above, as the substituent for the cyclic group as $R^{101}$, a hydroxyl group or an alkoxy group is preferable, and a hydroxyl group is more preferable.

Chain-Like Alkyl Group which May have Substituent:

The chain-like alkyl group as $R^{101}$ may be linear or branched.

The linear alkyl group has preferably 1 to 20 carbon atoms, more preferably 1 to 15 carbon atoms, and most preferably 1 to 10 carbon atoms. Specific examples thereof include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group, a docosyl group, and the like.

The branched alkyl group has preferably 3 to 20 carbon atoms, more preferably 3 to 15 carbon atoms, and most preferably 3 to 10 carbon atoms. Specific examples thereof include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, a 4-methylpentyl group, and the like.

Chain-Like Alkenyl Group which May have Substituent:

Such a chain-like alkenyl group as $R^{101}$ may be linear or branched, and has preferably 2 to 10 carbon atoms, more preferably 2 to 5 carbon atoms, still more preferably 2 to 4 carbon atoms, and particularly preferably 3 carbon atoms. Examples of the linear alkenyl group include a vinyl group, a propenyl group (an allyl group), and a butynyl group. Examples of the branched alkenyl group include a 1-methylvinyl group, a 2-methylvinyl group, a 1-methylpropenyl group, a 2-methylpropenyl group, and the like.

Among the examples, as the chain-like alkenyl group, a linear alkenyl group is preferable, a vinyl group or a propenyl group is more preferable, and a vinyl group is particularly preferable.

Examples of the substituent for the chain-like alkyl group or alkenyl group as $R^{101}$ include an alkoxy group, a halogen atom, a halogenated alkyl group, a hydroxyl group, a carbonyl group, a nitro group, an amino group, the cyclic groups exemplified as $R^{101}$ and the like.

Among the above, $R^{101}$ is preferably a cyclic group which may have a substituent, more preferably a polycyclic hydrocarbon group which may have a substituent, and still more preferably a bridged ring polycyclic hydrocarbon group. The cyclic group (polycyclic hydrocarbon group) may contain a hetero atom as in a case of a heterocyclic ring and the like.

Examples of the polycyclic hydrocarbon group include a group in which one hydrogen atom has been removed from a polycycloalkane having a polycyclic skeleton, and a group in which one hydrogen atom has been removed from a fused ring in which an aromatic ring is fused with a polycycloalkane having a polycyclic skeleton. Examples of the polycycloalkanes include a polycycloalkane having a bridged ring polycyclic skeleton, such as adamantane, norbornane (bicycloheptane), and bicyclooctane; and a polycycloalkane having a fused ring polycyclic skeleton, such as a cyclic group having a steroid skeleton. Among them, a polycycloalkane having a bridged ring polycyclic skeleton is preferable. Specific suitable examples of the polycyclic aliphatic hydrocarbon group include an adamantyl group and a norbornyl group.

Examples of the group in which one hydrogen atom has been removed from a fused ring in which an aromatic ring is fused with a polycycloalkane having a polycyclic skeleton include a group in which one hydrogen atom has been removed from a fused ring formed by the polycycloalkane and a benzene ring.

As the polycyclic hydrocarbon group having a heterocyclic ring, a bridged ring polycyclic hydrocarbon group having a heterocyclic ring is preferable, and specific examples thereof include the —SO$_2$—-containing bridged ring polycyclic groups represented by Formulae (a5-r-1) and (a5-r-2).

In Formula (b1-1-an1), $Y^{101}$ represents a single bond or a divalent linking group containing an oxygen atom.

In a case where $Y^{101}$ represents a divalent linking group containing an oxygen atom, $Y^{101}$ may contain an atom other than an oxygen atom. Examples of atoms other than an oxygen atom include a carbon atom, a hydrogen atom, a sulfur atom, and a nitrogen atom.

Examples of the divalent linking group containing an oxygen atom include a non-hydrocarbon linking group containing an oxygen atom, such as an oxygen atom (ether bond: —O—), an ester bond (—C(=O)—O—), an oxycarbonyl group (—O—C(=O)—), an amide bond (—C(=O)—NH—), a carbonyl group (—C(=O)—), a carbonate bond (—O—C(=O)—O—) or the like; combinations of an alkylene group and such a non-hydrocarbon linking group containing an oxygen atom; and the like. A sulfonyl group (—SO$_2$—) may be further linked to the combination. Examples of the divalent linking group containing an oxygen atom include linking groups represented by Formulae (y-a1-1) to (y-a1-7).

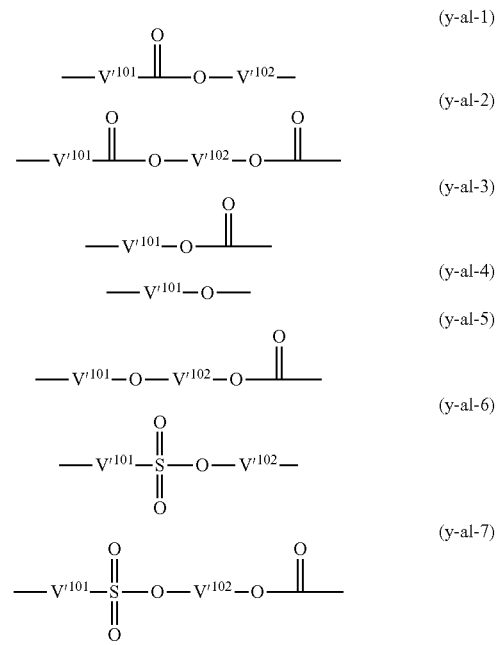

[In the formulae, $V'^{101}$ represents a single bond or an alkylene group having 1 to 5 carbon atoms, and $V'^{102}$ represents a divalent saturated hydrocarbon group having 1 to 30 carbon atoms.]

As the divalent saturated hydrocarbon group as $V'^{102}$, an alkylene group having 1 to 30 carbon atoms is preferable, an alkylene group having 1 to 10 carbon atoms is more preferable, and an alkylene group having 1 to 5 carbon atoms is still more preferable.

The alkylene group as $V'^{101}$ and $V'^{102}$ may be a linear alkylene group or a branched alkylene group, and a linear alkylene group is preferable.

Specific examples of the alkylene group as $V'^{101}$ and $V'^{102}$ include a methylene group [—CH$_2$—]; an alkylmethylene group such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, or —C(CH$_2$CH$_3$)$_2$—; an ethylene group [—CH$_2$CH$_2$—]; an alkylethylene group such as —CH(CH$_3$)CH$_2$—, —CH(CH$_3$)CH(CH$_3$)—, —C(CH$_3$)$_2$CH$_2$—, or —CH(CH$_2$CH$_3$)CH$_2$—; a trimethylene group (n-propylene group) [—CH$_2$CH$_2$CH$_2$—]; an alkyltrimethylene group such as —CH(CH$_3$)CH$_2$CH$_2$— or —CH$_2$CH(CH$_3$)CH$_2$—; a tetramethylene group [—CH$_2$CH$_2$CH$_2$CH$_2$—]; an alkyltetramethylene group such as —CH(CH$_3$)CH$_2$CH$_2$CH$_2$—, —CH$_2$CH(CH$_3$)CH$_2$CH$_2$— or the like; a pentamethylene group [—CH$_2$CH$_2$CH$_2$CH$_2$CH$_2$—]; and the like.

Further, a part of the methylene group in the alkylene group as V$^{101}$ and V$^{102}$ may be substituted with a divalent aliphatic cyclic group having 5 to 10 carbon atoms. The aliphatic cyclic group is preferably a divalent group formed by further removing one hydrogen atom from the cyclic aliphatic hydrocarbon group as Ra'$^3$ in Formula (a1-r-1) (monocyclic aliphatic hydrocarbon group, polycyclic aliphatic hydrocarbon group), and more preferably a cyclohexylene group, a 1,5-adamantylene group or a 2,6-adamantylene group.

Among these, Y$^{101}$ is preferably a single bond, an ester bond (—C(=O)—O—), or an oxycarbonyl group (—O—C(=O)=).

In Formula (b1-1-an1), V$^{101}$ represents a single bond, an alkylene group, or a fluorinated alkylene group. The alkylene group and the fluorinated alkylene group as V$^{101}$ preferably have 1 to 4 carbon atoms. Examples of the fluorinated alkylene group as V$^{101}$ include a group in which some or all hydrogen atoms in the alkylene group as V$^{101}$ have been substituted with fluorine atoms. Among these examples, as V$^{101}$, a single bond or a fluorinated alkylene group having 1 to 3 carbon atoms is preferable.

In Formula (b1-1-an1), R$^{102}$ represents a fluorine atom or a fluorinated alkyl group having 1 to 5 carbon atoms. R$^{102}$ represents preferably a fluorine atom or a perfluoroalkyl group having 1 to 5 carbon atoms and more preferably a fluorine atom.

Anion Represented by Formula (b1-1-an2)

In Formula (b1-1-an2), R$^{104}$ and R$^{105}$ each independently represent a cyclic group which may have a substituent, a chain-like alkyl group which may have a substituent or a chain-like alkenyl group which may have a substituent, and examples thereof are the same as those described above as R$^{101}$ in Formula (b1-1-an1). Here, R$^{104}$ and R$^{105}$ may be bonded to each other to form a ring.

As R$^{104}$ and R$^{105}$, a chain-like alkyl group which may have a substituent is preferable, and a linear or branched alkyl group or a linear or branched fluorinated alkyl group is more preferable.

The chain-like alkyl group has preferably 1 to 10 carbon atoms, more preferably 1 to 7 carbon atoms, and still more preferably 1 to 3 carbon atoms. It is preferable that the number of carbon atoms in the chain-like alkyl group as R$^{104}$ and R$^{105}$ is smaller because the solubility in a solvent for a resist is also excellent in the range of the number of carbon atoms. Further, in the chain-like alkyl group as R$^{104}$ and R$^{105}$, it is preferable that the number of hydrogen atoms substituted with fluorine atoms is as large as possible because the acid strength increases. The proportion of fluorine atoms in the chain-like alkyl group, that is, the fluorination ratio is preferably in a range of 70% to 100% and more preferably in a range of 90% to 100%, and it is most preferable that the chain-like alkyl group is a perfluoroalkyl group in which all hydrogen atoms are substituted with fluorine atoms.

In Formula (b1-1-an2), V$^{102}$ and V$^{103}$ each independently represent a single bond, an alkylene group, or a fluorinated alkylene group, and has the same definition as that for V$^{101}$ in Formula (b1-1-an1).

In Formula (b1-1-an2), L$^{101}$ and L$^{102}$ each independently represent a single bond or an oxygen atom.

Anion Represented by Formula (b1-1-an3)

In Formula (b1-1-an3), R$^{106}$ to R$^{108}$ each independently represent a cyclic group which may have a substituent, a chain-like alkyl group which may have a substituent or a chain-like alkenyl group which may have a substituent, and examples thereof are the same as those described above as R$^{101}$ in Formula (b1-1-an1).

In Formula (b1-1-an3), L$^{103}$ to L$^{105}$ each independently represent a single bond, —CO— or —SO$_2$—.

In Formula (bd1), among these, X$^-$ is preferably an anion represented by Formula (b1-1-an1).

Preferred specific examples of the anion represented by Formula (b1-1-an1) are shown below.

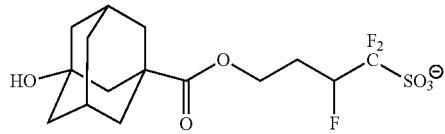

(an-bd-1)

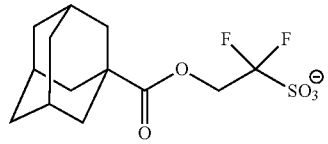

(an-bd-2)

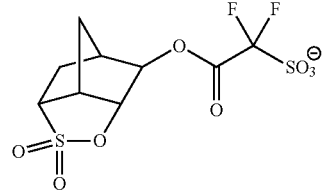

(an-bd-3)

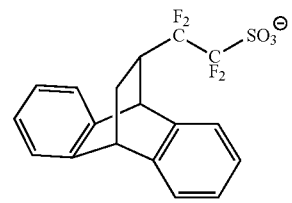

(an-bd-4)

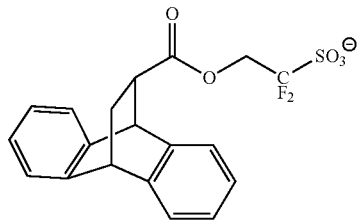

(an-bd-5)

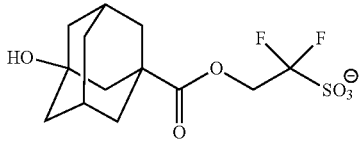

(an-bd-6)

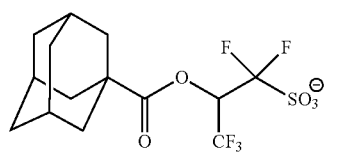

(an-bd-7)

Anion Moiety of Component (D1)

In a case where the component (BD1) is used as an acid diffusion control agent, any known anion as the anion moiety of acid diffusion control agent component for resist composition can be appropriately used as X⁻ in Formula (bd1).

Examples of X⁻ include an anion represented by Formula (d1-1-an1), an anion represented by Formula (d1-1-an2), or an anion represented by Formula (d1-1-an3).

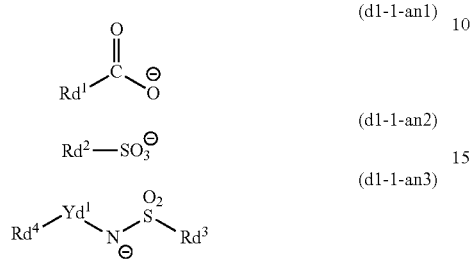

[In the formulae, $Rd^1$ to $Rd^4$ represent a cyclic group which may have a substituent, a chain-like alkyl group which may have a substituent or a chain-like alkenyl group which may have a substituent. Here, the carbon atom adjacent to the sulfur), an atom group which may have a substituent. Here, the carbon atom adjacent to the sulfur atom in $Rd^2$ in Formula (d1-1-an2) has no fluorine atom bonded thereto. $Yd^1$ represents a single bond or a divalent linking group.]

In Formula (b1-1-an1), $Rd^1$ represents a cyclic group which may have a substituent, a chain-like alkyl group which may have a substituent, or a chain-like alkenyl group which may have a substituent. Examples thereof are the same as those for $R^{101}$ in Formula (b1-1-an1). Among these, as $Rd^1$, a cyclic group which may have a substituent is preferable, and an aromatic hydrocarbon group which may have a substituent is more preferable.

Preferred specific examples of the anion represented by Formula (d1-1-an1) are shown below.

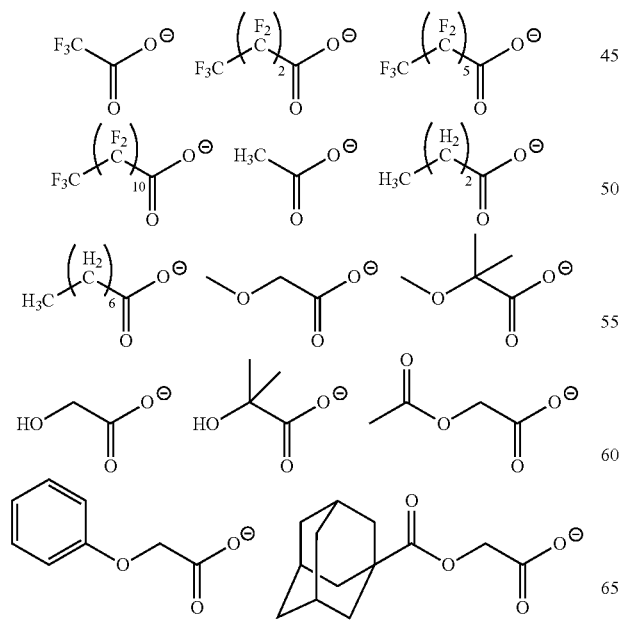

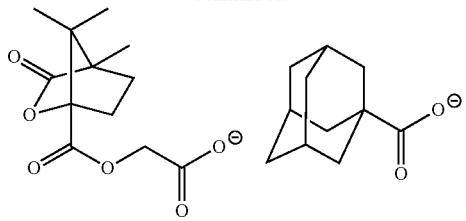

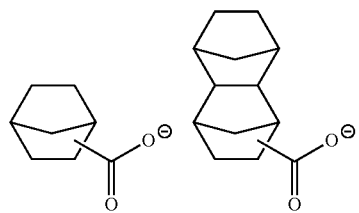

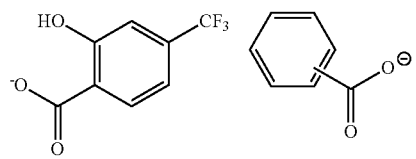

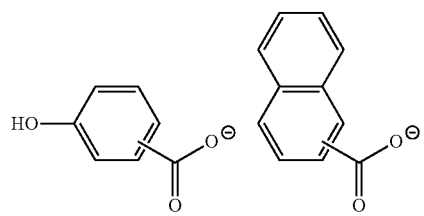

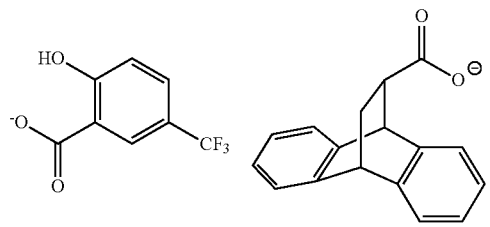

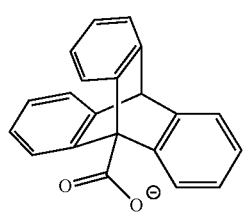

In Formula (d1-1-an2), $Rd^2$ represents a cyclic group which may have a substituent, a chain-like alkyl group which may have a substituent, or a chain-like alkenyl group which may have a substituent. Examples thereof are the same as those for $R^{101}$ in Formula (b1-1-an1). Here, the carbon atom adjacent to the sulfur atom in $Rd^2$ has no fluorine atom bonded thereto (the carbon atom adjacent to the sulfur atom in $Rd^2$ is not substituted with a fluorine atom).

Preferred specific examples of the anion represented by Formula (d1-1-an2) are shown below.

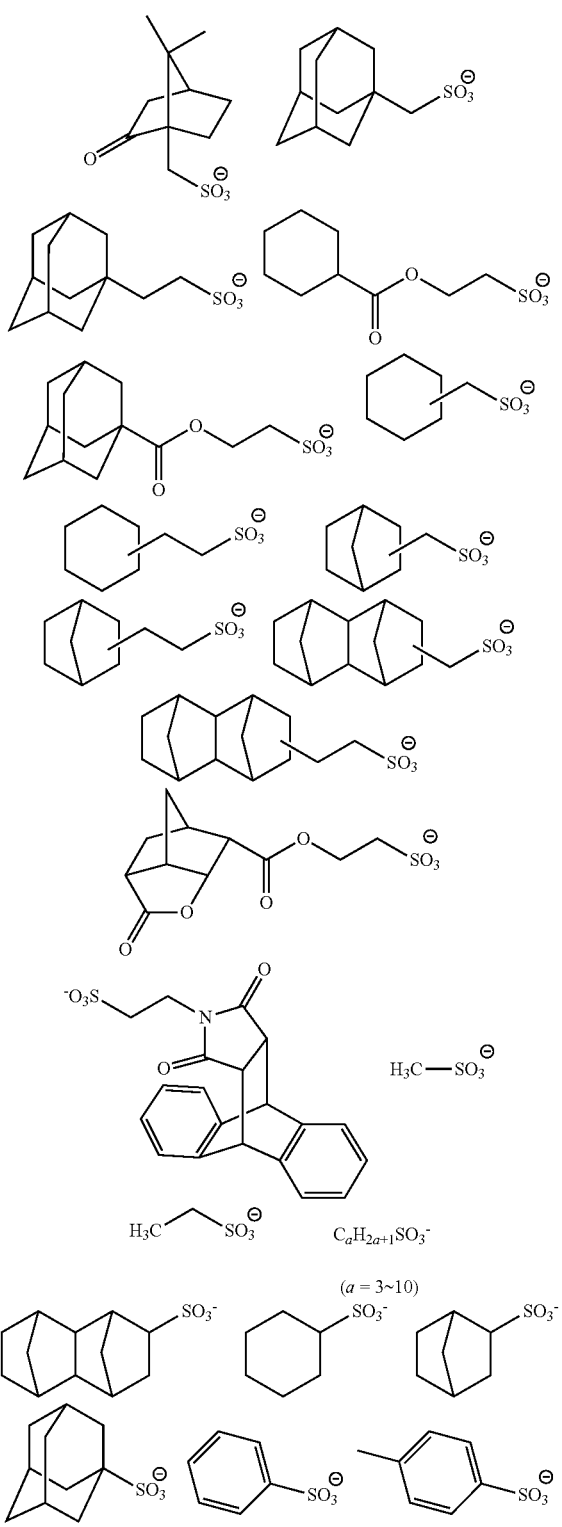

In Formula (d1-1-an3), $Rd^3$ and $Rd^4$ represent a cyclic group which may have a substituent, a chain-like alkyl group which may have a substituent, or a chain-like alkenyl group which may have a substituent. Examples thereof are the same as those for $R^{101}$ in Formula (b1-an1).

In Formula (d1-1-an3), $Yd^1$ represents a single bond or a divalent linking group.

The divalent linking group as $Yd^1$ is not particularly limited, and examples thereof include a divalent hydrocarbon group (an aliphatic hydrocarbon group or an aromatic hydrocarbon group) which may have a substituent and a divalent linking group containing a hetero atom. The divalent linking groups are the same as described above as the divalent hydrocarbon group which may have a substituent and the divalent linking group containing a hetero atom explained above as the divalent linking group as $Ya^{x1}$ in Formula (a10-1).

As $Yd^1$, a carbonyl group, an ester bond, an amide bond, an alkylene group, or a combination of these is preferable. As the alkylene group, a linear or branched alkylene group is more preferable, and a methylene group or an ethylene group is still more preferable.

Preferred specific examples of the anion represented by Formula (d1-1-an3) are shown below.

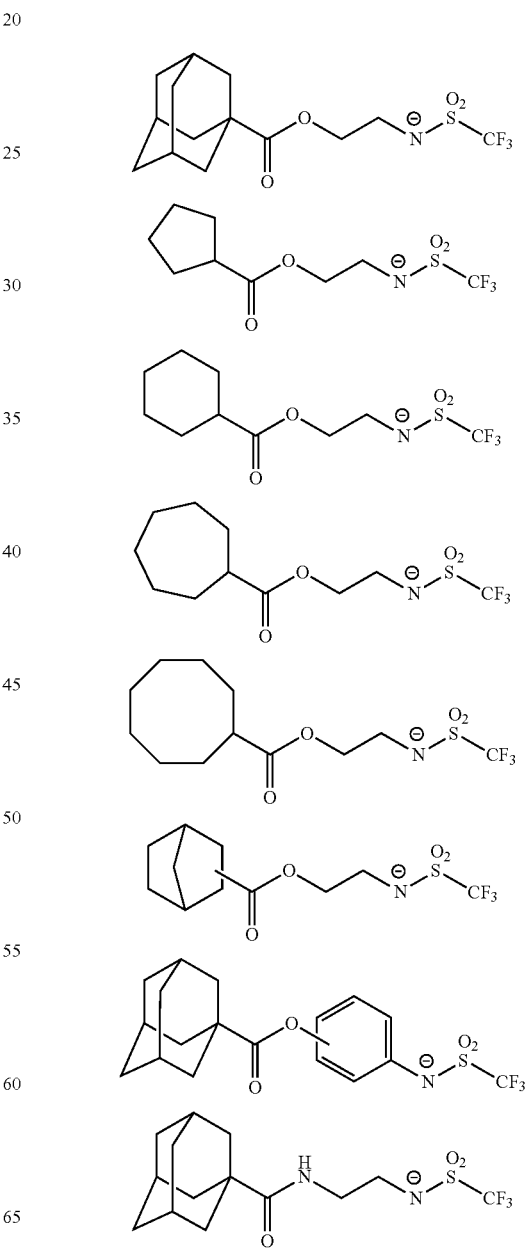

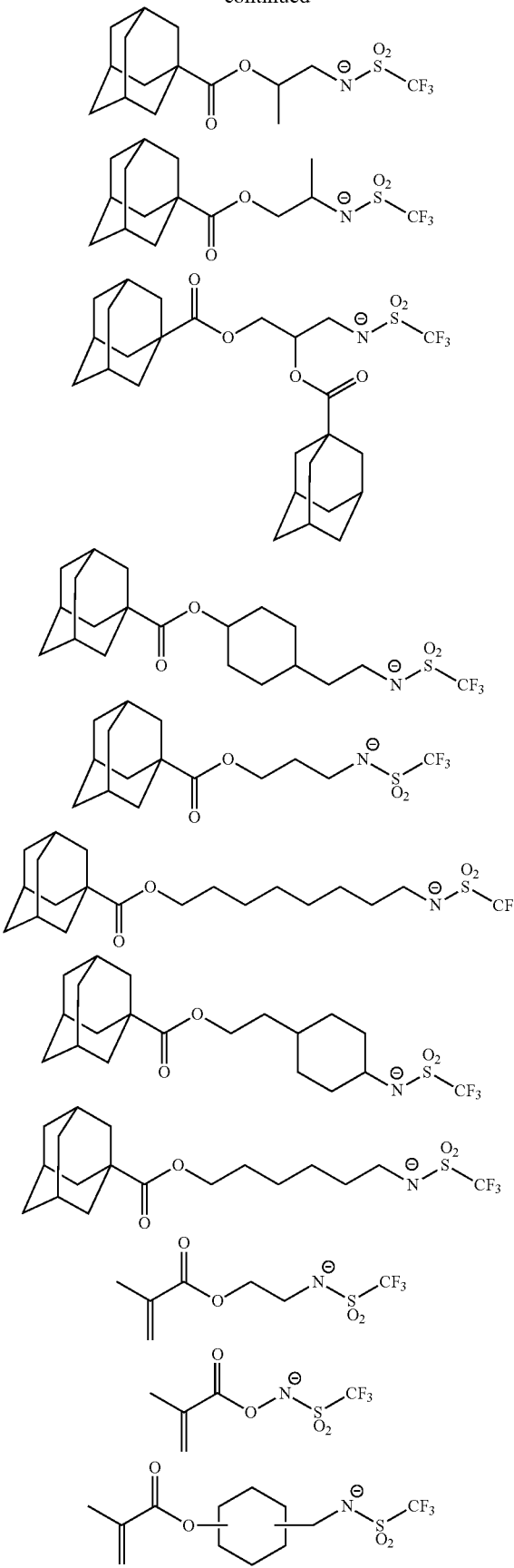

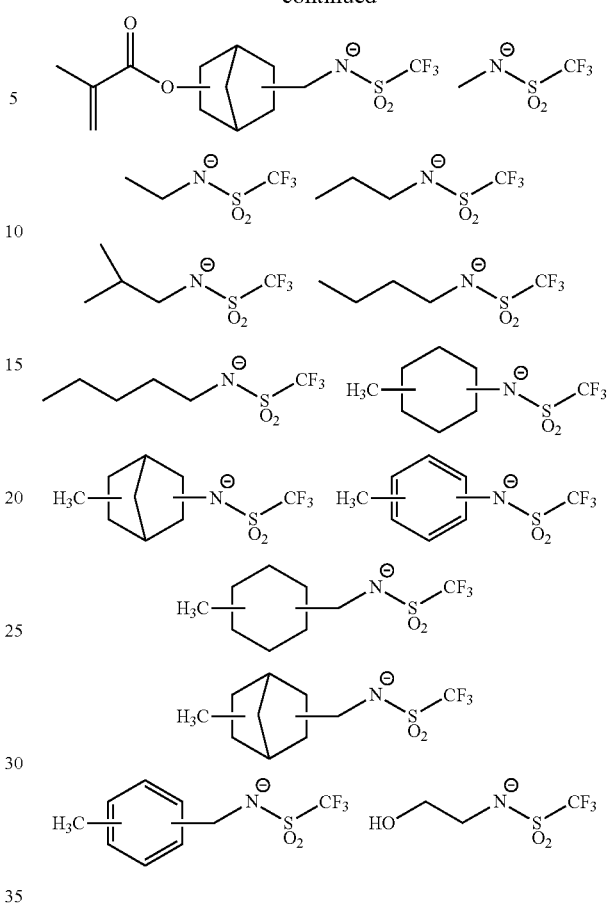

In the resist composition of the present embodiment, the component (BD1) is more preferably a compound represented by Formula (bd1-1).

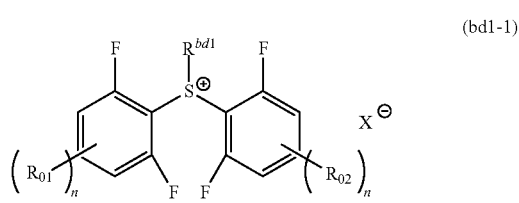

[In the formula, $R^{bd1}$ represents an aryl group which may have a substituent. $R_{01}$ and $R_{02}$ each independently represent a substituent; each n independently represents an integer of 0 to 3. $X^-$ represents a counter anion.]

In Formula (bd1-1), $R^{bd1}$ is the same as described in the explanation for $R^{bd1}$ to $R^{bd3}$ in Formula (bd1).

Examples of $R_{01}$ and $R_{02}$ are the same as the substituents described in the explanation of $R^{bd1}$ to $R^{bd3}$ in Formula (bd1).

Each n independently represents an integer of 0 to 3.

In Formula (bd1-1), $X^-$ is the same as those described for $X^-$ in Formula (bd1).

In the resist composition of the present embodiment, the component (B1) is preferably an acid generator represented by Formula (b0-1).

(b0-1)
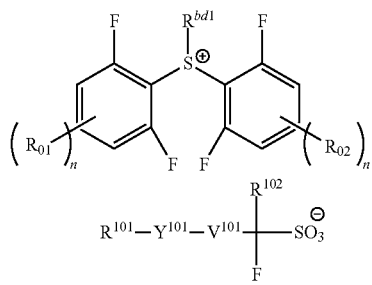

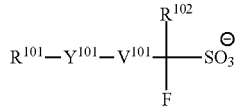

[In the formula, $R^{bd1}$ represents an aryl group which may have a substituent. $R_{01}$ and $R_{02}$ each independently represent a substituent; each n independently represents an integer of 0 to 3. $R^{101}$ represents a cyclic group which may have a substituent, a chain-like alkyl group which may have a substituent, or a chain-like alkenyl group which may have a substituent. $R^{102}$ represents a fluorinated alkyl group having 1 to 5 carbon atoms or a fluorine atom. $Y^{101}$ represents a divalent linking group containing an oxygen atom or a single bond. $V^{101}$ represents a single bond, an alkylene group, or a fluorinated alkylene group.]

In Formula (b0-1), the anion moiety is the same as described in the explanation of Formula (b1-1-an1), and the cation moiety is the same as described in the explanation of the cation moiety in Formula (bd1-1).

Specifically, as the component (B1), acid generators in various combinations of the cation represented by any of Formulae (ca-bd-1) to (ca-bd-15) and the anion represented by Formula (b1-1-an1) are preferable, acid generators in various combinations of the cation represented by any of Formulae (ca-bd-1) to (ca-bd-11) and the anion represented by Formula (b1-1-an1) are more preferable, and acid generators in various combinations of the cation represented by any of Formulae (ca-bd-1) to (ca-bd-4) and the anion represented by Formula (b1-1-an1) are still more preferable.

Specific examples of the component (B1) are shown below, but the invention is not limited thereto.

(B1-1)
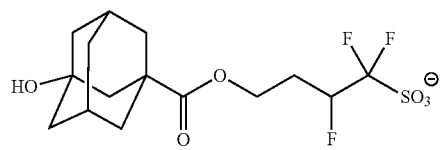

(B1-2)
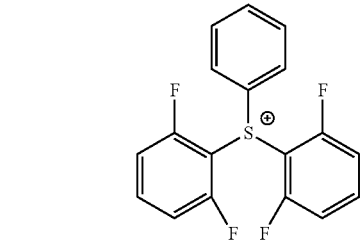

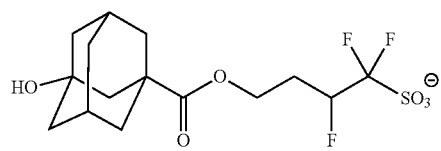

-continued
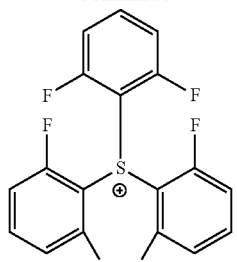

(B1-3)
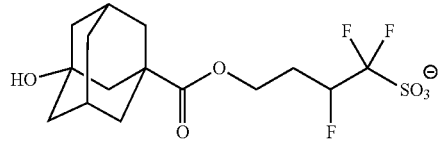

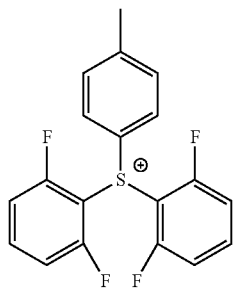

(B1-4)
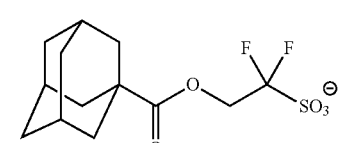

(B1-5)
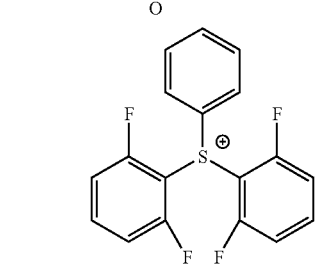

-continued

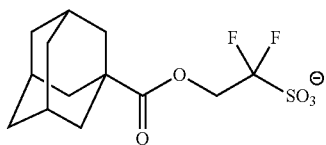
(B1-6)

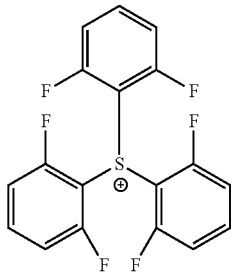
(B1-7)

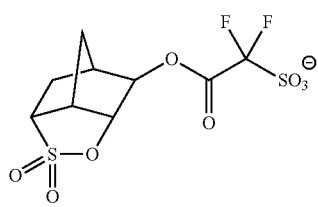
(B1-8)

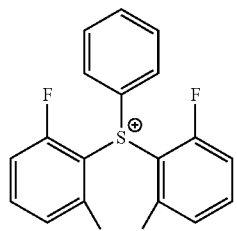

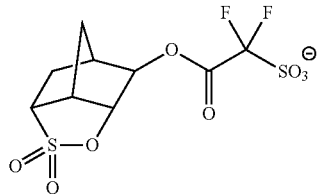
(B1-9)

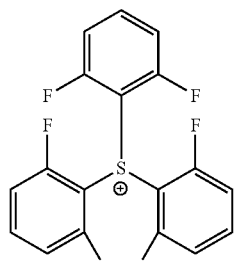

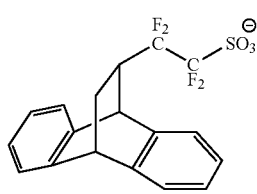
(B1-10)

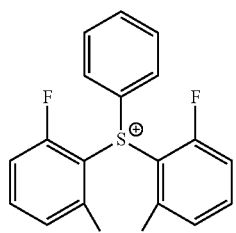

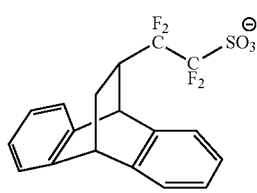

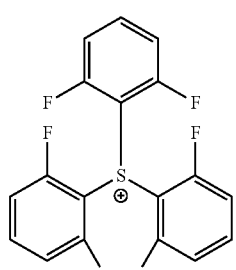

In the resist composition of the present embodiment, the component (B1) may be used alone or in combination of two or more kinds thereof.

The content of the component (B1) in the resist composition of the present embodiment is preferably in a range of 5 to 65 parts by mass, more preferably in a range of 5 to 55 parts by mass, still more preferably in a range of 10 to 45 parts by mass, and particularly preferably in a range of 10 to 40 parts by mass with respect to 100 parts by mass of the component (A).

The proportion of the component (B1) in the entire acid generator component (B) that generates an acid acting on the component (A) in the resist composition is, for example, 50% by mass or more, preferably 70% by mass or more, and more preferably 95% by mass or more. 100% by mass of the component (B1) may be allowable.

In a case where the content of the component (B1) is greater than or equal to the lower limit of the above-described preferable range, lithography characteristics such as sensitivity, resolution, line width roughness (LWR) reduction, or shape are further improved at the time of forming a resist pattern. Meanwhile, in a case where the content of the component (B1) is less than or equal to the upper limit of the preferable range, a uniform solution is easily obtained and the storage stability of a resist composition is further increased at the time of dissolving each component of the resist composition in an organic solvent.

In the resist composition of the present embodiment, the component (D1) is preferably an acid diffusion control agent represented by Formula (d0-1).

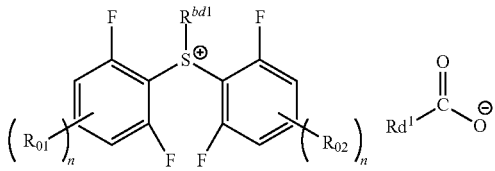
(d0-1)

[In the formula, $R^{bd1}$ represents an aryl group which may have a substituent. $R_{o1}$ and $R_{o2}$ each independently represent a substituent; each n independently represents an integer of 0 to 3. $Rd^1$ represents a cyclic group which may have a substituent, a chain-like alkyl group which may have a substituent or a chain-like alkenyl group which may have a substituent.]

In Formula (d0-1), the anion moiety is the same as described in the explanation of Formula (d1-1-an1), and the cation moiety is the same as described in the explanation of the cation moiety in Formula (bd1-1).

Specifically, as the component (D1), acid diffusion control agents in various combinations of the cation represented by any of Formulae (ca-bd-1) to (ca-bd-15) and the anion represented by Formula (d1-1-an1) are preferable, acid diffusion control agents in various combinations of the cation represented by any of Formulae (ca-bd-1) to (ca-bd-11) and the anion represented by Formula (d1-1-an1) are more preferable, and acid diffusion control agents in various combinations of the cation represented by any of Formulae (ca-bd-1) to (ca-bd-4) and the anion represented by Formula (d1-1-an1) are still more preferable.

Specific examples of the component (D1) are shown below, but the invention is not limited thereto.

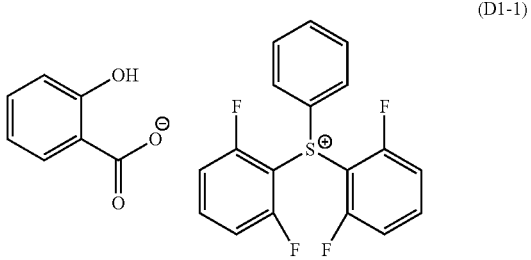 [SMILES: O=C([O-])c1ccccc1O ; Fc1cccc(F)c1[S+](c1ccccc1)c1c(F)cccc1F]

(D1-1)

In the resist composition of the present embodiment, the component (D1) may be used alone or in combination of two or more kinds thereof.

The content of the component (D1) in the resist composition of the present embodiment is preferably in a range of 1 to 35 parts by mass, more preferably in a range of 2 to 25 parts by mass, still more preferably in a range of 3 to 20 parts by mass, and particularly preferably in a range of 3 to 15 parts by mass with respect to 100 parts by mass of the component (A).

The proportion of the component (D1) in the entire base component (D) that traps an acid generated from the component (B) upon exposure (controlling acid diffusion) in the resist composition is, for example, 50% by mass or more, preferably 70% by mass or more, and more preferably 95% by mass or more. 100% by mass of the component (D1) may be allowable.

In addition, the proportion of the component (D1) in the whole component (D) in a case where the resist composition includes the component (B1) is not specifically limited, and may be appropriately adjusted in the range of 0% by mass to 100% by mass.

In a case where the content of the component (D1) is greater than or equal to the lower limit of the preferable range, excellent lithography characteristics and an excellent resist pattern shape can be more reliably obtained. On the other hand, in a case where the content of the component (D1) is lower than or equal to the upper limit of the preferable range, the component (D1) and other components can be balanced, and various lithography characteristics are enhanced.

<Optional Components>

The resist composition of the present embodiment may further contain components (optional components) other than the component (A) and the compound (BD1) (the component (B1) and the component (D1)) described above.

Examples of such optional components include the following components (B2), (D2), (D3), (E), (F), and (S).

<<Component (B2)>>

The resist composition of the present embodiment may further contain an acid generator component (hereinafter, referred to as a "component (B2)") other than the component (B1) in a range not damaging the effects of the present invention.

The component (B2) is not particularly limited, and those which have been proposed as an acid generator for a chemically amplified resist composition in the related art can be used.

Examples of these acid generators are numerous and include onium salt-based acid generators such as iodonium salts, sulfonium salts, or the like; oxime sulfonate-based acid generators; diazomethane-based acid generators such as bisalkyl or bisaryl sulfonyl diazomethanes, poly(bis-sulfonyl)diazomethanes, or the like; nitrobenzylsulfonate-based acid generators; iminosulfonate-based acid generators; disulfone-based acid generators; and the like.

As the onium salt-based acid generator, a compound represented by Formula (b-1) (hereinafter, also referred to as a "component (b-1)"), a compound represented by Formula (b-2) (hereinafter, also referred to as a "component (b-2)") or a compound represented by Formula (b-3) (hereinafter, also referred to as a "component (b-3)") can be used.

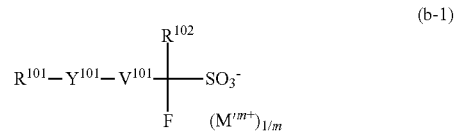

(b-1)

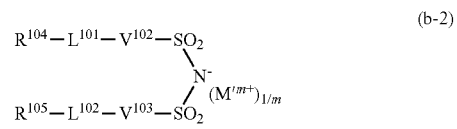

(b-2)

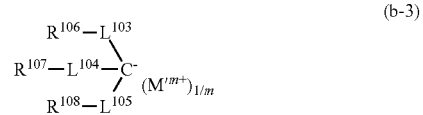

(b-3)

[In the formulae, $R^{101}$ and $R^{104}$ to $R^{108}$ each independently represent a cyclic group which may have a substituent, a chain-like alkyl group which may have a substituent, or a chain-like alkenyl group which may have a substituent. $R^{104}$ and $R^{105}$ may be bonded to each other to form a ring. $R^{102}$ represents a fluorine atom or a fluorinated alkyl group having 1 to 5 carbon atoms. $Y^{101}$ represents a single bond or a divalent linking group containing an oxygen atom. $V^{101}$ to $V^{103}$ each independently represent a single bond, an alkylene group, or a fluorinated alkylene group. $L^{101}$ and $L^{102}$ each independently represent a single bond or an oxygen atom. $L^{103}$ to $L^{105}$ each independently represent a single bond, —CO—, or —SO$_2$—. m represents an integer of 1 or more and $M'^{m+}$ represents an m-valent onium cation.]

[Cation Moiety]

In Formulae (b-1), (b-2) and (b-3), m represents an integer of 1 or more, and $M'^{m+}$ represents an m-valent onium cation. Here, those same as the cation moiety of the compound (BD1) represented by Formula (bd1) are excluded.

Specific examples thereof include sulfonium cations and iodonium cations and include cations represented by Chemical Formulae (ca-1-1) to (ca-1-78), (ca-1-101) to (ca-1-149), (ca-2-1), (ca-2-2), (ca-3-1) to (ca-3-7), (ca-4-1), and (ca-4-2).

In chemical formulae, g1 represents a repeating number, and g1 represents an integer of 1 to 5. g2 represents a repeating number, and g2 represents an integer of 0 to 20. g3 represents a repeating number, and g3 represents an integer of 0 to 20. $R''^{201}$ represents a hydrogen atom or a substituent. Examples of the substituent include an alkyl group, a halogen atom, a halogenated alkyl group, a carbonyl group, a cyano group, an amino group, and an aryl group.

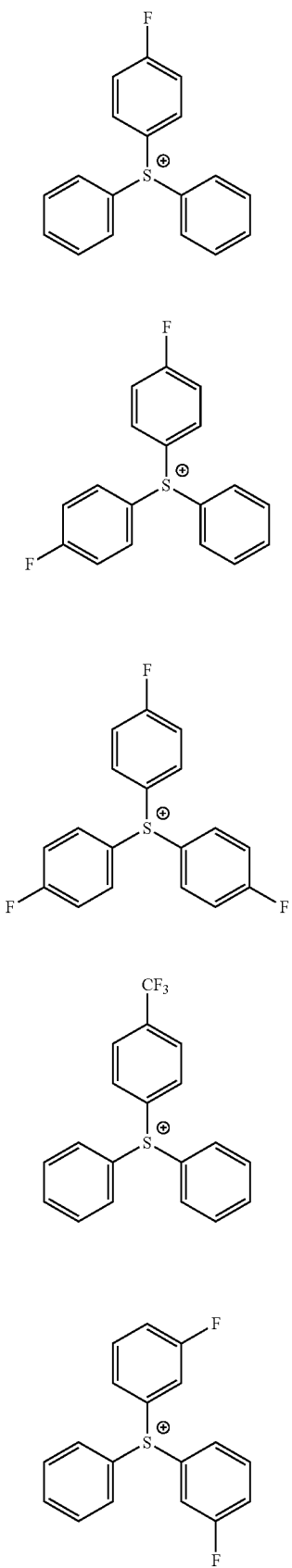
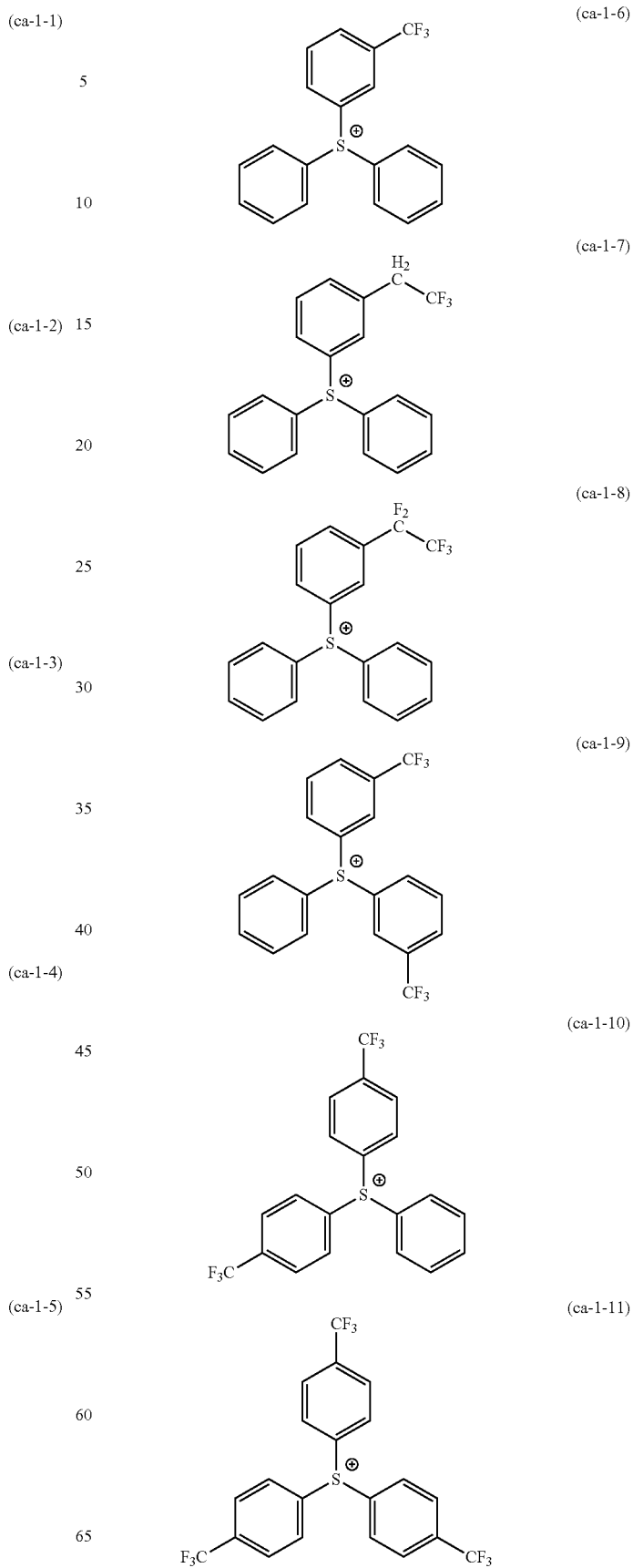

-continued
(ca-1-12)
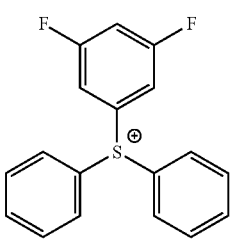
(ca-1-13)
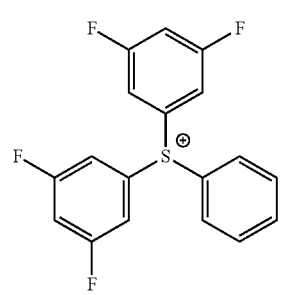
(ca-1-14)
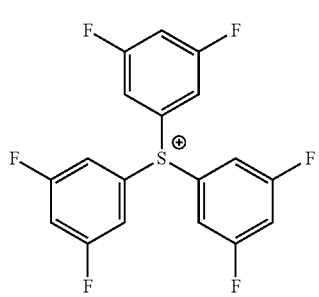
(ca-1-15)
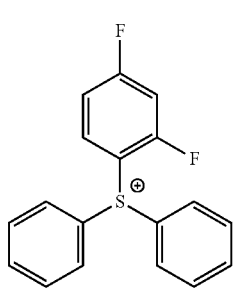
(ca-1-16)
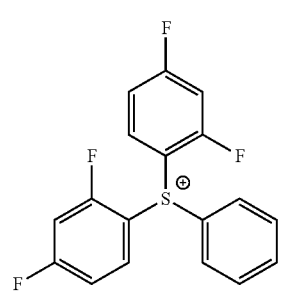
-continued
(ca-1-17)
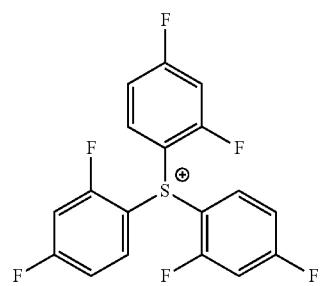
(ca-1-18)
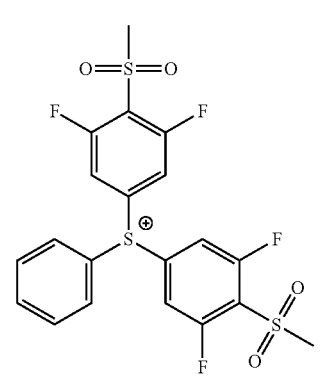
(ca-1-19)
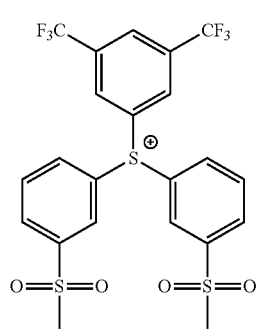
(ca-1-20)
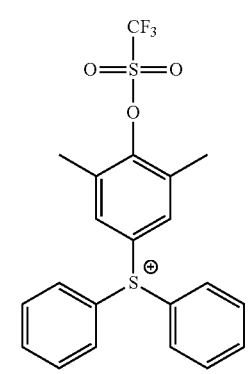

(ca-1-21) 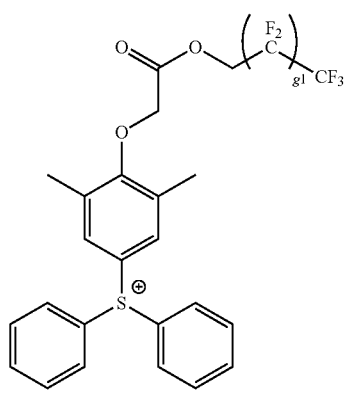
(ca-1-22) 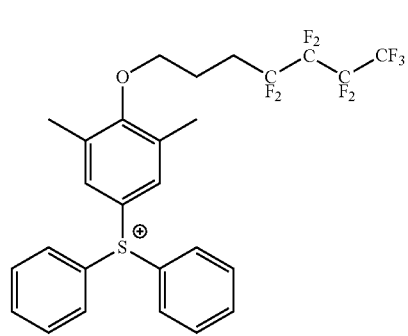
(ca-1-23) 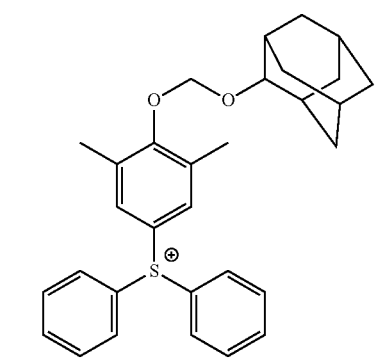
(ca-1-24) 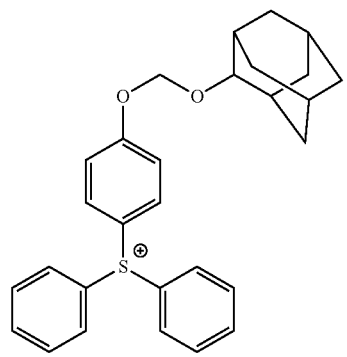
(ca-1-25) 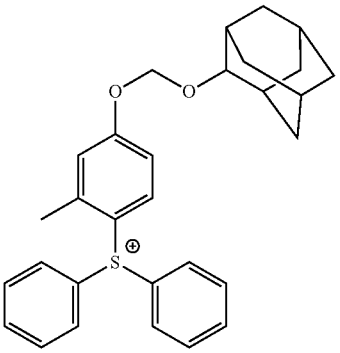
(ca-1-26) 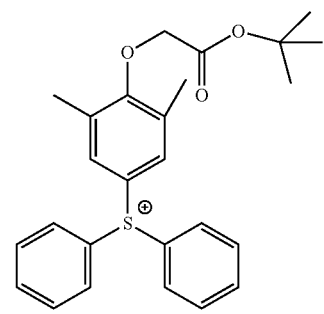
(ca-1-27) 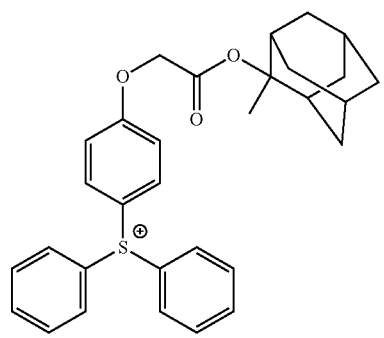
(ca-1-28) 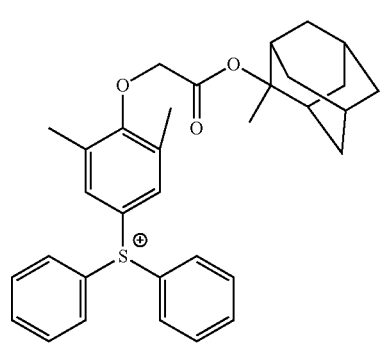

-continued
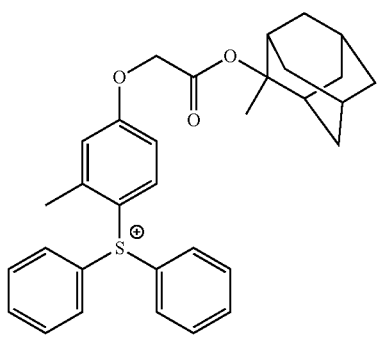
(ca-1-29)
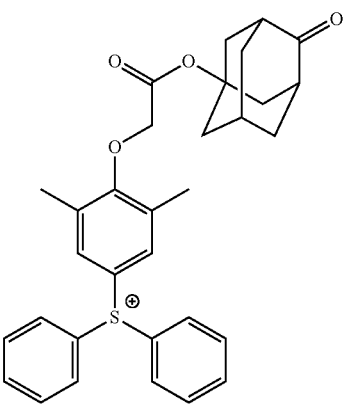
(ca-1-33)
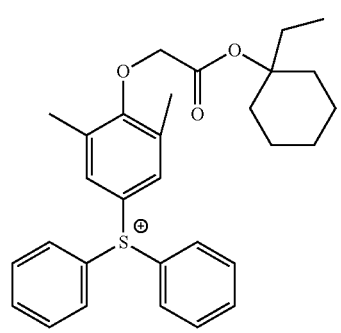
(ca-1-30)
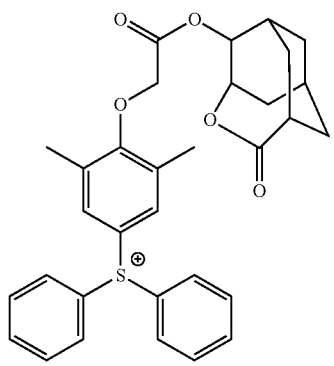
(ca-1-34)
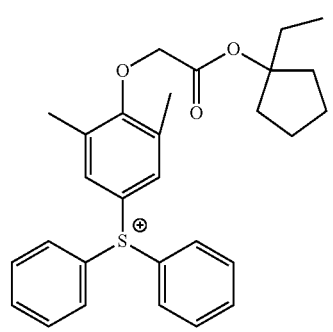
(ca-1-31)
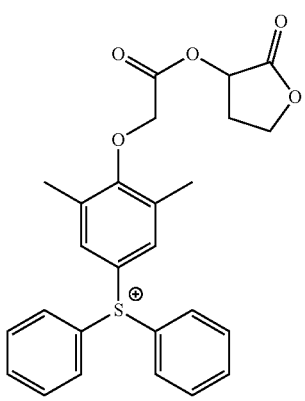
(ca-1-35)
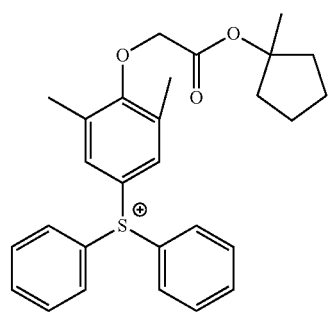
(ca-1-32)
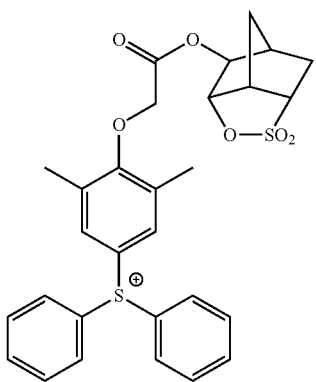
(ca-1-36)

-continued
(ca-1-37)
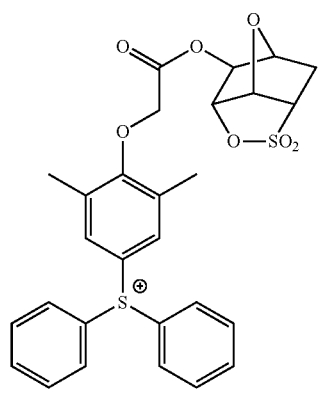
(ca-1-38)
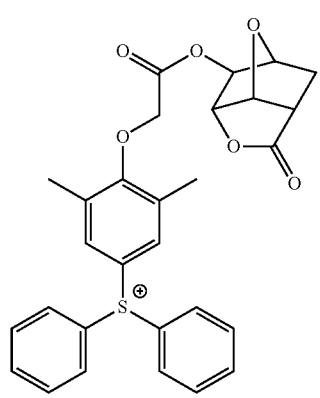
(ca-1-39)
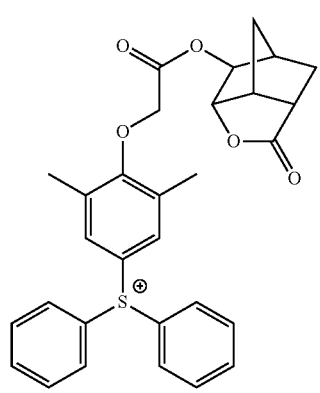
(ca-1-40)
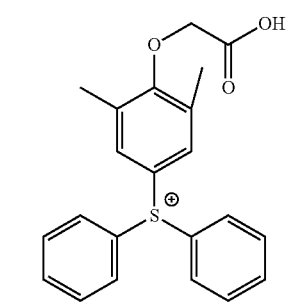
-continued
(ca-1-41)
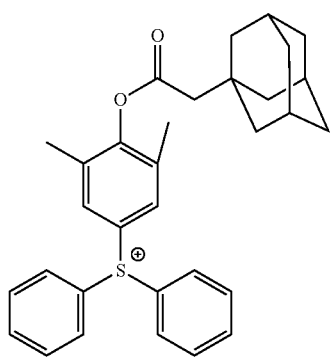
(ca-1-42)
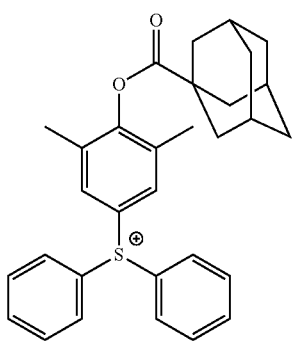
(ca-1-43)
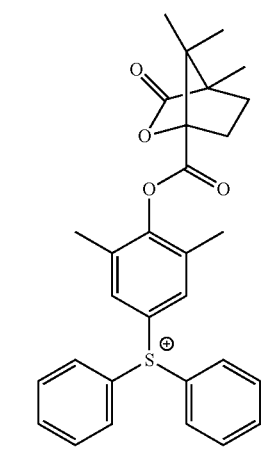
(ca-1-44)
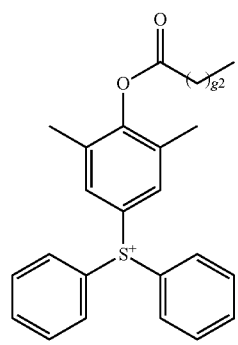

(ca-1-45)
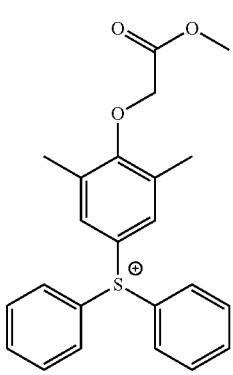
(ca-1-46)
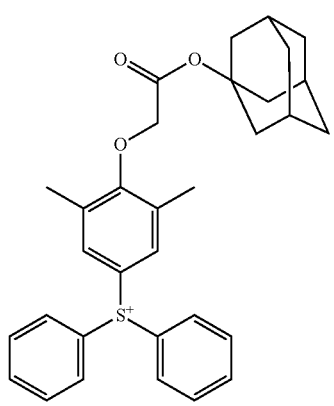
(ca-1-47)
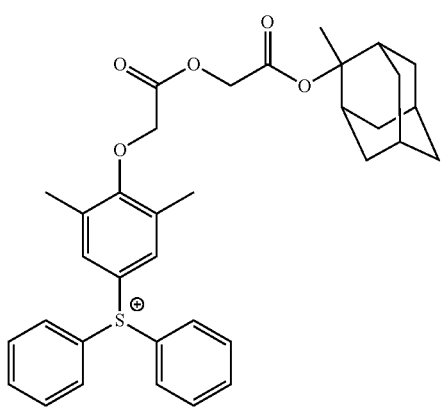
(ca-1-48)
(ca-1-49)
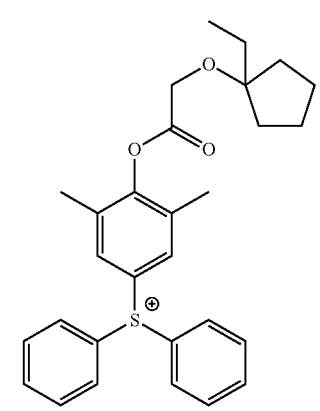
(ca-1-50)
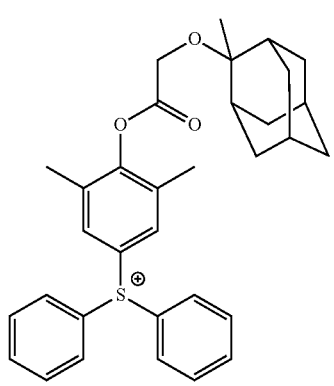
(ca-1-51)
(ca-1-52)
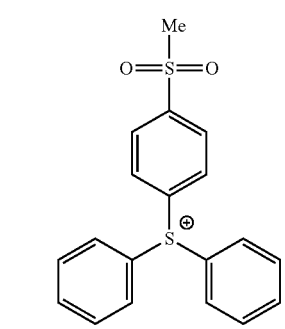

(ca-1-53)
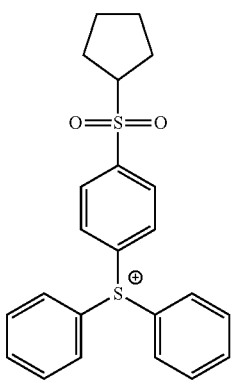
(ca-1-54)
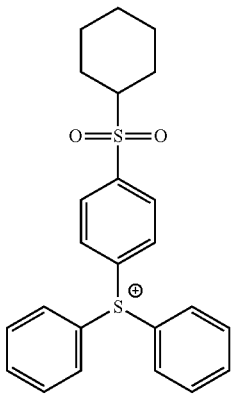
(ca-1-55)
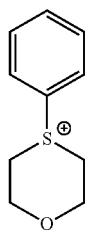
(ca-1-56)
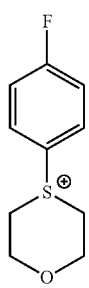
(ca-1-57)
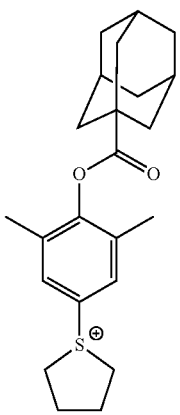
(ca-1-58)
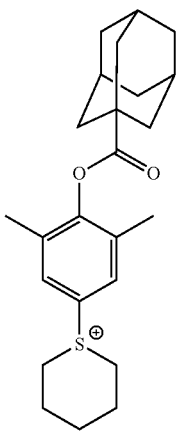
(ca-1-59)
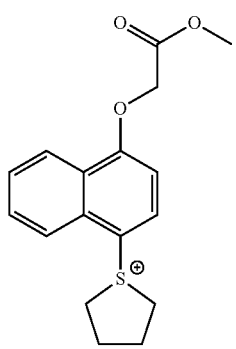
(ca-1-60)
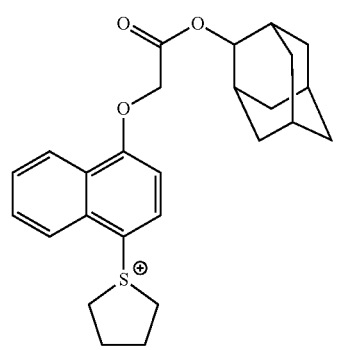

(ca-1-61) 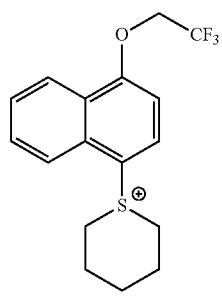
(ca-1-62) 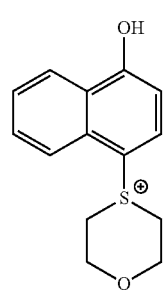
(ca-1-63) 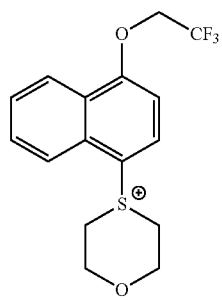
(ca-1-64) 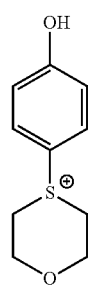
(ca-1-65) 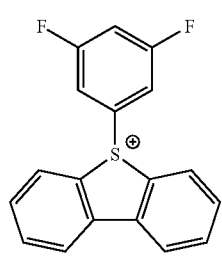
(ca-1-66) 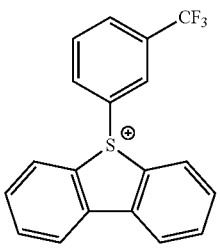
(ca-1-67) 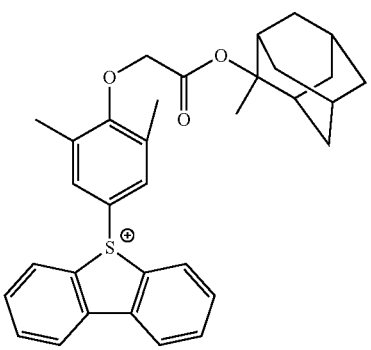
(ca-1-68) 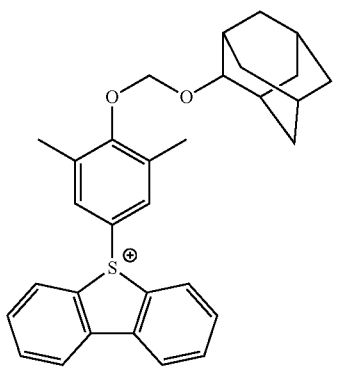
(ca-1-69) 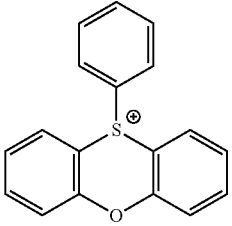
(ca-1-70) 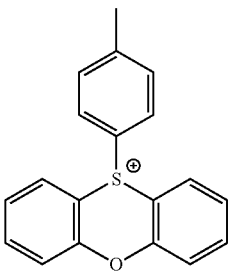

-continued
(ca-1-71)
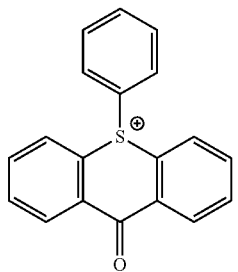
(ca-1-72)
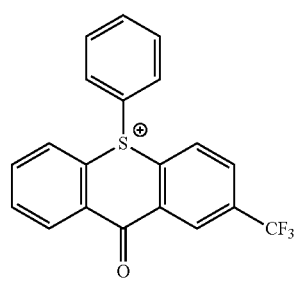
(ca-1-73)
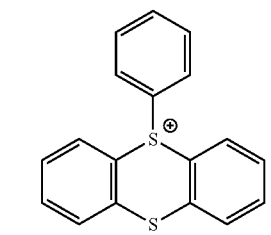
(ca-1-74)
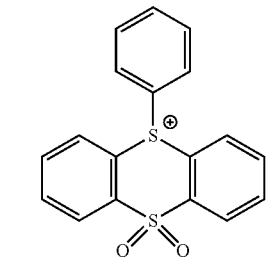
(ca-1-75)
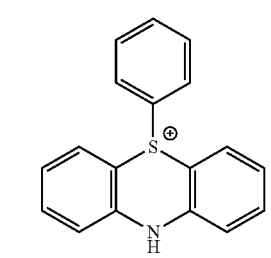
(ca-1-76)
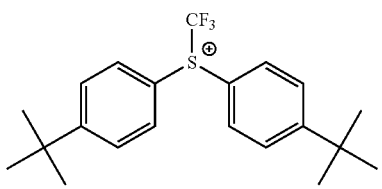
-continued
(ca-1-77)
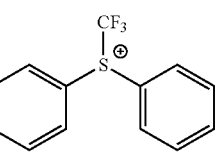
(ca-1-78)
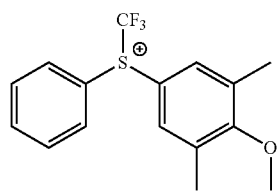
(ca-1-101)
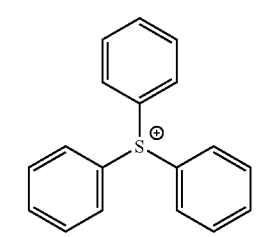
(ca-1-102)
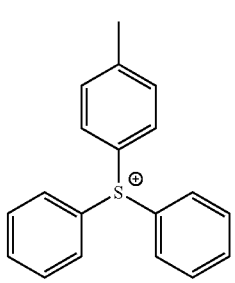
(ca-1-103)
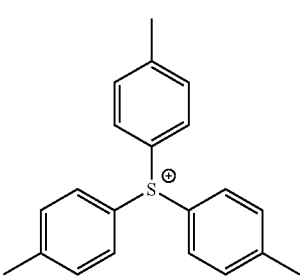
(ca-1-104)
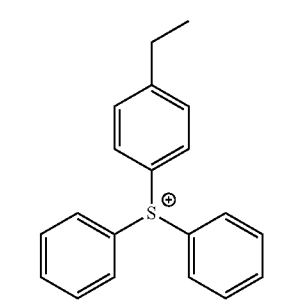

(ca-1-105)
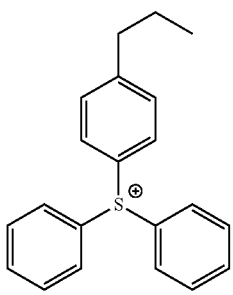
(ca-1-106)
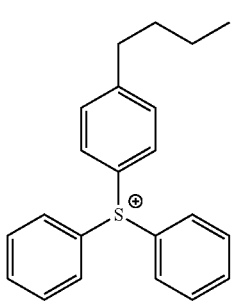
(ca-1-107)
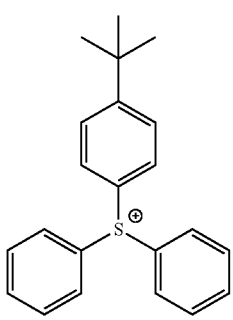
(ca-1-108)
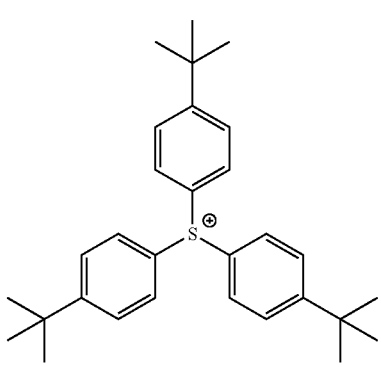
(ca-1-109)
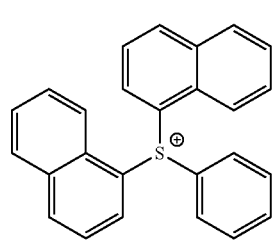
(ca-1-110)
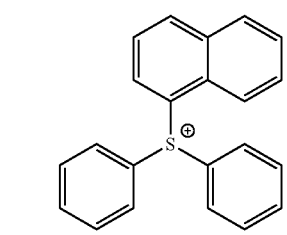
(ca-1-111)
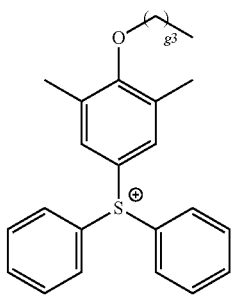
(ca-1-112)
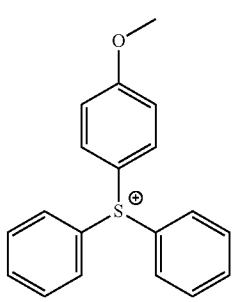
(ca-1-113)
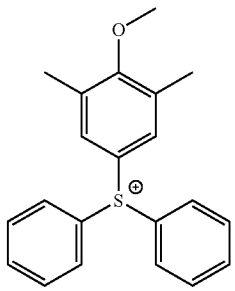
(ca-1-114)
(ca-1-115)
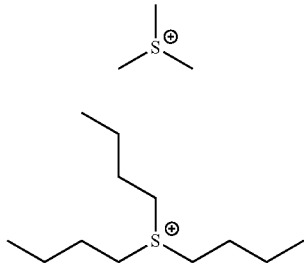
(ca-1-116)
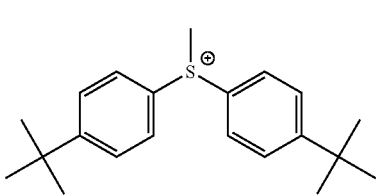

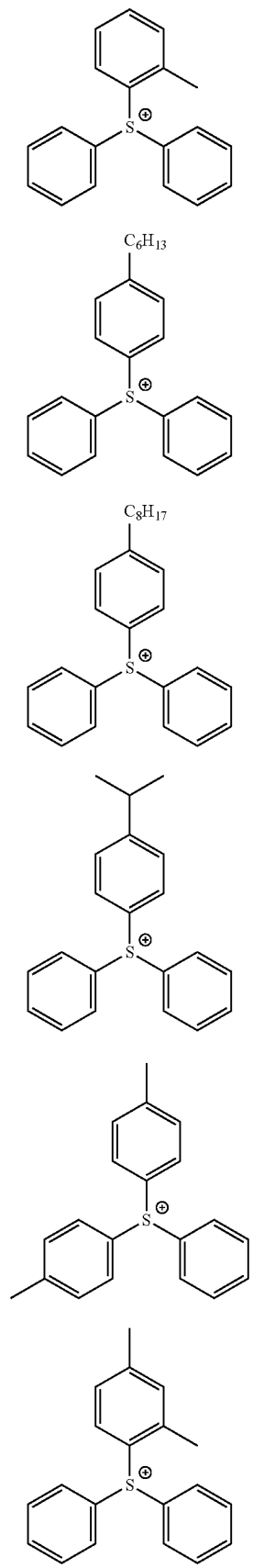
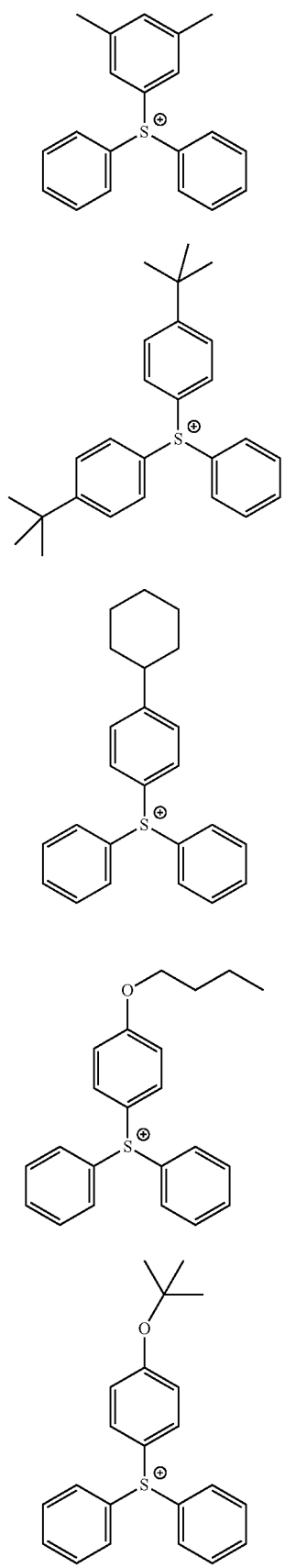

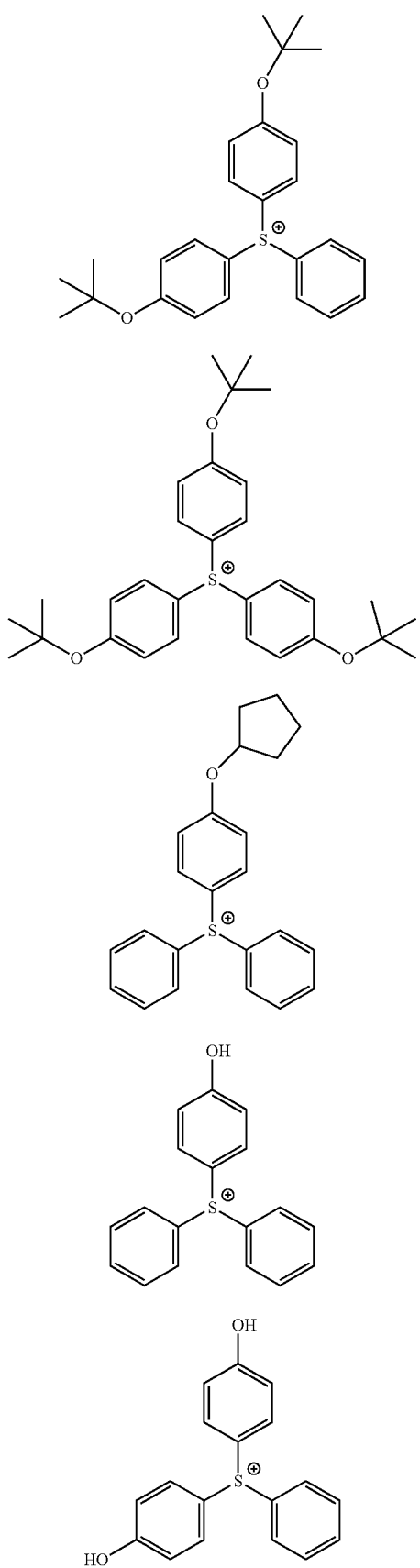
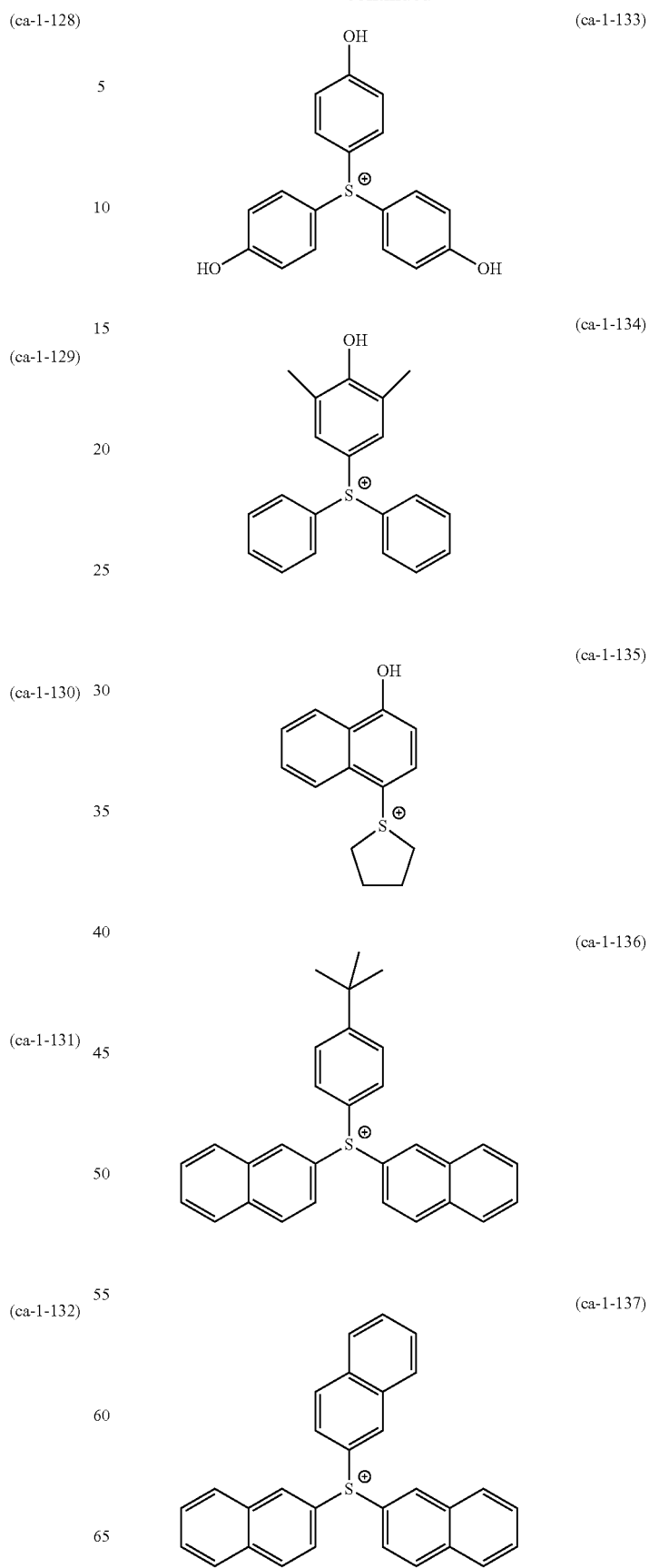

(ca-1-138)
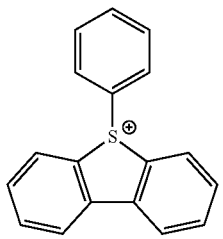
(ca-1-139)
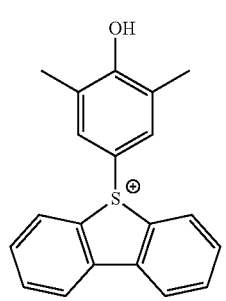
(ca-1-140)
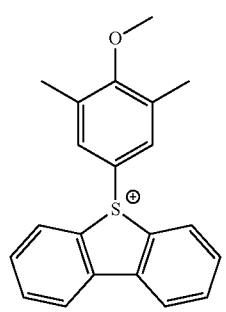
(ca-1-141)
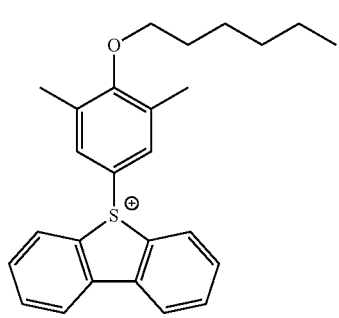
(ca-1-142)
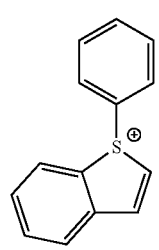
(ca-1-143)
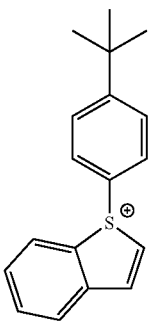
(ca-1-144)
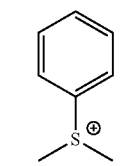
(ca-1-145)
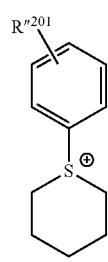
(ca-1-146)
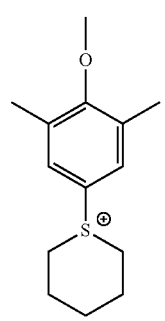
(ca-1-147)
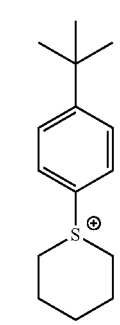

-continued (ca-1-148)
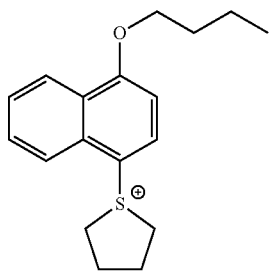

(ca-1-149)
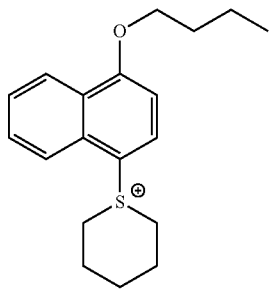

(ca-2-1)
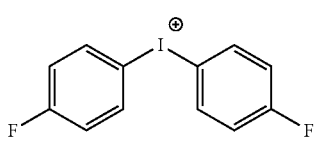

(ca-2-2)
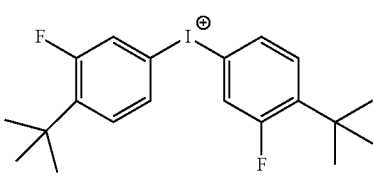

(ca-3-1)
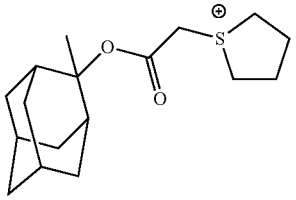

(ca-3-2)
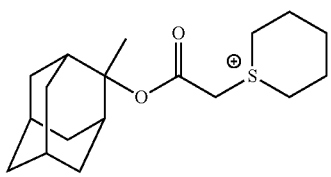

(ca-3-3)
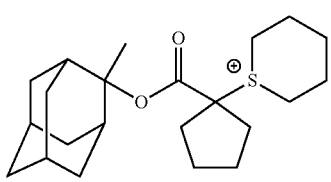

(ca-3-4)
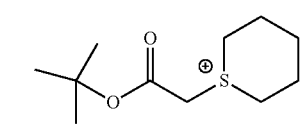

-continued (ca-3-5)
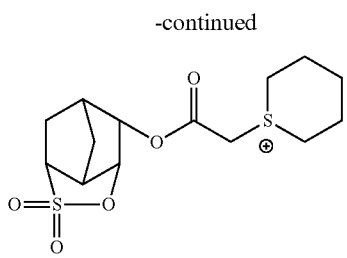

(ca-3-6)
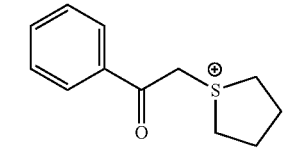

(ca-3-7)
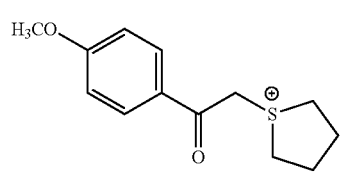

(ca-4-1)
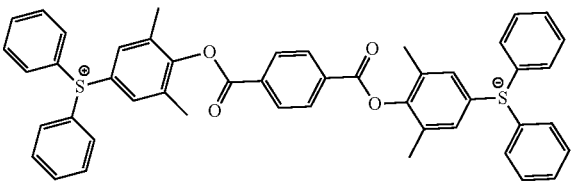

(ca-4-2)
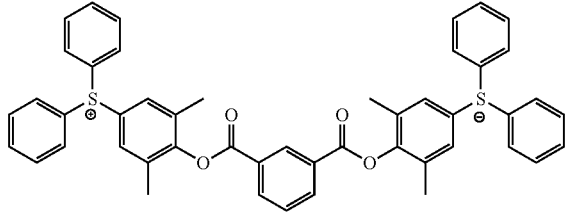

[Anion Moiety]

Examples of the anion moiety of the component (B2) are the same as described in the explanation of the anion moiety of the component (B1).

In the resist composition of the present embodiment, the component (B2) may be used alone or in combination of two or more kinds thereof.

In a case where the resist composition contains the component (B2), the content of the component (B2) in the resist composition is preferably 50 parts by mass or less, more preferably in a range of 1 to 40 parts by mass, and still more preferably in a range of 5 to 30 parts by mass with respect to 100 parts by mass of the component (A).

In a case where the resist composition contains the component (B2), the content of the component (B2) in the whole acid generator component (B) which generates an acid acting on the component (A) in the resist composition is preferably 50% by mass or less, more preferably 30% by mass or less, and still more preferably 0% by mass to 5% by mass. In addition, the proportion of the component (B2) in the whole component (B) in a case where the resist composition includes the component (D1) is not specifically limited, and may be appropriately adjusted in the range of 0% by mass to 100% by mass.

<<Component (D2)>>

The component (D2) is a base component and a photodisintegrable base (here, a component corresponding to the component (D1) is excluded), which is decomposed upon exposure and loses acid diffusion controllability.

In a case where a resist composition containing the component (D2) is obtained, the contrast between exposed portions and unexposed portions of the resist film can be further improved at the time of formation of a resist pattern.

The component (D2) is not particularly limited as long as it decomposes upon exposure and loses acid diffusion controllability, and is preferably one or more compounds selected from the group consisting of a compound represented by Formula (d2-1) (hereinafter referred to as a "component (d2-1)"), a compound represented by Formula (d2-2) (hereinafter referred to as a "component (d2-2)"), and a compound represented by Formula (d2-3) (hereinafter referred to as a "component (d2-3)").

The components (d2-1) to (d2-3) are decomposed and then lose the acid diffusion controllability (basicity), and therefore the components (d2-1) to (d2-3) cannot act as a quencher at the exposed portions of the resist film, whereas the components (d2-1) to (d2-3) acts as a quencher at the unexposed portions of the resist film.

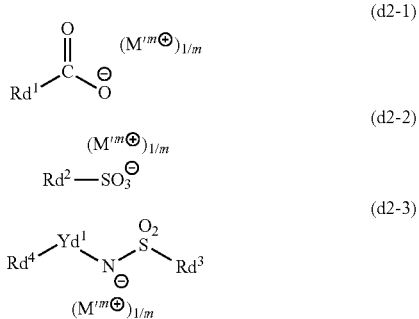

[In the formulae, $Rd^1$ to $Rd^4$ represent a cyclic group which may have a substituent, a chain-like alkyl group which may have a substituent or a chain-like alkenyl group which may have a substituent. Here, the carbon atom adjacent to the sulfur atom in $Rd^2$ in Formula (d2-2) has no fluorine atom bonded thereto. $Yd^1$ represents a single bond or a divalent linking group. m represents an integer of 1 or more and each $M'^{m+}$ independently represents an m-valent onium cation.]

[Cation Moiety]

In Formulae (d2-1) to (d2-3), $M'^{m+}$ represents an m-valent onium cation. The onium cation of $M'^{m+}$ can be appropriately selected from the same cations exemplified as $M'^{m+}$ in the Formulae (b-1) to (b-3) such that the onium cation of $M'^{m+}$ is different from the component (D1).

[Anion Moiety]

Examples of the anion moiety in Formulae (d2-1) to (d2-3) are the same as described in the explanation of the anion moiety of the component (D1).

The component (d2-1) may be used alone or in combination of two or more kinds thereof.

As the component (D2), only one of the components (d2-1) to (d2-3) described above or a combination of two or more kinds thereof may be used.

In a case where the resist composition contains the component (D2), the content of the component (D2) in the resist composition is preferably in a range of 0.5 to 10 parts by mass, more preferably in a range of 0.5 to 8 parts by mass, and still more preferably in a range of 1 to 6 parts by mass with respect to 100 parts by mass of the component (A).

In a case where the resist composition contains the component (D2), the content of the component (D2) in the entire base component (D) that traps an acid generated from the component (B) upon exposure (controlling acid diffusion) in the resist composition is, for example, 50% by mass or less, preferably 30% by mass or less, and more preferably 0% by mass to 5% by mass.

Preparation Method of Component (D2)

The preparation methods of the components (d2-1) and (d2-2) are not particularly limited, and the components (d2-1) and (d2-2) can be prepared by known methods.

Further, the preparation methods of the component (d2-3) are not particularly limited, and the component (d2-3) can be prepared in the same manner as disclosed in United States Patent Application, Publication No. 2012-0149916.

<<Component (D3)>>

The component (D3) is a base component and is a nitrogen-containing organic compound component (here, a component corresponding to the component (D1) or (D2) is excluded) that acts as an acid diffusion control agent in the resist composition.

The component (D3) is not particularly limited as long as it acts as an acid diffusion control agent and does not correspond to the components (D1) and (D2). Examples thereof include compounds including an anion moiety and a cation moiety, aliphatic amines and the like.

Examples of the compound including the anion moiety and the cation moiety as the component (D3) include those in which the cation moiety is an ammonium cation as the components (d2-1) to (d2-3). Examples of the ammonium cation include a cation (primary to quaternary ammonium cations) in which $NH_4^+$, or H bonded to its nitrogen atom is substituted with a hydrocarbon group which may have a hetero atom, or a cyclic cation forming a ring with the nitrogen atom thereof.

Among the aliphatic amines, secondary aliphatic amines and tertiary aliphatic amines are preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group having 12 or less carbon atoms (alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, dicyclohexylamine, or the like; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, tri-n-dodecylamine, or the like; and alkylalcoholamines such as diethanolamine, triethanolamine, diisopropanolamine, triisopropanolamine, di-n-octanolamine, tri-n-octanolamine, or the like. Among these, trialkylamines of 5 to 10 carbon atoms are preferable, and tri-n-pentylamine and tri-n-octylamine are particularly preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, 1,4-diazabicyclo[2.2.2]octane and the like.

Examples of other aliphatic amines include tris(2-methoxymethoxyethyl)amine, tris {2-(2-methoxyethoxy)ethoxy)ethyl}amine, tris {2-(2-methoxyethoxymethoxy)etohyl}amine, tris {2-(1-methoxyethoxy)ethyl}amine, tris {2-(1-ethoxyethoxy)ethyl}amine, tris {2-(1-ethoxypropoxy)ethyl}amine, tris[2-{2-(2-hydroxyethoxy)ethoxy}ethyl]amine, triethanolamine triacetate and the like, and triethanolamine triacetate is preferable.

Further, as the component (D3), an aromatic amine may be used.

Examples of aromatic amines include 4-dimethylaminopyridine, pyrrole, indole, pyrazole, imidazole and derivatives thereof as well as tribenzylamine, 2,6-diisopropylaniline and N-tert-butoxycarbonylpyrrolidine.

The component (D3) may be used alone or in combination of two or more kinds thereof.

In a case where the resist composition contains the component (D3), the content of the component (D3) in the resist composition is typically in a range of 0.01 to 5 parts by mass with respect to 100 parts by mass of the component (A).

<<Component (E): At Least One Compound Selected from Group Consisting of Organic Carboxylic Acids, Phosphorus Oxo Acids, and Derivatives Thereof>>

For the purpose of preventing any deterioration in sensitivity, and improving the resist pattern shape and the post exposure temporal stability, the resist composition of the present embodiment may contain at least one compound (E) (hereinafter referred to as a "component (E)") selected from the group consisting of an organic carboxylic acid, or a phosphorus oxo acid and a derivative thereof.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid, and phosphinic acid. Among these, phosphonic acid is particularly preferable.

Examples of phosphorus oxo acid derivatives include esters in which a hydrogen atom in the above-described oxo acids is substituted with a hydrocarbon group. Examples of the hydrocarbon group include an alkyl group having 1 to 5 carbon atoms and an aryl group having 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate, and dibenzyl phosphonate.

Examples of phosphinic acid derivatives include phosphinic acid esters and phenylphosphinic acid.

In the resist composition of the present embodiment, the component (E) may be used alone or in combination of two or more kinds thereof.

In a case where the resist composition contains the component (E), the content of the component (E) is typically in a range of 0.01 to 5 parts by mass, with respect to 100 parts by mass of the component (A).

<<Component (F): Fluorine Additive Component>>

The resist composition in the present embodiment may further include a fluorine additive (hereinafter, referred to as a "component (F)") for imparting water repellency to the resist film or for improving lithography characteristics.

As the component (F), a fluorine-containing polymer compound described in Japanese Unexamined Patent Application, First Publication No. 2010-002870, Japanese Unexamined Patent Application, First Publication No. 2010-032994, Japanese Unexamined Patent Application, First Publication No. 2010-277043, Japanese Unexamined Patent Application, First Publication No. 2011-13569, and Japanese Unexamined Patent Application, First Publication No. 2011-128226 can be exemplified.

Specific examples of the component (F) include polymers having a constitutional unit (f1) represented by Formula (f1-1) shown below. As the polymer, a polymer (homopolymer) formed of only a constitutional unit (f1) represented by Formula (f1-1) shown below; a copolymer of the constitutional unit (f1) and the constitutional unit (a4); a copolymer of the constitutional unit (f1) and the constitutional unit (a1); and a copolymer of the constitutional unit (f1), a constitutional unit derived from acrylic acid or methacrylic acid and the above-described constitutional unit (a1) are preferable. As the constitutional unit (a1) to be copolymerized with the constitutional unit (f1), a constitutional unit derived from 1-ethyl-1-cyclooctyl (meth)acrylate and a constitutional unit derived from 1-methyl-1-adamantyl (meth)acrylate are preferable.

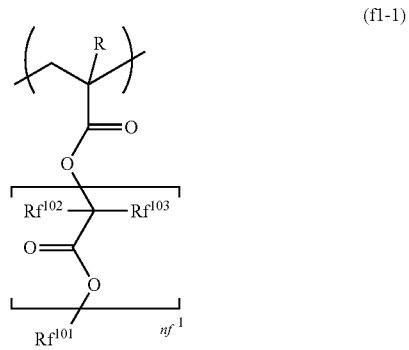

(f1-1)

[In the formula, R has the same definition as described above. $Rf^{102}$ and $Rf^{103}$ each independently represent a hydrogen atom, a halogen atom, an alkyl group having 1 to 5 carbon atoms, or a halogenated alkyl group having 1 to 5 carbon atoms, and $Rf^{102}$ and $Rf^{103}$ may be the same as or different from each other. $nf^1$ represents an integer of 0 to 5, and $Rf^{101}$ represents an organic group containing a fluorine atom.]

In Formula (f1-1), R bonded to the carbon atom at the α-position has the same definition as described above. As R, a hydrogen atom or a methyl group is preferable.

In Formula (f1-1), examples of the halogen atom as $Rf^{102}$ and $Rf^{103}$ include a fluorine atom, a chlorine atom, a bromine atom, and an iodine atom, and a fluorine atom is particularly preferable. Examples of the alkyl group having 1 to 5 carbon atoms as $Rf^{102}$ and $Rf^{103}$ include those described above as the alkyl group having 1 to 5 carbon atoms as R, and a methyl group or an ethyl group is preferable. Specific examples of the halogenated alkyl group having 1 to 5 carbon atoms as $Rf^{102}$ and $Rf^{103}$ include groups in which some or all hydrogen atoms of the above-described alkyl groups of 1 to 5 carbon atoms have been substituted with halogen atoms.

Examples of the halogen atom include a fluorine atom, a chlorine atom, a bromine atom and an iodine atom, and a fluorine atom is particularly preferable. Among these examples, as $Rf^{102}$ and $Rf^{103}$, a hydrogen atom, a fluorine atom, or an alkyl group having 1 to 5 carbon atoms is preferable, and a hydrogen atom, a fluorine atom, a methyl group, or an ethyl group is more preferable.

In Formula (f1-1), $nf^1$ represents an integer of 0 to 5, preferably an integer of 0 to 3, and more preferably an integer of 0 or 1.

In Formula (f1-1), $Rf^{101}$ represents an organic group containing a fluorine atom, and is preferably a hydrocarbon group containing a fluorine atom.

The hydrocarbon group containing a fluorine atom may be linear, branched, or cyclic, and has preferably 1 to 20 carbon atoms, more preferably 1 to 15 carbon atoms, and particularly preferably 1 to 10 carbon atoms.

It is preferable that the hydrocarbon group having a fluorine atom has 25% or more of the hydrogen atoms in the hydrocarbon group fluorinated, more preferably 50% or greater, and particularly preferably 60% or greater from the viewpoint of improving the hydrophobicity of the resist film during immersion exposure.

Among these, as $Rf^{101}$, a fluorinated hydrocarbon group having 1 to 6 carbon atoms is more preferable, and a trifluoromethyl group, —CH$_2$—CF$_3$, —CH$_2$—CF$_2$—CF$_3$, —CH(CF$_3$)$_2$, —CH$_2$—CH$_2$—CF$_3$, and —CH$_2$—CH$_2$—CF$_2$—CF$_2$—CF$_2$—CF$_3$ are particularly preferable.

The weight average molecular weight (Mw) (in terms of polystyrene determined by gel permeation chromatography) of the component (F) is preferably in a range of 1,000 to 50,000, more preferably in a range of 5,000 to 40,000, and most preferably in a range of 10,000 to 30,000. In a case where the weight average molecular weight (Mw) thereof is less than or equal to the upper limit of the above-described range, the resist composition exhibits a sufficient solubility in a solvent for a resist to be used as a resist. Meanwhile, in a case where the weight average molecular weight is greater than or equal to the lower limit of the above-described range, dry etching resistance and the cross-sectional shape of the resist pattern become excellent.

Further, the dispersity (Mw/Mn) of the component (F) is preferably in a range of 1.0 to 5.0, more preferably in a range of 1.0 to 3.0, and most preferably in a range of 1.2 to 2.5.

In the resist composition in the present embodiment, the component (F) may be used alone or in combination of two or more kinds thereof.

In a case where the resist composition contains the component (F), the content of the component (F) is typically in a range of 0.5 to 10 parts by mass, with respect to 100 parts by mass of the component (A).

<<Component (S): Organic Solvent Component>>

The resist composition of the present embodiment may be prepared by dissolving the resist materials in an organic solvent component (hereinafter referred to as "component (S)").

The component (S) may be any component that can dissolve the respective components to be used to obtain a uniform solution, and can be freely and appropriately selected from those which have been conventionally known as solvents for a chemically amplified resist composition and then used.

Examples of the component (S) include lactones such as g-butyrolactone or the like; ketones such as acetone, methyl ethyl ketone, cyclohexanone, ethyl-n-pentyl ketone, methyl isopentyl ketone, and 2-heptanone; polyhydric alcohols such as ethylene glycol, diethylene glycol, propylene glycol, and dipropylene glycol; compounds having an ester bond, such as ethylene glycol monoacetate, diethylene glycol monoacetate, propylene glycol monoacetate, dipropylene glycol monoacetate, or the like; derivatives of polyhydric alcohols such as compounds having an ether bond (e.g. monoalkyl ethers such as monomethyl ether, monoethyl ether, monopropyl ether, monobutyl ether, and monophenyl ether) of the polyhydric alcohols or the compounds having an ester bond [of these, propylene glycol monomethyl ether acetate (PGMEA) and propylene glycol monomethyl ether (PGME) are preferable]; cyclic ethers such as dioxane; esters such as methyl lactate, ethyl lactate (EL), methyl acetate, ethyl acetate, butyl acetate, methyl pyruvate, ethyl pyruvate, methyl methoxypropionate, ethyl ethoxypropionate, or the like; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene, mesitylene, or the like; dimethylsulfoxide (DMSO); and the like.

In the resist composition of the present embodiment, the component (S) may be used alone or as a mixed solvent of two or more kinds thereof.

Of these, PGMEA, PGME, γ-butyrolactone, EL, and cyclohexanone are preferable.

A mixed solvent obtained by mixing PGMEA and a polar solvent is also preferable. The blending ratio (mass ratio) may be appropriately determined in consideration of the compatibility between PGMEA and the polar solvent, but is preferably in the range of 1:9 to 9:1, and more preferably 2:8 to 8:2.

More specifically, in a case where EL or cyclohexanone is blended as the polar solvent, the mass ratio of PGMEA:EL or cyclohexanone is preferably 1:9 to 9:1, and more preferably 2:8 to 8:2. In a case where PGME is blended as the polar solvent, the mass ratio of PGMEA:PGME is preferably 1:9 to 9:1, more preferably 2:8 to 8:2, and still more preferably 3:7 to 7:3. Furthermore, a mixed solvent of PGMEA, PGME, and cyclohexanone is also preferable.

In addition, as the component (S), a mixed solvent of at least one selected from PGMEA and EL and γ-butyrolactone is also preferable. In this case, as a mixing ratio, the mass ratio of the former to the latter is preferably 70:30 to 95:5.

The use amount of the component (S) is not particularly limited, and is appropriately adjusted to a concentration which enables coating of a coating solution to a substrate, depending on the thickness of the coating film. In general, the component (S) is used in an amount such that the solid concentration of the resist composition becomes in the range of 0.1% to 20% by mass and preferably in a range of 0.2% to 15% by mass.

As desired, other miscible additives can also be added to the resist composition of the present embodiment. The resist composition may contain miscible additives such as additive resins, dissolution inhibitors, plasticizers, stabilizers, colorants, halation prevention agents, and dyes for improving the performance of the resist film, as appropriate.

Impurities or the like of the resist composition of the present embodiment may be removed using a polyimide porous membrane, a polyamideimide porous membrane, or the like, after the resist material has been dissolved in the component (S). For example, the resist composition may be filtered using a filter made of a polyimide porous membrane, a filter made of a polyamideimide porous membrane, a filter made of a polyimide porous membrane and a polyamideimide porous membrane, or the like. Examples of the polyimide porous membrane and the polyamideimide porous membrane include those disclosed in Japanese Unexamined Patent Application, First Publication No. 2016-155121.

The resist composition of the present embodiment contains the component (A), the component (BD1), and the optional components as necessary.

In a case where the component (BD1) is used as the component (B1), the suitable resist composition contains the component (A), the component (B1), and the component (D2) or the component (D3). In a case where the component (BD1) is used as the component (D1), the suitable resist composition contains the component (A), the component (B2), and the component (D1).

Further, in a case where the component (BD1) is used as the component (B1) and the component (D1), the suitable resist composition contains the component (A), the component (B1), and the component (D1).

Among these, the resist composition of the present embodiment is preferably the resist composition containing the component (A), the component (B1), and the component (D2) or the component (D3), more preferably a resist composition containing the component (A), the component (B1), and the component (D1), and still more preferably a resist composition containing the component (A), the component (B1), and the component (D1).

The resist composition of the present embodiment described above contains the compound (BD1) represented by Formula (bd1). The component (BD1) has a plurality of fluorine atoms on the carbon atom adjacent to the carbon atom that is bonded to the sulfur atom of the cation moiety. Thereby, the cation moiety of the component (BD1) is allowed to exhibit high decomposition efficiency upon exposure, and thus in a case where using the component (BD1) as the component (B), an acid can be efficiently generated in the exposed portion of a resist film. In addition, in a case where the component (BD1) is used as the component (D), the component (BD1) acts as a quencher in the unexposed portion of the resist film, but sufficiently loses its acid diffusion controllability (basicity) in the exposed portion of the resist film because of the high decomposition efficiency, thereby further improving the contrast between the unexposed portion and the exposed portion.

Therefore, by containing such a component (BD1) including the anion moiety and the cation moiety, according to the resist composition of the embodiment, it is considered that sensitivity is enhanced and lithography characteristics (roughness reduction, etc.) are further improved.

By using the resist composition of the embodiment, uniformity of the compound (BD1) is enhanced in the formed resist film, whereby it is possible to easily form a high-resolution, well-shaped resist pattern with reduced roughness.

(Method of Forming a Resist Pattern)

A method of forming a resist pattern according to the second aspect of the present invention includes a step of forming a resist film on a support using the resist composition of the embodiment; a step of exposing the resist film; and a step of developing the exposed resist film to form a resist pattern.

According to the embodiment of method of forming a resist pattern, a method of forming a resist pattern by performing processes as described below is exemplified.

First, a resist composition according to the embodiment is applied to a support using a spinner or the like, and a bake treatment (post applied bake (PAB)) is conducted under temperature conditions of 80° C. to 150° C. for 40 to 120 seconds and preferably 60 to 90 seconds, to form a resist film.

Following selective exposure of the thus formed resist film, by exposure through a mask having a predetermined pattern formed thereon (mask pattern) using an exposure apparatus such as an electron beam lithography apparatus or an EUV exposure apparatus, or by patterning via direct irradiation with an electron beam without using a mask pattern, baking treatment (post exposure baking (PEB)) is conducted under temperature conditions of 80° C. to 150° C. for 40 to 120 seconds, and preferably 60 to 90 seconds.

Next, the resist film is subjected to a developing treatment. The developing treatment is conducted using an alkali developing solution in a case of an alkali developing process, and a developing solution containing an organic solvent (organic developing solution) in a case of a solvent developing process.

After the developing treatment, it is preferable to conduct a rinse treatment. In the case of an alkali developing process, water rinse using pure water is preferable, and in the case of a solvent developing process, use of a rinse liquid containing an organic solvent is preferable.

In a case of a solvent developing process, after the developing treatment or the rinse treatment, the developing solution or the rinse liquid remaining on the pattern can be removed by a treatment using a supercritical fluid.

After the developing treatment or the rinse treatment, drying is conducted. As desired, bake treatment (post bake) can be conducted following the developing treatment.

In this manner, a resist pattern can be formed.

The support is not specifically limited and a conventionally known support can be used. For example, substrates for electronic components, and such substrates having predetermined wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the support, any one of the above-described substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

The wavelength to be used for exposure is not particularly limited and the exposure can be conducted using radiation such as an ArF excimer laser, a KrF excimer laser, an F2 excimer laser, extreme ultraviolet radiation (EUV), vacuum ultraviolet radiation (VUV), electron beam (EB), X-rays, and soft X-rays. The resist composition of the present invention is useful for a KrF excimer laser, an ArF excimer laser, EB, and EUV, more useful for an ArF excimer laser, EB, and EUV, and particularly useful for EB and EUV. That is, the method of forming a resist pattern according to the present embodiment is a particularly useful method when the step of exposing the resist film includes exposing the resist film to extreme ultraviolet radiation (EUV) or electron beam (EB).

The exposure of the resist film can be a general exposure (dry exposure) conducted in air or an inert gas such as nitrogen, or immersion exposure (liquid immersion lithography).

In liquid immersion lithography, the region between the resist film and the lens at the lowermost point of the exposure apparatus is pre-filled with a solvent (liquid immersion medium) that has a larger refractive index than the refractive index of air, and the exposure (immersion exposure) is conducted in this state.

The liquid immersion medium preferably exhibits a refractive index larger than the refractive index of air but smaller than the refractive index of the resist film to be exposed. The refractive index of the solvent is not particularly limited as long as it satisfies the above-described requirements.

Examples of this solvent which exhibits a refractive index that is larger than the refractive index of air but smaller than the refractive index of the resist film include water, fluorine-based inert liquids, silicon-based solvents, and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, and the boiling point is preferably in a range of 70° C. to 180° C. and more preferably in a range of 80° C. to 160° C. A fluorine-based inert liquid having a boiling point in the above-described range is preferable because the removal of the immersion medium after the exposure can be conducted by a simple method.

As a fluorine-based inert liquid, a perfluoroalkyl compound in which all of the hydrogen atoms of the alkyl group are substituted with fluorine atoms is particularly preferable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point of 102° C.), and an example of a suitable perfluoroalkylamine compound is perfluorotributylamine (boiling point of 174° C.).

As the immersion medium, water is preferable in terms of cost, safety, environment, and versatility.

As an example of the alkali developing solution used in an alkali developing process, a 0.1 to 10 mass % aqueous solution of tetramethylammonium hydroxide (TMAH) can be exemplified.

As the organic solvent contained in the organic developing solution used in a solvent developing process, any of the conventional organic solvents can be used which are capable of dissolving the component (A) (prior to exposure). Specific examples of the organic solvent include polar solvents such as ketone solvents, ester solvents, alcohol solvents, nitrile solvents, amide solvents, ether solvents, and hydrocarbon solvents.

A ketone solvent is an organic solvent containing C—C(=O)—C in the structure thereof. An ester solvent is an organic solvent containing C—C(=O)—O—C in the structure thereof. An alcohol solvent is an organic solvent containing an alcoholic hydroxyl group in the structure thereof. An "alcoholic hydroxyl group" indicates a hydroxyl group bonded to a carbon atom of an aliphatic hydrocarbon group. A nitrile solvent is an organic solvent containing a nitrile group in the structure thereof. An amide solvent is an organic solvent containing an amide group in the structure thereof. An ether solvent is an organic solvent containing C—O—C in the structure thereof.

Some organic solvents have a plurality of the functional groups which characterizes the above-described solvents in the structure thereof. In such a case, the organic solvent can be classified as any type of the solvent having the characteristic functional group. For example, diethylene glycol monomethylether can be classified as an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

As the organic solvent contained in the organic developing solution, among these, a polar solvent is preferable, and ketone solvents, ester solvents, nitrile solvents and the like are preferable.

Examples of ketone solvents include 1-octanone, 2-octanone, 1-nonanone, 2-nonanone, acetone, 4-heptanone, 1-hexanone, 2-hexanone, diisobutyl ketone, cyclohexanone, methylcyclohexanone, phenylacetone, methyl ethyl ketone, methyl isobutyl ketone, acetylacetone, acetonylacetone, ionone, diacetonylalcohol, acetylcarbinol, acetophenone, methyl naphthyl ketone, isophorone, propylenecarbonate, g-butyrolactone, methyl amyl ketone (2-heptanone), and the like. Among these examples, as a ketone solvent, methyl amyl ketone (2-heptanone) is preferable.

Examples of ester solvents include methyl acetate, butyl acetate, ethyl acetate, isopropyl acetate, amyl acetate, isoamyl acetate, ethyl methoxyacetate, ethyl ethoxyacetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate, propyl-3-methoxypropionate, and the like. Among these examples, as an ester solvent, butyl acetate is preferable.

Examples of nitrile solvents include acetonitrile, propionitrile, valeronitrile, butyronitrile and the like.

As necessary, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a non-ionic fluorine surfactant or a non-ionic silicon surfactant is more preferable.

In a case where a surfactant is added, the amount thereof based on the total amount of the organic developing solution is generally 0.001% to 5% by mass, preferably 0.005% to 2% by mass, and more preferably 0.01% to 0.5% by mass.

The developing treatment can be performed by a conventional developing method. Examples thereof include a method in which the support is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in a case of a solvent developing process, any of the above-described organic solvents contained in the organic developing solution can be used which poorly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly preferable.

The alcohol solvent used for the rinse liquid is preferably a monohydric alcohol of 6 to 8 carbon atoms, and the monohydric alcohol may be linear, branched or cyclic. Specific examples thereof include 1-hexanol, 1-heptanol, 1-octanol, 2-hexanol, 2-heptanol, 2-octanol, 3-hexanol, 3-heptanol, 3-octanol, 4-octanol, benzyl alcohol, and the like. Among these, 1-hexanol, 2-heptanol and 2-hexanol are preferable, and 1-hexanol and 2-hexanol are more preferable.

As the organic solvent, one kind of solvent may be used alone, or two or more kinds of solvents may be used in combination. Further, an organic solvent other than the above-described examples or water may be mixed together. However, in consideration of the development characteristics, the amount of water in the rinse liquid, based on the total amount of the rinse liquid is preferably 30% by mass or less, more preferably 10% by mass or less, still more preferably 5% by mass or less, and most preferably 3% by mass or less.

As necessary, the rinse liquid may have a conventional additive blended. Examples of the additive include surfactants. As the surfactant, the same surfactants as those described above can be exemplified, a non-ionic surfactant is preferable, and a non-ionic fluorine surfactant or a non-ionic silicon surfactant is more preferable.

In a case where a surfactant is added, the amount thereof based on the total amount of the rinse liquid is generally 0.001% to 5% by mass, preferably 0.005% to 2% by mass, and more preferably 0.01% to 0.5% by mass.

The rinse treatment using a rinse liquid (washing treatment) can be conducted by a conventional rinse method. Examples of the rinse method include a method in which the rinse liquid is continuously applied to the support while rotating it at a constant rate (rotational coating method), a method in which the support is immersed in the rinse liquid for a predetermined time (dip method), and a method in which the rinse liquid is sprayed onto the surface of the support (spray method).

In the method of forming a resist pattern of the present embodiment described above, the resist composition according to the first aspect described above is used, thus it is possible to form a resist pattern having higher sensitivity and better lithography characteristics (roughness reduction and the like) at the time of forming a resist pattern.

(Compound)

A compound according to a third aspect of the present invention is a compound including an anion moiety and a cation moiety and represented by Formula (bd1).

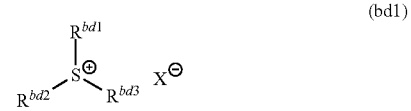

(bd1)

[In the formula, $R^{bd1}$ to $R^{bd3}$ each independently represent an aryl group which may have a substituent. Here, at least two of $R^{bd1}$ to $R^{bd3}$ are aryl groups having one or more fluorine atoms as substituents, and at least one of the fluorine atoms of the aryl group is bonded to a carbon atom adjacent to a carbon atom that is bonded to a sulfur atom in the formula. In $R^{bd1}$ to $R^{bd3}$, the total number of the fluorine atoms bonded as substituents to the carbon atom adjacent to the carbon atom that is bonded to the sulfur atom in the formula is 4 or more. Two of $R^{bd1}$ to $R^{bd3}$ may be bonded to each other to form a fused ring together with the sulfur atom in the formula. $X^-$ represents a counter anion.]

The compound described above is preferably a compound including an anion moiety and a cation moiety and represented by Formula (bd1-1).

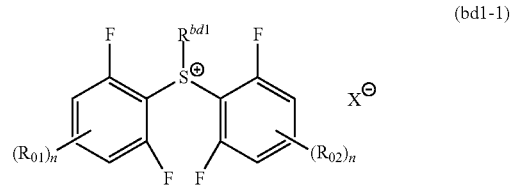

(bd1-1)

[In the formula, $R^{bd1}$ represents an aryl group which may have a substituent. $R_{O1}$ and $R_{O2}$ each independently represent a substituent; each n independently represents an integer of 0 to 3. $X^-$ represents a counter anion.]

The compounds represented by Formulae (bd1) and (bd1-1) are the same compounds as the component (BD1) in the above description of the resist composition.

[Preparation Method of Compound (BD1)]

The compound (BD1) can be prepared according to a known method.

For example, the compound (BD1) can be prepared by the following production method.

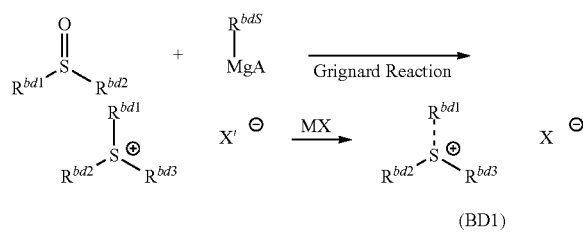

In the above reaction scheme, A represents a halogen atom, $X^{l-}$ represents $Cl^-$ or a trifluoromethanesulfonate anion, and MX represents a salt of alkali metal (lithium, sodium, potassium, or the like) cation or ammonium cation (that may have a substituent) and a counter anion (for example, anion represented by Formula (b1-1-an1)). $R^{bd1}$ to $R^{bd3}$ and $X^-$ are the same as defined in Formula (bd1).

$X^{l-}$ can be exchanged for the anion ($X^-$) of the compound (BD1) by, for example, a metathesis reaction as shown above.

In the above reaction scheme, the first stage reaction may be carried out in the absence of a solvent or, as necessary, in an organic solvent (general solvents used in Grignard reactions such as tetrahydrofuran, chloroform, and dichloromethane). The reaction temperature is about −20 to 150° C. depending on the boiling point of the solvent used. The reaction time is about 1 hour or more and tens of hours or less.

The reaction in the second stage may be performed subsequent to the reaction in the first stage, or may be performed after the precursor is isolated (purified as necessary). The compound (BD1) can be obtained as a solid or a viscous liquid by mixing and stirring the precursor and an aqueous solution of salt (MX) to carry out a metathesis reaction, and filtering off the precipitated solid, or extracting separated oil-like substance with an organic solvent to remove the organic solvent. The obtained solid or viscous liquid can be washed with a suitable organic solvent as necessary, or purified by recrystallization or column chromatography.

The chemical structure of the compound (BD1) can be identified by a general analytical method (for example, $^1$H-, $^{11}$B-, $^{13}$C-, $^{19}$F-, $^{31}$P-nuclear magnetic resonance spectrum, infrared absorption spectrum and/or elemental analysis).

EXAMPLES

Hereinafter, the present invention will be described in more detail with reference to Examples, but the present invention is not limited to these examples.

<Preparation of Compound>

Preparation Example 1

Magnesium (6.9 g) and tetrahydrofuran (225 g) were stirred at room temperature, and dibromoethane (4.8 g) was added. A solution of 1-bromo-2,6-difluorobenzene (51 g) dissolved in tetrahydrofuran (130 g) was added dropwise to the resultant while cooling with ice. After completion of the dropwise addition, the solution was stirred for 4 hours to obtain a solution 1. Into a separate container, thionyl chloride (20 g) and tetrahydrofuran (870 g) were added and stirred while cooling with ice. While the solution 1 was added dropwise thereto, the solution was stirred for 1 hour to obtain a solution 2. Into another separate container, thionyl chloride (26 g) and tetrahydrofuran (1,100 g) were added and stirred while cooling with ice. While the solution 2 was added dropwise thereto, the solution was stirred for 1 hour to obtain a solution 3. The solution 3 was poured into ultrapure water (1,100 g) over 1 hour, and then dichloromethane (440 g) was added thereto. After stirring for 30 minutes, the aqueous layer was removed. The obtained organic layer was washed with ultrapure water (110 g) 3 times, and the organic layer was concentrated under reduced pressure. The concentrated residue was crystallized with tert-butyl methyl ether/cyclohexane to obtain an intermediate 1 (25 g) in the form of a white solid.

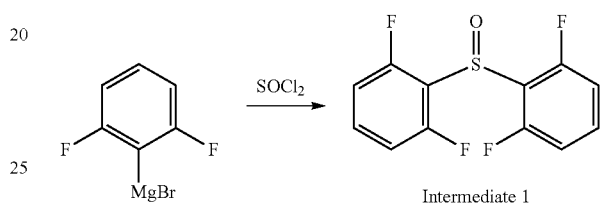

The intermediate 1 (15 g) and benzene (130 g) were stirred at 10° C. Trifluoromethanesulfonic anhydride (15 g) was added dropwise thereto and stirred for 1 hour. The resultant was allowed to stand, and the supernatant was removed, followed by removing the benzene layer. The obtained residue was dissolved in dichloromethane (100 g), washed 3 times with ultrapure water (60 g), and then the organic layer was concentrated under reduced pressure. The concentrated residue was crystallized with dichloromethane/diisopropyl ether to obtain a compound C-1 (17 g).

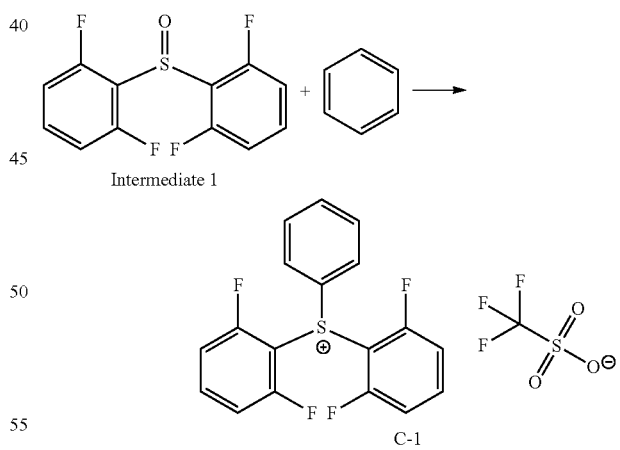

Preparation Example 2

Magnesium (4.2 g) and tetrahydrofuran (19 g) were stirred at 50° C., and a solution of 2,6-difluorobromobenzene (38 g) dissolved in tetrahydrofuran (75 g) was added dropwise at the same temperature. After completion of the dropwise addition, the mixture was stirred for 2 hours, cooled to room temperature, and then tetrahydrofuran (75 g) was added to obtain a solution 4. Into a separate container, an intermediate 1 (10 g) and tetrahydrofuran (75 g) were added and stirred at room temperature. Trimethylsilyl trifluoromethanesulfonate (63 g) and the solution 4 were added dropwise to the resultant. After completion of the dropwise addition, the reaction was continued at room temperature for 1 hour to complete the reaction. Thereafter, dichloromethane (100 g) was added, and after stirring for 30 minutes, the aqueous layer was removed. The organic layer was washed with ultrapure water (100 g) 3 times, and the organic layer was concentrated under reduced pressure. The concentrated residue was crystallized with dichloromethane/tert-butyl methyl ether to obtain a compound C-2 (6.2 g) in the form of a white solid.

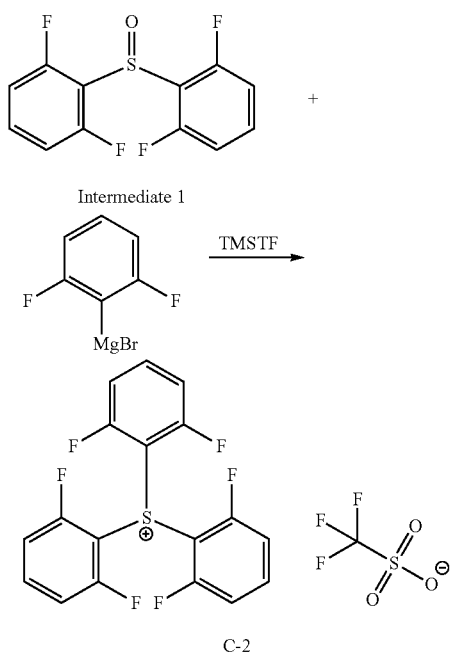

Preparation Example 3

A compound C-3 (19 g) was obtained in the same manner as in Preparation Example 1, except that benzene (130 g) was changed to toluene (153 g).

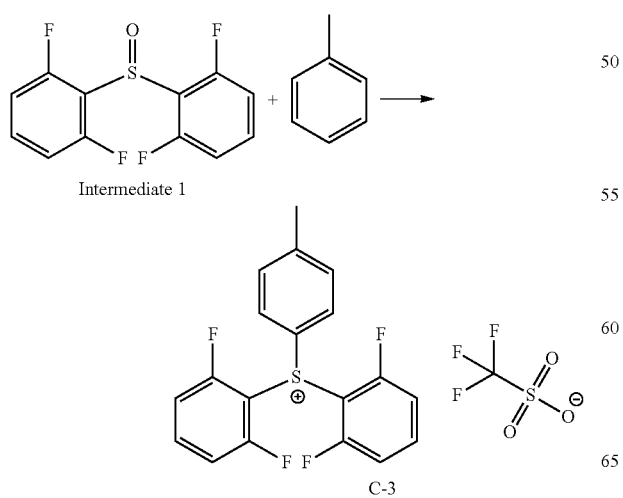

Preparation Example 4

A precursor 1 (20 g) was obtained in the same manner as in Preparation Example 1, except that benzene (130 g) was changed to methyl phenyl sulfide (207 g).

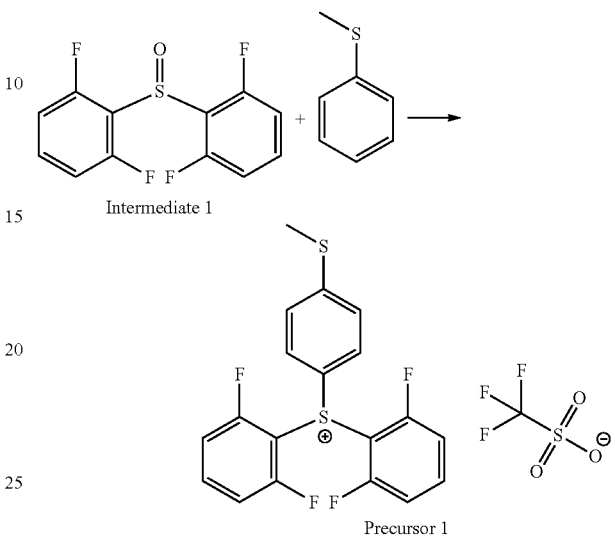

The precursor 1 (19 g) was dissolved in a mixed solution of ultrapure water (14 g) and methanol (43 g), and Oxone (registered trademark) (33 g) was added to the mixture, and the mixture was stirred at room temperature for 48 hours. The reaction solution was filtered, ultrapure water (48 g) and dichloromethane (180 g) were added and stirred for 30 minutes, and then the aqueous layer was removed.

After washing the resultant with a saturated sodium hydrogen sulfite aqueous solution (60 g) and then washing with ultrapure water (60 g) 3 times, the organic layer was crystallized with tert-butyl methyl ether (1800 g) to obtain Compound C-4 (14 g).

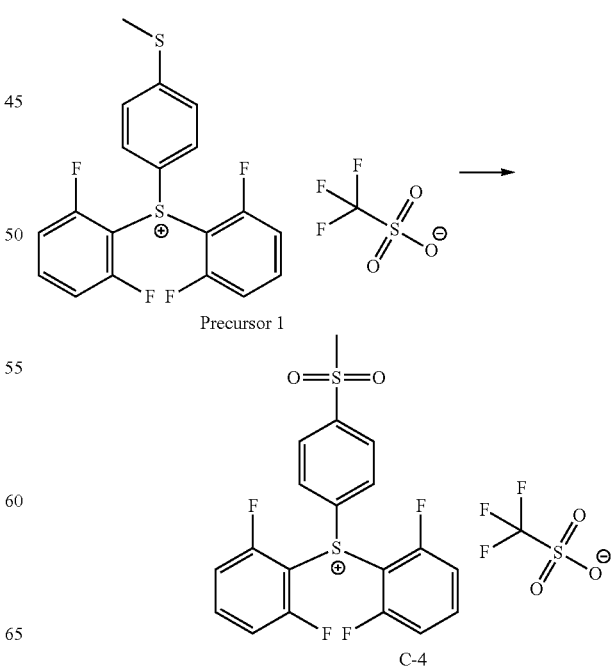

Preparation Example of Compound (B1-1)

The compound C-1 (10 g) and the compound A-1 (6.0 g) were dissolved in dichloromethane (80 g), and ultrapure water (25 g) was added to the mixture, followed by stirring the mixture at room temperature for 30 minutes. After removing the aqueous layer, the organic layer was washed 4 times with ultrapure water (25 g). The organic layer was concentrated under reduced pressure to obtain a compound (B1-1) (12 g) in the form of a white solid.

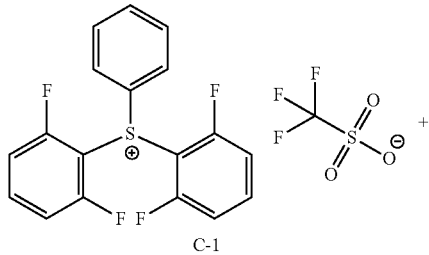

C-1

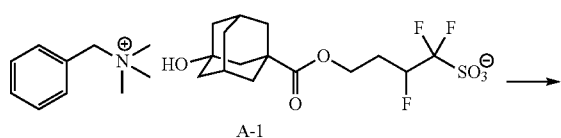

A-1

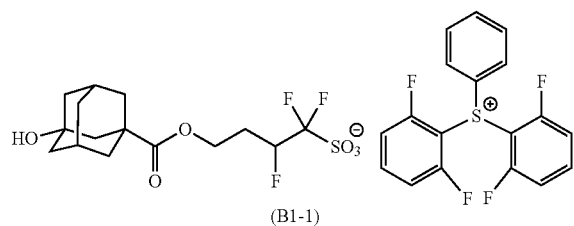

(B1-1)

Preparation Examples of Compounds (B1-2) to (B1-10)

Compounds (B1-2) to (B1-10) respectively represented by Chemical Formulae (B1-2) to (B1-10), were obtained in the same manner as in "Preparation Example of Compound (B1-1)" except that the combinations of the above compounds C-1 to C-4 and compounds A-1 to A-4 were changed.

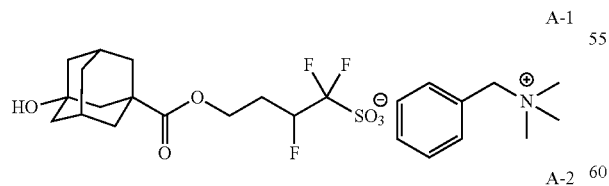

A-1

A-2

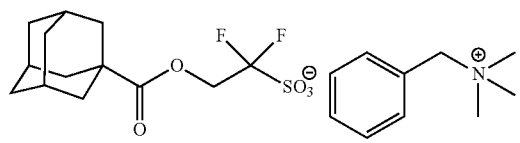

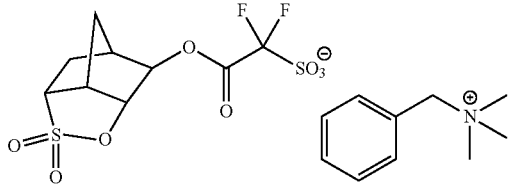

A-3

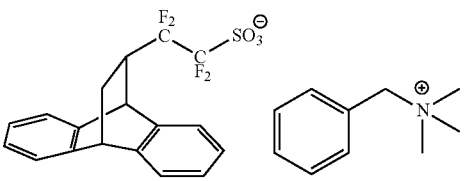

A-4

Preparation Example of Compound (D1-1)

The compound C-1 (10 g) was dissolved in dichloromethane (200 g). Then, ultrapure water (100 g) and sodium salicylate (12 g) were added thereto and stirred for 30 minutes. Thereafter, the organic layer was washed with ultrapure water (100 g) 3 times, and the organic layer was concentrated under reduced pressure. The concentrated residue was crystallized with dichloromethane/tert-butyl methyl ether to obtain a compound (D1-1) (13 g) as a white solid.

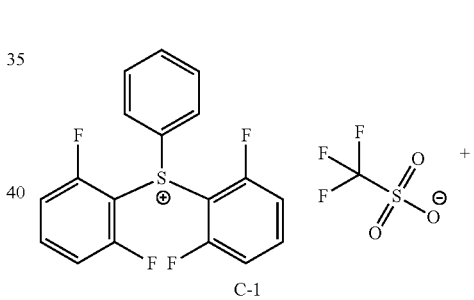

C-1

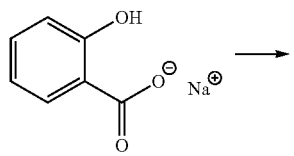

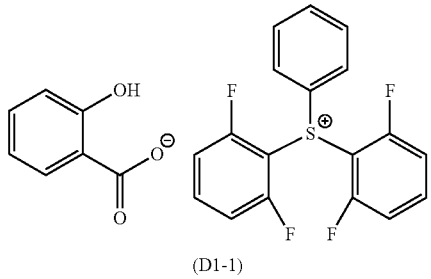

(D1-1)

Each of the obtained compounds was subjected to NMR measurement, and the structure was identified from the following analysis results.

(B1-1)
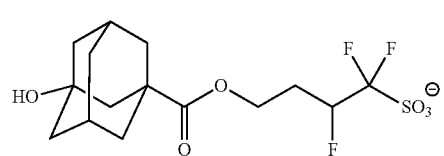
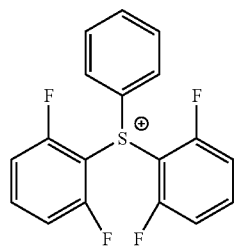
(B1-2)
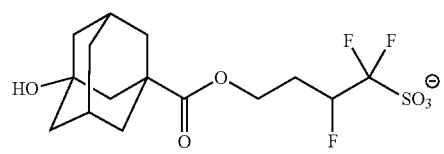
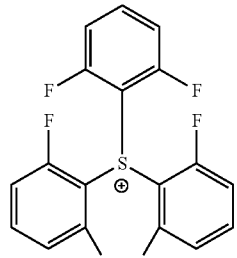
(B1-3)
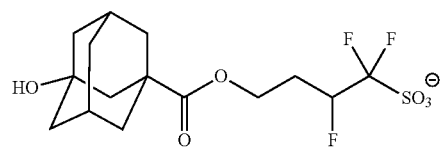
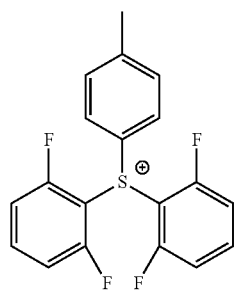
(B1-4)
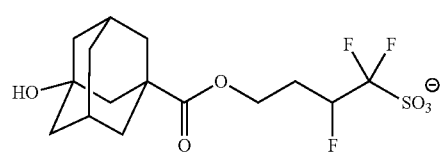
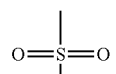
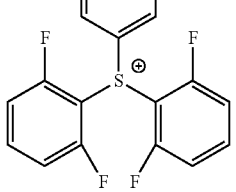
(B1-5)
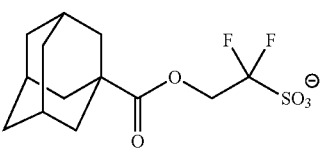
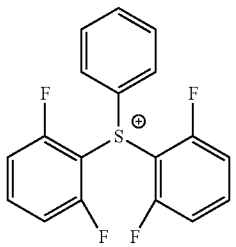
(B1-6)
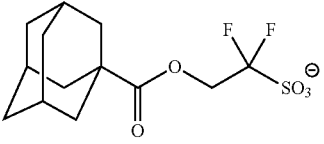
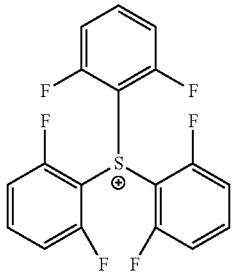
(B1-7)
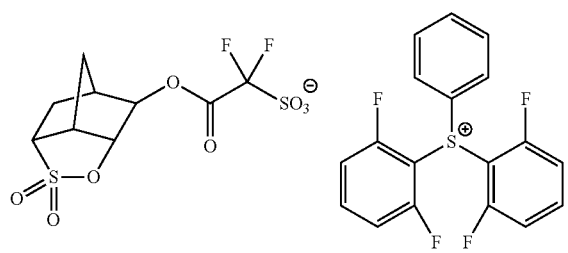

Compound (B1-1): Combination of Compound C-1 and Compound A-1

¹H-NMR (DMSO, 400 MHz): δ (ppm)=8.20-8.03 (m, 4H), 7.95-7.85 (m, 1H), 7.85-7.75 (m, 2H), 7.72-7.56 (m, 4H), 5.08-4.87 (m, 1H), 4.55 (s, 1H), 4.23-4.05 (m, 2H), 2.47-2.30 (m, 1H), 2.14-2.05 (m, 2H), 2.04-1.91 (m, 1H), 1.70-1.63 (m, 6H), 1.55-1.48 (m, 6H)

¹⁹F-NMR (DMSO, 376 MHz): δ (ppm)=−103.1, −112.9, −121.9, −203.0

Compound (B1-2): Combination of Compound C-2 and Compound A-1

¹H-NMR (DMSO, 400 MHz): δ (ppm)=8.20-8.05 (m, 3H), 7.75-7.58 (m, 6H), 5.08-4.87 (m, 1H), 4.55 (s, 1H), 4.23-4.05 (m, 2H), 2.47-2.30 (m, 1H), 2.14-2.05 (m, 2H), 2.04-1.91 (m, 1H), 1.70-1.63 (m, 6H), 1.55-1.48 (m, 6H)

¹⁹F-NMR (DMSO, 376 MHz): δ (ppm)=: −102.9, −112.9, −121.9, −203.0

Compound (B1-3): Combination of Compound C-3 and Compound A-1

¹H-NMR (DMSO, 400 MHz): δ (ppm)=8.20-8.05 (m, 2H), 7.81-7.56 (m, 8H), 5.08-4.87 (m, 1H), 4.55 (s, 1H), 4.23-4.05 (m, 2H), 2.47-2.30 (m, 4H), 2.14-2.05 (m, 2H), 2.04-1.91 (m, 1H), 1.70-1.63 (m, 6H), 1.55-1.48 (m, 6H)

¹⁹F-NMR (DMSO, 376 MHz): δ (ppm)=−103.2, −112.9, −121.9, −203.0

Compound (B1-4): Combination of Compound C-4 and Compound A-1

¹H-NMR (DMSO, 400 MHz): δ (ppm)=8.31-7.98 (m, 6H), 7.72-7.56 (m, 4H), 5.08-4.87 (m, 1H), 4.55 (s, 1H), 4.23-4.05 (m, 2H), 3.55 (s, 3H), 2.47-2.30 (m, 1H), 2.14-2.05 (m, 2H), 2.04-1.91 (m, 1H), 1.70-1.63 (m, 6H), 1.55-1.48 (m, 6H)

¹⁹F-NMR (DMSO, 376 MHz): δ (ppm)=−102.8, −112.9, −121.9, −203.0

Compound (B1-5): Combination of Compound C-1 and Compound A-2

¹H-NMR (DMSO, 400 MHz): δ (ppm)=8.20-8.03 (m, 4H), 7.95-7.85 (m, 1H), 7.85-7.75 (m, 2H), 7.72-7.56 (m, 4H), 4.55 (t, 2H), 1.96-1.64 (m, 15H)

¹⁹F-NMR (DMSO, 376 MHz): δ (ppm)=−103.1, −111.2

Compound (B1-6): Combination of Compound C-2 and Compound A-2

¹H-NMR (DMSO, 400 MHz): δ (ppm)=8.20-8.05 (m, 3H), 7.75-7.58 (m, 6H), 4.55 (t, 2H), 1.96-1.64 (m, 15H)

¹⁹F-NMR (DMSO, 376 MHz): δ (ppm)=−102.9, −111.2

Compound (B1-7): Combination of Compound C-1 and Compound A-3

¹H-NMR (DMSO, 400 MHz): δ (ppm)=8.20-8.03 (m, 4H), 7.95-7.85 (m, 1H), 7.85-7.75 (m, 2H), 7.72-7.56 (m, 4H), 4.79-4.77 (m, 1H), 4.66 (dd, 1H), 3.88 (dd, 1H), 3.36-3.31 (m, 1H), 2.49-2.47 (m, 1H), 2.21-1.73 (m, 4H)

¹⁹F-NMR (DMSO, 376 MHz): δ (ppm)=−103.1, −107.7

Compound (B1-8): Combination of Compound C-2 and Compound A-3

¹H-NMR (DMSO, 400 MHz): δ (ppm)=8.20-8.05 (m, 3H), 7.75-7.58 (m, 6H), 4.79-4.77 (m, 1H), 4.66 (dd, 1H), 3.88 (dd, 1H), 3.36-3.31 (m, 1H), 2.49-2.47 (m, 1H), 2.21-1.73 (m, 4H)

¹⁹F-NMR (DMSO, 376 MHz): δ (ppm)=−102.9, −107.7

Compound (B1-9): Combination of Compound C-1 and Compound A-4

¹H-NMR (DMSO, 400 MHz): δ (ppm)=8.20-8.03 (m, 4H), 7.95-7.85 (m, 1H), 7.85-7.75 (m, 2H), 7.72-7.56 (m, 4H), 7.01-7.47 (m, 8H), 4.72 (s, 1H), 4.43 (s, 1H), 2.95-3.02 (m, 1H), 2.04-1.95 (m, 2H)

¹⁹F-NMR (DMSO, 376 MHz): δ (ppm)=−103.1, −111.3, −117.4

Compound (B1-10): Combination of Compound C-2 and Compound A-4

¹H-NMR (DMSO, 400 MHz): δ (ppm)=8.20-8.05 (m, 3H), 7.75-7.58 (m, 6H), 7.01-7.47 (m, 8H), 4.72 (s, 1H), 4.43 (s, 1H), 2.95-3.02 (m, 1H), 2.04-1.95 (m, 2H)

¹⁹F-NMR (DMSO, 376 MHz): δ (ppm)=−102.9, −111.3, −117.4

Compound (D1-1): Combination of Compound C-1 and Sodium Salicylate

¹H-NMR (DMSO, 400 MHz): δ (ppm)=8.20-8.03 (m, 4H), 7.95-7.85 (m, 1H), 7.85-7.75 (m, 2H), 7.72-7.56 (m, 4H), 7.53-7.51 (m, 1H), 7.11-7.06 (m, 1H), 6.62-6.50 (m, 2H)

¹⁹F-NMR (DMSO, 376 MHz): δ (ppm)=−103.1

<Preparation of Resist Composition>

Examples 1 to 16 and Comparative Examples 1 to 15

The components shown in Tables 1 to 5 were mixed and dissolved to prepare resist compositions (solid content concentration: 1.7% by mass) of the respective examples.

TABLE 1

|  | Component (A) | Component (B) | | Component (D) | | Component (S) |
|---|---|---|---|---|---|---|
|  |  | Component (B1) | Component (B2) | Component (D1) | Component (D2) |  |
| Example 1 | (A)-1 [100] | (B1)-1 [20.4] | — | — | (D2)-1 [3.8] | (S)-1 [7200] |
| Example 2 | (A)-1 [100] | (B1)-2 [21.5] | — | — | (D2)-1 [3.8] | (S)-1 [7200] |
| Example 3 | (A)-1 [100] | (B1)-3 [20.9] | — | — | (D2)-1 [3.8] | (S)-1 [7200] |
| Example 4 | (A)-1 [100] | (B1)-4 [22.7] | — | — | (D2)-1 [3.8] | (S)-1 [7200] |
| Example 5 | (A)-1 [100] | (B1)-1 [20.4] | — | (D1)-1 [4.4] | — | (S)-1 [7200] |
| Comparative Example 1 | (A)-1 [100] | — | (B2)-1 [18.5] | — | (D2)-1 [3.8] | (S)-1 [7200] |
| Comparative Example 2 | (A)-1 [100] | — | (B2)-2 [19.7] | — | (D2)-1 [3.8] | (S)-1 [7200] |
| Comparative Example 3 | (A)-1 [100] | — | (B2)-3 [19.5] | — | (D2)-1 [3.8] | (S)-1 [7200] |
| Comparative Example 4 | (A)-1 [100] | — | (B2)-4 [20.4] | — | (D2)-1 [3.8] | (S)-1 [7200] |

TABLE 2

|  | Component (A) | Component (B) | | Component (D) | | Component (S) |
|---|---|---|---|---|---|---|
|  |  | Component (B1) | Component (B2) | Component (D1) | Component (D2) |  |
| Example 6 | (A)-2 [100] | (B1)-5 [18.6] | — | — | (D2)-1 [3.8] | (S)-1 [7200] |
| Example 7 | (A)-2 [100] | (B1)-6 [19.8] | — | — | (D2)-1 [3.8] | (S)-1 [7200] |
| Comparative Example 5 | (A)-2 [100] | — | (B2)-5 [16.7] | — | (D2)-1 [3.8] | (S)-1 [7200] |
| Comparative Example 6 | (A)-2 [100] | — | (B2)-6 [17.9] | — | (D2)-1 [3.8] | (S)-1 [7200] |
| Comparative Example 7 | (A)-2 [100] | — | (B2)-7 [17.7] | — | (D2)-1 [3.8] | (S)-1 [7200] |

TABLE 3

|  | Component (A) | Component (B) | | Component (D) | | Component (S) |
|---|---|---|---|---|---|---|
|  |  | Component (B1) | Component (B2) | Component (D1) | Component (D2) |  |
| Example 8 | (A)-3 [100] | (B1)-7 [19.3] | — | — | (D2)-1 [3.8] | (S)-1 [7200] |
| Example 9 | (A)-3 [100] | (B1)-8 [20.5] | — | — | (D2)-1 [3.8] | (S)-1 [7200] |
| Comparative Example 8 | (A)-3 [100] | — | (B2)-8 [17.4] | — | (D2)-1 [3.8] | (S)-1 [7200] |
| Comparative Example 9 | (A)-3 [100] | — | (B2)-9 [19.3] | — | (D2)-1 [3.8] | (S)-1 [7200] |

TABLE 4

|  | Component (A) | Component (B) | | Component (D) | | Component (S) |
|---|---|---|---|---|---|---|
|  |  | Component (B1) | Component (B2) | Component (D1) | Component (D2) |  |
| Example 10 | (A)-4 [100] | (B1)-1 [20.4] | — | — | (D2)-1 [3.8] | (S)-1 [7200] |
| Example 11 | (A)-4 [100] | (B1)-2 [21.5] | — | — | (D2)-1 [3.8] | (S)-1 [7200] |
| Example 12 | (A)-4 [100] | (B1)-3 [20.9] | — | — | (D2)-1 [3.8] | (S)-1 [7200] |
| Example 13 | (A)-4 [100] | (B1)-4 [22.7] | — | — | (D2)-1 [3.8] | (S)-1 [7200] |
| Example 14 | (A)-4 [100] | (B1)-1 [20.4] | — | (D1)-1 [4.4] | — | (S)-1 [7200] |
| Comparative Example 10 | (A)-4 [100] | — | (B2)-1 [18.5] | — | (D2)-1 [3.8] | (S)-1 [7200] |
| Comparative Example 11 | (A)-4 [100] | — | (B2)-2 [19.7] | — | (D2)-1 [3.8] | (S)-1 [7200] |
| Comparative Example 12 | (A)-4 [100] | — | (B2)-3 [19.5] | — | (D2)-1 [3.8] | (S)-1 [7200] |
| Comparative Example 13 | (A)-4 [100] | — | (B2)-4 [20.4] | — | (D2)-1 [3.8] | (S)-1 [7200] |

TABLE 5

| | Component (A) | Component (B) | | Component (D) | | Component (S) |
| | | Component (B1) | Component (B2) | Component (D1) | Component (D2) | |
|---|---|---|---|---|---|---|
| Example 15 | (A)-5 [100] | (B1)-9 [19.3] | — | — | (D2)-1 [3.8] | (S)-1 [7200] |
| Example 16 | (A)-5 [100] | (B1)-10 [20.5] | — | — | (D2)-1 [3.8] | (S)-1 [7200] |
| Comparative Example 14 | (A)-5 [100] | — | (B2)-10 [17.4] | — | (D2)-1 [3.8] | (S)-1 [7200] |
| Comparative Example 15 | (A)-5 [100] | — | (B2)-11 [18.4] | — | (D2)-1 [3.8] | (S)-1 [7200] |

The abbreviations in Tables 1 to 5 have the following meanings. The numerical values in the parentheses are blending amounts (parts by mass).

(A)-1: polymer compound represented by Chemical Formula (A-1). The polymer compound (A-1) was obtained by radical polymerization using monomers from which the constitutional units constituting the polymer compound are derived at a predetermined molar ratio. The weight average molecular weight (Mw) of the polymer compound (A-1) in terms of standard polystyrene equivalent determined by GPC measurement was 6,900, and the molecular weight dispersion degree (Mw/Mn) was 1.72. The copolymerization compositional ratio (the proportion (molar ratio) of each constitutional unit in the structural formula) (l/m/n) acquired by $^{13}$C-NMR was 30/60/10.

(A)-2: polymer compound represented by Chemical Formula (A-2). The weight average molecular weight (Mw) of the polymer compound (A-2) in terms of standard polystyrene equivalent determined by GPC measurement was 6,400, and the molecular weight dispersion degree (Mw/Mn) was 1.66. The copolymerization compositional ratio (the proportion (molar ratio) of each constitutional unit in the structural formula) (l/m) acquired by $^{13}$C-NMR was 40/60.

(A)-3: polymer compound represented by Chemical Formula (A-3). The weight average molecular weight (Mw) of the polymer compound (A-3) in terms of standard polystyrene equivalent determined by GPC measurement was 6,900, and the molecular weight dispersion degree (Mw/Mn) was 1.76. The copolymerization compositional ratio (the proportion (molar ratio) of each constitutional unit in the structural formula) (l/m) acquired by $^{13}$C-NMR was 40/60.

(A)-4: polymer compound represented by Chemical Formula (A-4). The weight average molecular weight (Mw) of the polymer compound (A-4) in terms of standard polystyrene equivalent determined by GPC measurement was 7,200, and the molecular weight dispersion degree (Mw/Mn) was 1.69. The copolymerization compositional ratio (the proportion (molar ratio) of each constitutional unit in the structural formula) (l/m/n/o) acquired by $^{13}$C-NMR was 15/30/50/5.

(A)-5: polymer compound represented by Chemical Formula (A-5). The weight average molecular weight (Mw) of the polymer compound (A-5) in terms of standard polystyrene equivalent determined by GPC measurement was 7,200, and the molecular weight dispersion degree (Mw/Mn) was 1.69. The copolymerization compositional ratio (the proportion (molar ratio) of each constitutional unit in the structural formula) (l/m/n/o) acquired by $^{13}$C-NMR was 15/30/50/5.

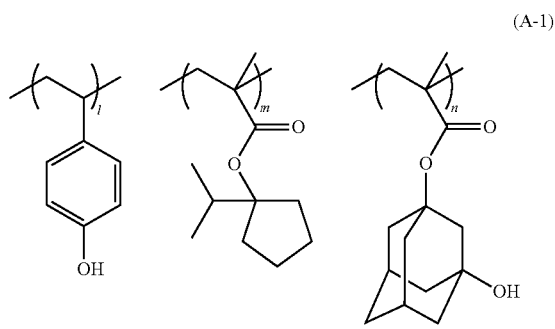

(A-1)

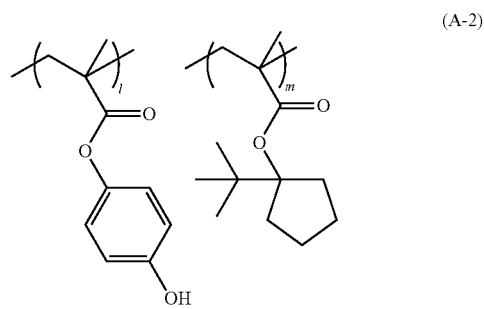

(A-2)

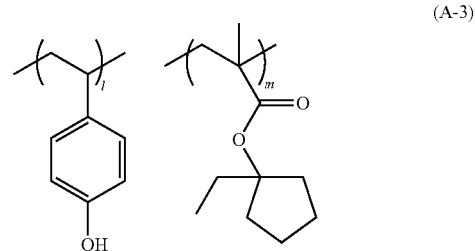

(A-3)

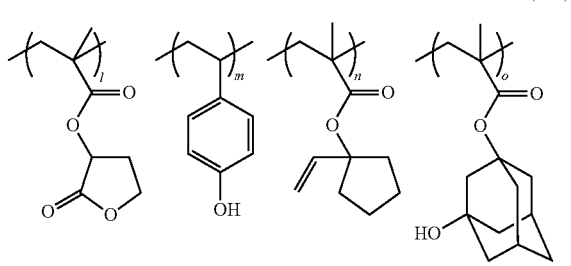

(A-4)

-continued
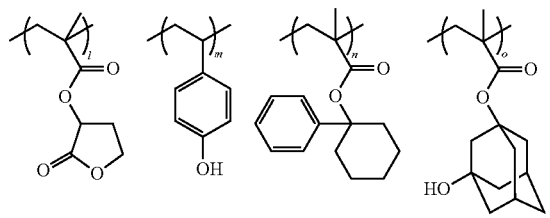
(A-5)
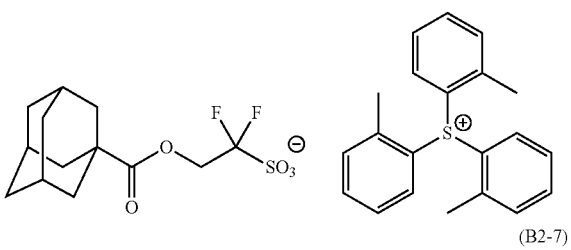
(B2-6)
(B2-7)
(B1)-1 to (B1)-10: respective acid generators including the compounds (B1-1) to (B1-10) described above.
(B2)-1 to (B2)-11: respective acid generators including the compounds (B2-1) to (B2-11) described below.
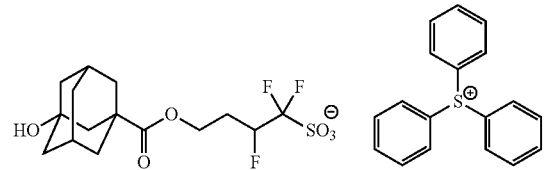
(B2-1)
(B2-2)
(B2-3)
(B2-4)
(B2-5)
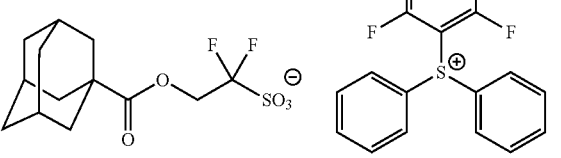
(B2-8)
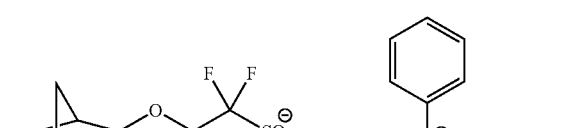
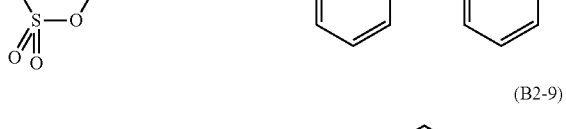
(B2-9)
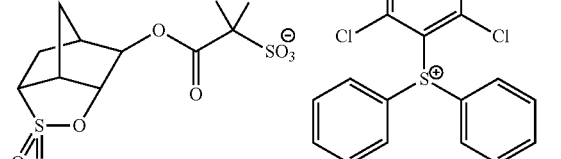
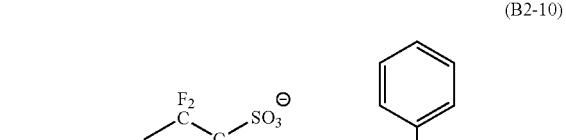
(B2-10)
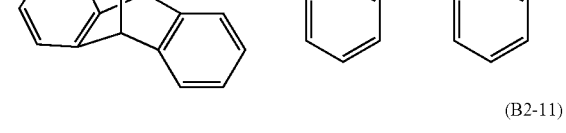
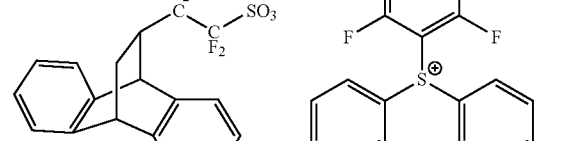
(B2-11)
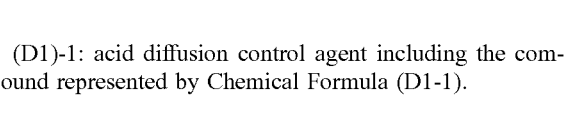
(D1)-1: acid diffusion control agent including the compound represented by Chemical Formula (D1-1).

(D2)-1: acid diffusion control agent including the compound represented by Chemical Formula (D2-1).

(S)-1: mixed solvent of propylene glycol monomethyl ether acetate/propylene glycol monomethyl ether=60/40 (mass ratio).

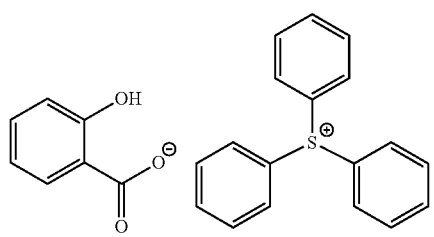

(D2-1)

<Formation of Resist Pattern>

An 8-inch silicon substrate which had been treated with hexamethyldisilazane (HMDS) treatment was coated with each resist composition of the examples using a spinner, and a prebake (PAB) treatment was performed thereon on a hot plate at a temperature of 110° C. for 60 seconds so that the composition was dried to form a resist film having a film thickness of 30 nm.

A drawing (exposure) was carried out on the resist film using an electron beam lithography apparatus JEOL-JBX-9300FS (manufactured by JEOL Ltd.) with acceleration voltage of 100 kV and a target size of 1:1 line-and-space pattern (hereinafter referred to as an "LS pattern") having a line width of 20 to 50 nm. Thereafter, the resist film was subjected to a post-exposure bake (PEB) treatment at 110° C. for 60 seconds.

Alkali development was performed for 60 seconds at 23° C. using 2.38 mass % tetramethylammonium hydroxide (TMAH) aqueous solution "NMD-3" (trade name, manufactured by Tokyo Ohka Kogyo Co., Ltd.).

The resist film was rinsed with pure water for 15 seconds.

Consequently, 1:1 LS pattern with a line width of 20 to 50 nm was formed.

[Evaluation of Optimum Exposure Amount (Eop)]

An optimum exposure amount Eop ($\mu C/cm^2$) at which the LS pattern of the target size was formed was acquired by the method for forming a resist pattern described above. The results are listed in Tables 6 to 10 as "Eop ($\mu C/cm^2$)".

[Evaluation of LWR (Line Width Roughness)]

For the LS pattern formed in <Formation of Resist Pattern>, 3σ, which is a scale indicating LWR, was determined. The results are summarized in Tables 6 to 10 as "LWR (nm)".

"3σ" refers to a triple value (3σ) (unit: nm) of a standard deviation (σ) calculated from the results which are measured at 400 points of line positions in a longitudinal direction of a line with a scanning electron microscope (acceleration voltage: 800 V, trade name: S-9380, manufactured by Hitachi High-Technologies Corporation).

The smaller a value of 3σ, the smaller a roughness of a line sidewall, which indicates that the LS pattern with more uniform width is obtained.

TABLE 6

|  | PAB (° C.) | PEB (° C.) | Eop ($\mu C/cm^2$) | LWR (nm) |
|---|---|---|---|---|
| Example 1 | 110 | 110 | 95 | 5.0 |
| Example 2 | 110 | 110 | 90 | 5.1 |

TABLE 6-continued

|  | PAB (° C.) | PEB (° C.) | Eop ($\mu C/cm^2$) | LWR (nm) |
|---|---|---|---|---|
| Example 3 | 110 | 110 | 100 | 4.8 |
| Example 4 | 110 | 110 | 85 | 5.2 |
| Example 5 | 110 | 110 | 85 | 5.0 |
| Comparative Example 1 | 110 | 110 | 115 | 5.9 |
| Comparative Example 2 | 110 | 110 | 125 | 6.6 |
| Comparative Example 3 | 110 | 110 | 105 | 5.7 |
| Comparative Example 4 | 110 | 110 | 110 | 6.0 |

TABLE 7

|  | PAB (° C.) | PEB (° C.) | Eop ($\mu C/cm^2$) | LWR (nm) |
|---|---|---|---|---|
| Example 6 | 110 | 110 | 90 | 5.4 |
| Example 7 | 110 | 110 | 85 | 5.5 |
| Comparative Example 5 | 110 | 110 | 105 | 6.0 |
| Comparative Example 6 | 110 | 110 | 95 | 5.9 |
| Comparative Example 7 | 110 | 110 | 100 | 6.2 |

TABLE 8

|  | PAB (° C.) | PEB (° C.) | Eop ($\mu C/cm^2$) | LWR (nm) |
|---|---|---|---|---|
| Example 8 | 110 | 110 | 105 | 5.4 |
| Example 9 | 110 | 110 | 100 | 5.5 |
| Comparative Example 8 | 110 | 110 | 120 | 6.3 |
| Comparative Example 9 | 110 | 110 | 115 | 6.4 |

TABLE 9

|  | PAB (° C.) | PEB (° C.) | Eop ($\mu C/cm^2$) | LWR (nm) |
|---|---|---|---|---|
| Example 10 | 110 | 110 | 95 | 5.1 |
| Example 11 | 110 | 110 | 85 | 5.1 |
| Example 12 | 110 | 110 | 100 | 5.0 |
| Example 13 | 110 | 110 | 90 | 4.9 |
| Example 14 | 110 | 110 | 90 | 4.8 |
| Comparative Example 10 | 110 | 110 | 115 | 5.6 |
| Comparative Example 11 | 110 | 110 | 125 | 5.5 |
| Comparative Example 12 | 110 | 110 | 105 | 5.9 |
| Comparative Example 13 | 110 | 110 | 110 | 6.0 |

TABLE 10

|  | PAB (° C.) | PEB (° C.) | Eop ($\mu C/cm^2$) | LWR (nm) |
|---|---|---|---|---|
| Example 15 | 110 | 110 | 95 | 4.9 |
| Example 16 | 110 | 110 | 90 | 4.9 |
| Comparative Example 14 | 110 | 110 | 115 | 5.1 |
| Comparative Example 15 | 110 | 110 | 110 | 5.0 |

As seen from the results shown in Tables 6 to 10, according to the resist compositions of Examples, it is possible to achieve high sensitivity in forming a resist pattern and to form a resist pattern having a good shape with reduced roughness.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition which generates an acid upon exposure and of which solubility in a developing solution is changed due to an action of an acid, the resist composition comprising:

a base material component (A) of which solubility in a developing solution is changed due to an action of an acid; and a compound (BD1) represented by any one of formulas (bd-1-1) to (bd-1-15):

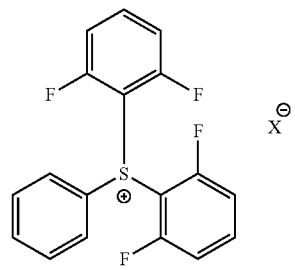
(bd-1-1)

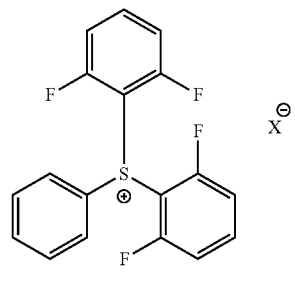
(bd-1-2)

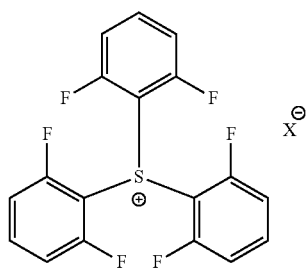
(bd-1-3)

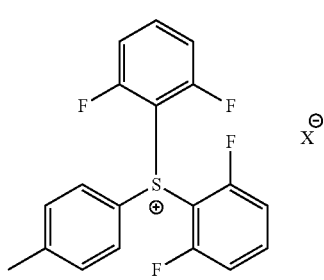

-continued

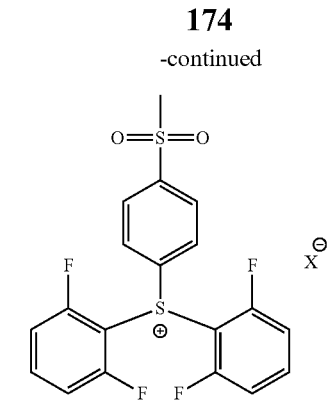
(bd-1-4)

(bd-1-5)

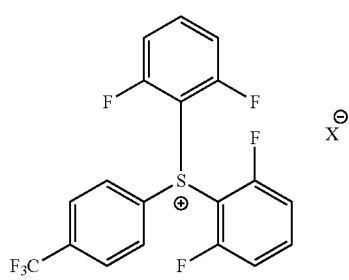
(bd-1-6)

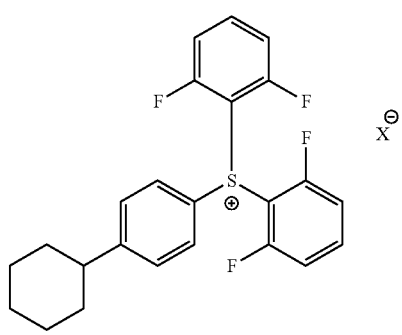
(bd-1-7)

(bd-1-8)

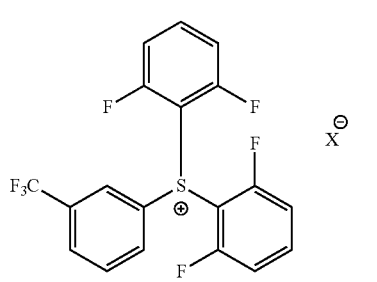

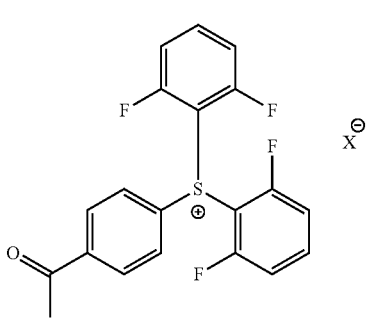

(bd-1-9)

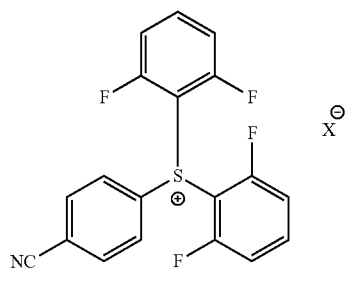

(bd-1-14)

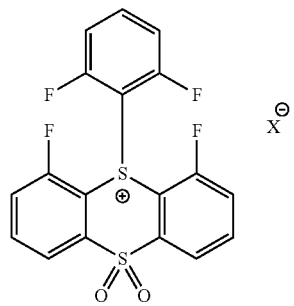

(bd-1-10)

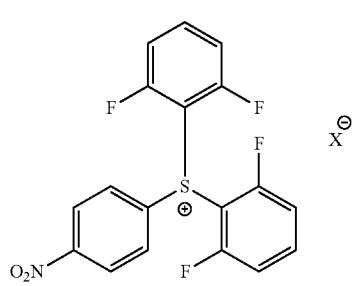

(bd-1-15)

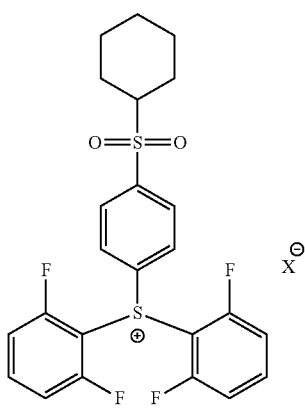

(bd-1-11)

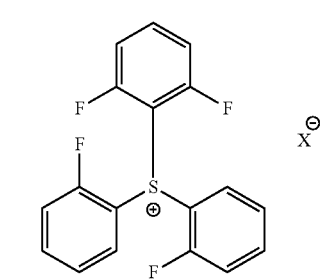

wherein X⁻ represents a counter anion.

2. A method of forming a resist pattern, comprising:

forming a resist film on a support using the resist composition according to claim 1;

exposing the resist film; and developing the exposed resist film to form a resist pattern.

3. The method of forming a resist pattern according to claim 2, wherein the resist film is exposed with extreme ultraviolet (EUV) rays or an electron beam (EB).

4. A compound represented by any one of formulas (bd-1-1) to (bd-1-15), (bd-1-12)

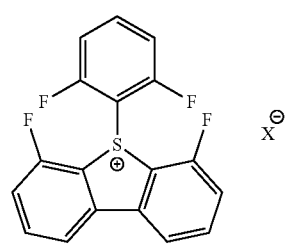

(bd-1-13)

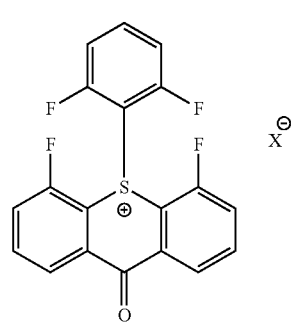

(bd-1-1)

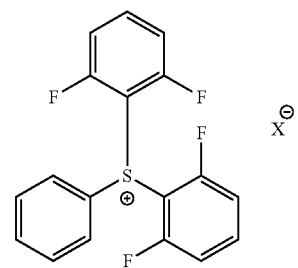

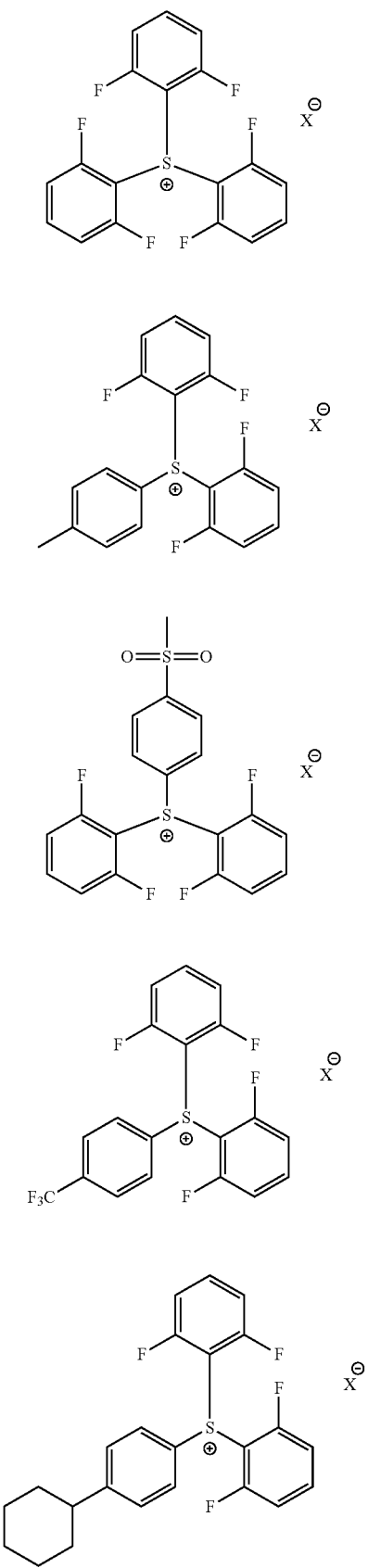
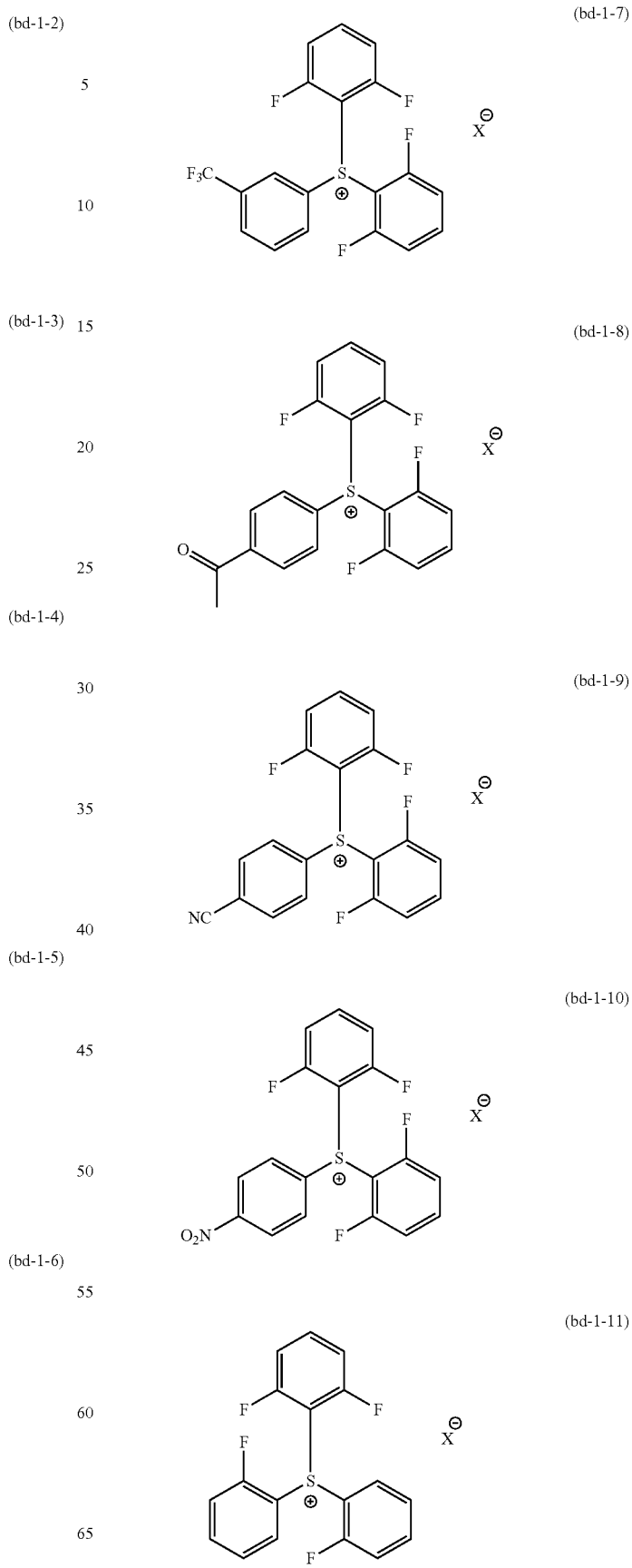

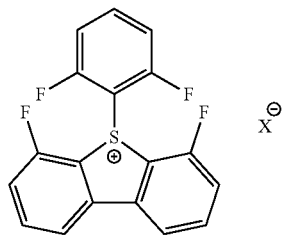
(bd-1-12)
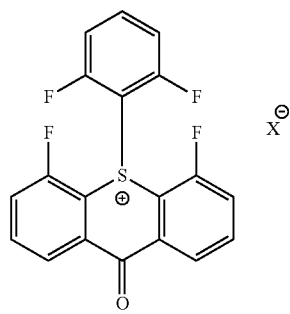
(bd-1-13)
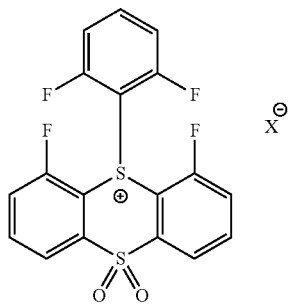
(bd-1-14)
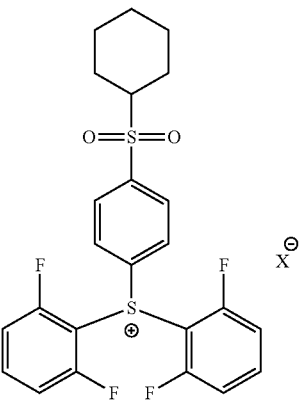
(bd-1-15)
wherein X⁻ represents a counter anion.
* * * * *